US010808238B2

(12) United States Patent
Walker et al.

(10) Patent No.: US 10,808,238 B2
(45) Date of Patent: Oct. 20, 2020

(54) STABILIZATION OF BIOMOLECULES BY ATTACHMENT OF RESPONSIVE POLYMERS AND SENSORS THEREOF

(71) Applicant: FLIR Detection, Inc., Pittsburgh, PA (US)

(72) Inventors: Jeremy P. Walker, Oakmont, PA (US); David C. Wilson, Monroeville, PA (US); Anna M. Leech, Pittsburgh, PA (US); Jessica J. Sinclair, Murrysville, PA (US)

(73) Assignee: FLIR DETECTION, INC., Pittsburgh, PA (US)

( * ) Notice: Subject to any disclaimer, the term of this patent is extended or adjusted under 35 U.S.C. 154(b) by 723 days.

(21) Appl. No.: 14/581,203

(22) Filed: Dec. 23, 2014

(65) Prior Publication Data

US 2015/0376594 A1 Dec. 31, 2015

Related U.S. Application Data

(60) Provisional application No. 62/030,118, filed on Jul. 29, 2014, provisional application No. 61/930,581, filed on Jan. 23, 2014.

(51) Int. Cl.
*C12N 9/96* (2006.01)
*C12N 11/08* (2020.01)
(Continued)

(52) U.S. Cl.
CPC ................ *C12N 9/96* (2013.01); *A61K 31/74* (2013.01); *A61K 31/785* (2013.01); *A61K 31/79* (2013.01); *A61K 47/58* (2017.08); *C07K 14/765* (2013.01); *C08F 122/38* (2013.01); *C12N 9/0006* (2013.01); *C12N 9/16* (2013.01); *C12N 9/20* (2013.01); *C12N 9/88* (2013.01); *C12N 11/08* (2013.01); *C12Q 1/54* (2013.01); *A61K 38/00* (2013.01); *G01N 2333/904* (2013.01)

(58) Field of Classification Search
None
See application file for complete search history.

(56) References Cited

U.S. PATENT DOCUMENTS

2011/0117623 A1* 5/2011 Walker .................. A61K 31/74 435/182
2013/0244301 A1 9/2013 Walker et al.

OTHER PUBLICATIONS

Pedrosa, V.A et al., Micropatterned Nanocomposite Hydrogels for Biosensing Applications, Electroanalysis, 2011, vol. 23, No. 05, pp. 1142-1149, Wiley-VCH Verlag GmbH & Co. KGaA, Weinheim.
(Continued)

*Primary Examiner* — Robert J Yamasaki
*Assistant Examiner* — Charles Zoltan Constantine
(74) *Attorney, Agent, or Firm* — Sterne, Kessler, Goldstein & Fox P.L.L.C.

(57) ABSTRACT

The present invention provides a biomolecule conjugate having one or more functionalized biomolecules wherein the biomolecule is functionalized with one or more reactive sites, and at least one polymer capable of undergoing a polymer growth reaction, wherein the polymer is attached to at least one of the reactive sites of the functionalized biomolecule and wherein the polymer envelopes the functionalized biomolecule to form a reversible nanoparticle structure which protects the biomolecule by dynamically collapsing to preserve the biomolecule when an adverse environmental stimulus is present. A method of protecting a biomolecule from environmental conditions is also provided.

23 Claims, 33 Drawing Sheets

(51) Int. Cl.

| | |
|---|---|
| *C12N 9/00* | (2006.01) |
| *C12N 9/16* | (2006.01) |
| *C12N 9/20* | (2006.01) |
| *C12N 9/88* | (2006.01) |
| *C12Q 1/54* | (2006.01) |
| *A61K 31/74* | (2006.01) |
| *A61K 31/785* | (2006.01) |
| *C07K 14/765* | (2006.01) |
| *A61K 31/79* | (2006.01) |
| *A61K 47/58* | (2017.01) |
| *C08F 122/38* | (2006.01) |
| *C12N 9/04* | (2006.01) |
| *A61K 38/00* | (2006.01) |

(56) References Cited

OTHER PUBLICATIONS

Livshin S. et al., Crystallinity and Cross-Linking in Porous Polymers Synthesized from Long Side Chain Monomers through Emulsion Templating, Macromolecules, 2008, vol. 41, pp. 3930-3938, American Chemical Society.

Hakem, I.F. et al., Analysis of Heterogeneity in Nonspecific PEGylation Reactions of Biomolecules, Biopolymers, 2012, vol. 99, No. 07, pp. 427-435, Wiley Periodicals, Inc.

International Search Report and Written Opinion for PCT/US2014/072183 filed Dec. 23, 2014.

\* cited by examiner

| Thermal Half-life (in hours) | | | |
|---|---|---|---|
| Lipase Sample | 23C | 50C | 60C |
| Native Lipase | 16 | 8 | 2.5 |
| COTS Lipase Beads | 48 | 20 | 4 |
| NanoStable Lipase 300kD | >96 | 84 | 30 |
| NanoStable Lipase 150kD | 72 | 48 | 16 |
| NanoStable Lipase 40kD | 20 | 12 | 3 |

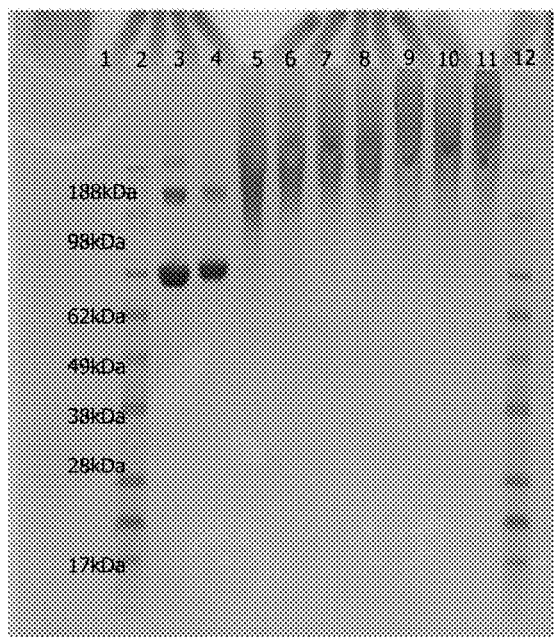
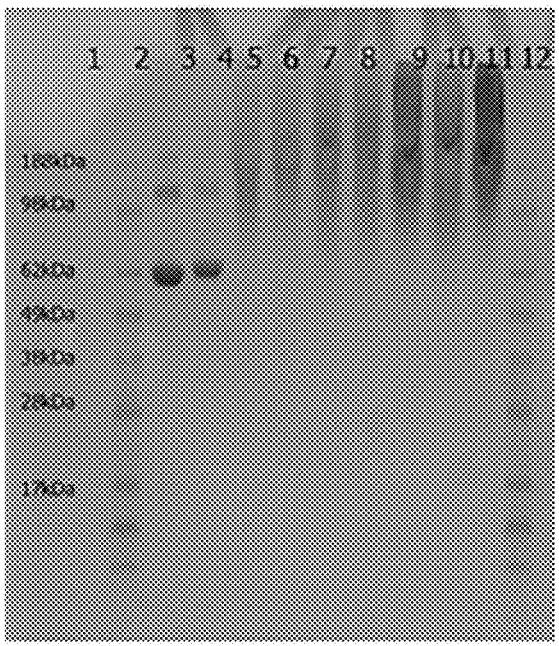
Figure 18        Figure 19
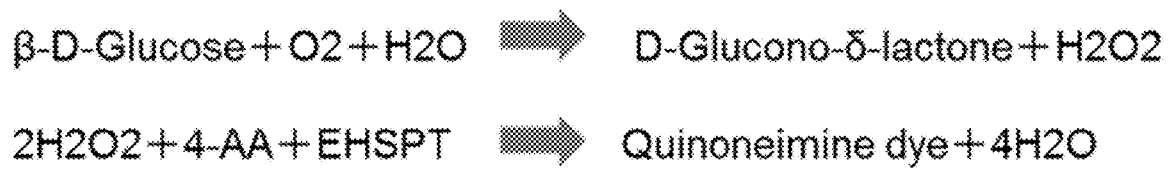
Figure 20

| Sample | Relative Fluorescence Units | % Modification | Number of Lysines Modified |
|---|---|---|---|
| GOX | 3160.32 | 0% | 0 |
| GOX-Br | 1902.49 | 40% | 6 |

| Sample | Relative Fluorescence Units | % Modification with aaNHS | Specific Activity (U/mg) | Retention of Activity (%) to native GOX |
|---|---|---|---|---|
| GOX / NIPAM / APMA | 4925.67 | 0% | 337.42 | 96% |
| GOX / NIPAM / APMA –aa | 3428.71 | 30% | 306.98 | 87.4% |
| GOX | 1021.32 | 0% | 351.32 | 100% |
| GOX-aa | 731.21 | 28% | 334.34 | 95% |

| Label | Hydrogel | GOX Sample | GOX conc (mg/mL) |
|---|---|---|---|
| A1 | Acrylamide | GOX | 2.4 |
| A2 | Acrylamide | GOX | 1.2 |
| A3 | Acrylamide | GOX | 0.6 |
| A4 | Acrylamide | GOX-aa | 2.4 |
| A5 | Acrylamide | GOX-aa | 1.2 |
| A6 | Acrylamide | GOX-aa | 0.6 |
| A7 | Acrylamide | GOX / NIPAM / APMA-aa | 2 |
| A8 | Acrylamide | GOX / NIPAM / APMA-aa | 1 |
| A9 | Acrylamide | GOX / NIPAM / APMA-aa | 0.5 |
| Label | Hydrogel | GOX Sample | GOX conc (mg/mL) |
| H1 | HEMA | GOX | 2.4 |
| H2 | HEMA | GOX | 1.2 |
| H3 | HEMA | GOX | 0.6 |
| H4 | HEMA | GOX-aa | 2.4 |
| H5 | HEMA | GOX-aa | 1.2 |
| H6 | HEMA | GOX-aa | 0.6 |
| H7 | HEMA | GOX / NIPAM / APMA-aa | 2 |
| H8 | HEMA | GOX / NIPAM / APMA-aa | 1 |
| H9 | HEMA | GOX / NIPAM / APMA-aa | 0.5 |

Figure 33

| | Sample | U/mg | % Retention |
|---|---|---|---|
| GOX | GOX | 351.32 | 100 |
| A1 | GOX 2.4 | 6.87 | 1.96 |
| A2 | GOX 1.2 | 10.28 | 2.93 |
| A3 | GOX 0.6 | 11.62 | 3.31 |
| GOX-aa | GOX-aa | 334.34 | 100 |
| A4 | GOX-aa 2.4 | 16.42 | 4.91 |
| A5 | GOX-aa 1.2 | 13.74 | 4.11 |
| A6 | GOX-aa 0.6 | 16.20 | 4.84 |
| NS GOX-aa | GOX / NIPAM / APMA-aa | 306.98 | 100 |
| A7 | GOX / NIPAM / APMA-aa | 58.43 | 19.03 |
| A8 | GOX / NIPAM / APMA-aa | 62.28 | 20.29 |
| A9 | GOX / NIPAM / APMA-aa | 67.50 | 21.99 |

Figure 34

| | Sample | U/mg | % Retention |
|---|---|---|---|
| GOX | GOX | 351.32 | 100 |
| H1 | GOX 2.4 | 5.19 | 1.48 |
| H2 | GOX 1.2 | 8.20 | 2.34 |
| H3 | GOX 0.6 | 10.65 | 3.03 |
| GOX-aa | GOX-aa | 334.34 | 100 |
| H4 | GOX-aa 2.4 | 15.63 | 4.68 |
| H5 | GOX-aa 1.2 | 18.76 | 5.61 |
| H6 | GOX-aa 0.6 | 22.65 | 6.77 |
| NS GOX-aa | GOX / NIPAM / APMA-aa | 306.98 | 100 |
| H7 | GOX / NIPAM / APMA-aa | 63.66 | 20.74 |
| H8 | GOX / NIPAM / APMA-aa | 76.34 | 24.87 |
| H9 | GOX / NIPAM / APMA-aa | 72.16 | 23.51 |

| | U/mg Rinse | % Ret Rinse | U/mg Gel | % Ret Gel |
|---|---|---|---|---|
| A1 | 58.20 | 16.57 | 2.02 | 0.06 |
| A2 | 36.98 | 10.53 | 3.02 | 0.09 |
| A3 | 46.03 | 13.10 | 1.98 | 0.06 |
| A4 | 30.28 | 8.62 | 12.39 | 3.71 |
| A5 | 43.00 | 12.24 | 11.35 | 3.39 |
| A6 | 28.34 | 8.07 | 13.98 | 4.18 |
| A7 | 6.82 | 1.94 | 66.49 | 21.66 |
| A8 | 6.46 | 1.84 | 60.48 | 19.70 |
| A9 | 1.49 | 0.42 | 63.59 | 20.72 |

|   | U/mg Rinse | % Ret Rinse | U/mg Gel | % Ret Gel |
|---|---|---|---|---|
| H1 | 47.96 | 13.65 | 1.95 | 0.06 |
| H2 | 28.59 | 8.14 | 2.09 | 0.06 |
| H3 | 29.60 | 8.43 | 1.42 | 0.04 |
| H4 | 38.64 | 11.56 | 12.35 | 3.69 |
| H5 | 39.00 | 11.67 | 13.04 | 3.90 |
| H6 | 56.66 | 16.95 | 12.90 | 3.86 |
| H7 | 2.70 | 0.88 | 66.91 | 21.80 |
| H8 | 1.57 | 0.51 | 73.19 | 23.84 |
| H9 | 1.51 | 0.49 | 70.10 | 22.84 |

| Hydrogel | Enzyme | U/mg SM | aaNHS % Mod | # Lysines Mod | U/mg Mod | % Ret Mod | U/mg Gel | %Ret Gel | U/mg Rinse | % Ret Rinse | U/mg Rinse to SM | % Ret Rinse to SM |
|---|---|---|---|---|---|---|---|---|---|---|---|---|
| Acrylamide | GOX | 351.21 | 0.00 | 0.00 | 351.21 | 100.00 | 9.59 | 2.73 | 2.34 | 0.07 | 2.34 | 0.67 |
| Acrylamide | GOX-aa | 351.21 | 27.92 | 4.20 | 334.34 | 95.20 | 15.45 | 4.62 | 12.57 | 3.76 | 12.57 | 3.58 |
| Acrylamide | GOX/NIPAM/APMA-aa | 337.42 | 30.39 | 21.90 | 306.98 | 90.98 | 62.74 | 20.44 | 63.52 | 20.69 | 63.52 | 18.83 |
| HEMA | GOX | 351.21 | 0.00 | 0.00 | 351.21 | 100.00 | 8.01 | 2.28 | 1.82 | 0.05 | 1.82 | 0.52 |
| HEMA | GOX-aa | 351.21 | 27.92 | 4.20 | 334.34 | 95.20 | 19.01 | 5.69 | 12.76 | 3.82 | 12.76 | 3.63 |
| HEMA | GOX/NIPAM/APMA-aa | 337.42 | 30.39 | 21.90 | 306.98 | 90.98 | 70.72 | 23.04 | 70.07 | 22.83 | 70.07 | 20.77 |

Figure 42

|  | Relative Activity (%) |
|---|---|
| GOX | 100.0 |
| GOX-PA | 91.8 |
| GOX-PA-aa | 83.4 |
| MA-80 | 79.2 |
| Monomer Mixture | 70.5 |
| KPS / 40 °C | 65.9 |
| 15 min | 64.4 |
| 30 min | 58.8 |
| 45 min | 55.6 |
| 60 min | 53.3 |
| Walker et. al. | 62.0 |

Figure 55

|  | Relative Activity (%) |
|---|---|
| GOX | 100.0 |
| GOX-Br | 97.0 |
| 15 min | 96.4 |
| 30 min | 96.3 |
| 45 min | 97.4 |
| 60 min | 96.5 |
| NanoStable GOX/NiPAM | 96.3 |

Figure 56

STABILIZATION OF BIOMOLECULES BY ATTACHMENT OF RESPONSIVE POLYMERS AND SENSORS THEREOF

CROSS-REFERENCE TO RELATED APPLICATIONS

This utility patent application claims the benefit of co-pending U.S. Provisional Patent Application Ser. No. 61/930,581, filed on Jan. 23, 2014, and co-pending U.S. Provisional Patent Application Ser. No. 62/030,118, filed on Jul. 29, 2014. The entire contents of U.S. Provisional Patent Application Ser. No. 61/930,581 and U.S. Provisional Patent Application Ser. No. 62/030,118 are incorporated by reference into this utility patent application as if fully written herein.

BACKGROUND OF THE INVENTION

1. Field of the Invention

The present invention relates to a method of stabilizing a biomolecule by covalently attaching one or stimulus-responsive more polymers capable of forming a nanoparticle that dynamically protects the enzyme under varied adverse environmental conditions. Three-dimensional attachment of polymer(s) that respond to stimuli to a biomolecule provides a method to enhance the stability of the biomolecule. As in the case of an enzyme, native enzymes unfold at elevated temperatures and rapidly lose their catalytic activity. The present invention provides enzymes with available surface functional groups capable of being modified directly with a polymer graft or modified with polymers via a controlled radical polymerization from a grafted polymerization initiator in a process that occurs under enzyme-friendly conditions. In one example, the resultant covalent attachment of the enzyme to the polymer allows the tertiary structure of the enzyme to stay intact due to steric support provided by contraction of one or more thermally responsive polymer chains at temperatures above their lower critical solution temperature. The collapsed polymers form a reversible nanoparticle structure that structurally supports the enzyme and prevents it from denaturing at elevated temperatures. Thus, enzyme stability in both the aqueous state and dry state is greatly enhanced at elevated temperatures (defined as those temperatures above the lower critical solution temperature of the thermally responsive polymer chain).

2. Description of the Background Art

Enzymes are biological proteins that accelerate the rate at which chemical reactions take place by lowering the activation energy such that they occur more easily. Enzymes demonstrate a high degree of utility due to their speed of catalytic reaction, specificity for certain substrates, and ability to be engineered and chemically modified. Enzymes are used in many industries including food processing, detergents and cleaning products, clinical diagnostics, fuel production, pharmaceutical manufacturing and decontamination of chemical agents. The major problem associated with the practical utility of enzymes is the inability to sufficiently stabilize their tertiary structure in harsh environmental conditions, such as high temperatures, extreme pH, high salinity and solvents; free enzymes are susceptible to damage from denaturation and will incur partial or total activity loss in the presence of such conditions. As a result, applications of free enzymes for large scale commercial use, especially for continuous use in flowing systems or in sensors which are subject to long storage times or temperature extremes, are extremely limited. The ability to stabilize enzymes in harsh conditions is an area of immense interest; retention of activity in non-optimized environments, such as elevated temperatures, will improve catalytic performance and be beneficial for countless applications. Other biological molecules that could be stabilized by the present invention include, antibodies, viruses, DNA, RNA, Stem Cells, spores and bacteria.

Strategies exist for making reactive group-functionalized polymers that can be grafted onto reactive amino acid residues on the enzyme surface. Controlled/living radical polymerization (CRP/LRP) is a polymerization process that provides improved control over molecular weight, polydispersity, molecular structure, composition and site-specific functionality over other polymerization processes. CRP allows the creation of novel polymer composite materials that would be challenging to produce otherwise. It can be used to link inorganic materials and organic materials; CRP can also be utilized to make gradient, block, di-block, tri-block, multi-arm star copolymers, site-specific functional polymers, and graft copolymers with improved control over polymer polydispersity. It allows manufacturers to improve the properties of their current materials by having better control over the polymerization reaction compared with free radical polymerization techniques.

Atom transfer radical polymerization (ATRP) has been widely developed in the last decade. (Matyjaszewski U.S. Pat. No. 5,789,487). The benefits of ATRP are a low polydispersity index (PDI) and well defined molecular architecture. (Matyjaszewski U.S. Pat. No. 5,789,487). ATRP is a process for the synthesis of novel homopolymer or block graft copolymers, in the presence of an initiating system. The initiating system has an initiator (examples: 1-phenylethyl chloride, 1-phenylethyl bromide, chloroform, carbon tetrachloride, 2-bromopropionitrile, 2-chloroisobutyric acid) having a radically transferrable atom or group, a transition metal complex catalyst (examples: Copper(I)Chloride, Copper(II)Chloride, Copper(I)Bromide, Copper(II)Bromide), and a ligand (examples: ethylenedimine and propylenediamine, bipyridine). A monomer is also needed (examples: styrene, acrylates, methacrylates, vinyl chloroacetate).

A typical ATRP reaction is performed by adding the metal catalyst, ligand and solvent to a Schlenk flask. The flask temperature is kept constant to the conditions that are optimal for the components being used. Then the flask is sealed, degassed and charged with Argon. The monomer is then added while the flask is still filled with argon and under temperature control. After addition of the monomer, the deoxygenated transition metal complex catalyst and ligand are added to the flask and the polymerization reaction is initiated. Other techniques that could be used for polymerization include: Reversible addition-fragmentation chain transfer polymerization (RAFT) and Stable free radical polymerization (SFRP).

Various approaches for stabilizing enzymes have been demonstrated from enzyme adsorption and covalent modification to recombinant protein engineering; these methods only provide a moderate improvement in enzyme stability and are typically not universally applicable to various enzymes and other proteins. Stability of enzymes adsorbed onto nanoparticles is highly dependent on nanoparticle size and adsorption pattern. Protein and nanoparticle interactions during adsorption can cause conformational changes to an enzyme's native structure, rendering it inactive or severely reducing the catalytic activity of the immobilized enzyme. Encapsulation of enzymes within porous, stimulus responsive polymeric nanoparticles has been demonstrated to improve the stability by restricting their ability to unfold (Walker et al., U.S. Pat. No. 8,460,907).

Another method for enhancing the stability of enzymes has been three-dimensional covalent immobilization of enzymes. LeJeune and Russell demonstrated that hydrolase enzymes which detoxify chemical warfare agents could be immobilized within polyurethane foams. The surface lysine residues participate in the cross-linking reaction by condensing with the isocyanate groups on the polyurethane backbone, resulting in a foam material that contains active enzymes which retain superior stability over the native enzyme [see, LeJeune, K. E., "Covalent binding of a nerve agent hydrolyzing enzyme within polyurethane foams", Biotechnology and Bioengineering, Vol. 51, pages 450-457 (1996), and LeJeune, K. E., "Dramatically stabilized phosphotriesterase-polymers for nerve agent degradation", Biotechnology and Bioengineering, Vol. 54, pages 105-114 (1997)]. This work has been extended to numerous enzymes which have been utilized to make enzyme-containing colorimetric sensor pens that have shelf-lives of years at room temperature (see also U.S. Pat. Nos. 6,291,200; 6,673,565; 6,762,213; and 6,759,220). One shortcoming of this approach is that the highly-reactive nature of the polyurethane chemistry results in significant inactivation of the majority of the enzyme entrained within the polymer.

Recently, there has been significant focus on nanoparticle development in a variety of fields including: optics and coatings, clinical diagnostics, drug-delivery, and also in the development of novel materials such as self-healing and highly-porous plastics. Stabilization of covalently-immobilized enzymes within porous, hydrophilic nanogels has been demonstrated by several groups. Polymers which respond to specific stimuli, such as temperature and the presence of other molecules in solution are frequently utilized in particle development. Nanoparticles composed of such polymers have the capability to shrink and swell via changes in Gibbs free energy in the presence of the proper stimulus. Responsive nanoparticles are currently used for drug delivery, bioimaging and therapeutics. The present invention provides three-dimensional attachment of responsive polymers to enzymes at the nanoscale, wherein the enzyme-polymer conjugates function as a single macromolecule which undergoes reversible nanoparticle formation in response to an environmental stress (high temperatures) to prevent the enzyme from denaturing. The responsive polymer materials protect the enzyme by providing a responsive barrier material that will respond to environmental stimuli to collapse and provide structural support under conditions that would otherwise denature the enzyme. The current invention provides an improved method and resulting material over Walker (U.S. Pat. No. 8,460,907) by not encapsulating the enzyme within in an excessively large polymer shell, but rather grafting the polymer or growing the polymer directly from the enzyme surface under more beneficial polymer growth/modification conditions previously not available using the method of Walker et al. (U.S. Pat. No. 8,460,907). This method of this invention results in improved enzyme activity after the polymer modification process over the teachings of U.S. Pat. No. 8,460,907, and further provides improved protection of enzyme function in response to environmental stimuli.

Enzymes have been functionalized and coupled with N-isopropylacrylamide (NiPAAm)-N-hydroxysuccinimide (NHS) [Chen, G., "Preparation and properties of thermoreversible, phase-separating enzymes-oligo (N-isopropylacrylamide) conjugates", Bioconjugate Chemistry, Vol. 4, pages 509-514 (1993)]. NiPAAm is a thermo-responsive polymer that which undergoes a hydrophobic collapse and volume phase transition at temperatures above its lower critical solution temperature (LCST), approximately 32° C. Coupling NiPAAm to an enzyme allows this phenomenon to be used for separation, recovery, and recycling of an enzyme simply by applying small temperature changes to the reaction medium. The growing NiPAAm enzyme chains have also shown moderate improvements in stability of the immobilized enzyme compared to native enzyme. However, heretofore, no one has grown from an enzyme with such precision of polymer group attachment, ease of clean-up, low diffusion barriers and in solvent free environments, as set forth in the present invention.

Incorporation of functional enzymes into nanoparticles has limited use for several reasons. Bottle-in approaches have limited utility because diffusion of enzymes into polymer particles, on a short time scale, is difficult due to small pore size and high polymer concentration on the outer particle shell. Harsh conditions during nanoparticle fabrication such as solvents, surfactants and high temperatures can be detrimental to the tertiary structure of the enzyme (U.S. Pat. No. 8,460,907).

Walker et al. (U.S. Pat. No. 8,460,907) focuses on enzymes covalently encapsulated within nanoparticles comprised of NiPAAm polymers which have shown an increased thermal stability over native enzymes. Through encapsulating and immobilizing an enzyme within responsive NiPAAm nanoparticles, the stability was greatly improved at elevated temperatures; leading to a drastic improvement in both pot life (aqueous state) and shelf life (dry state) stability. The contraction of the particles supports the enzyme's tertiary structure, leaving the enzyme highly folded and active at elevated temperatures; free enzymes which are unencapsulated and unmodified will unfold at these temperatures and become inactive. Walker et al. (U.S. Pat. No. 8,460,907) encapsulates the enzyme within a nanoparticle which has many polymer cross-links, which actually beyond a certain extent prevent further collapse of the nanoparticle shell and hinders the ability of the polymer shell to further prevent enzyme denaturation. In the present invention, the polymers are directly attached to the enzyme and do not need to form a cross-linked shell. The current invention has more three-dimensional flexibility, more ability to collapse further/more tightly around the enzyme, and a lower diffusion barrier which enables the substrate to better access the enzyme. The current invention can form nanoparticles that are smaller than those that are enabled by Walker et al. (U.S. Pat. No. 8,460,907). One skilled in the art will appreciate that free radical nanoparticle polymerization processes, including seeded emulsion reactions, are not able to achieve nanoparticles with diameters less than approximately 25 nanometers in diameter. The present invention allows for a much smaller nanoparticle shell surrounding the enzyme surface. Furthermore, the current invention has also been shown to be more stable. Since the nanoparticles in Walker et al. include a cross-linker, such as bisacrylamide or divinyl benzene, the nanoparticle collapses above the LCST, at some point the cross-linkers prevent full collapse of the poly(N-isopropyl acrylamide) shell at high temperatures, thus some measure of support when the particles are collapsed is not possible due to the mechanical resistance of these cross-links to collapse. The present invention provides improved structural support for enzymes as the collapsed polymer chains are not sterically restricted from fully collapsing. Thus, superior thermal stability measurements have been observed for the polymer-modified enzymes of the present method over the method of Walker et al.

In Walker et al. (U.S. Pat. No. 8,460,907), the enzyme is cross-linked into a polymeric nanoparticle that contains cross-linkers. While the enzyme is protected from denaturation by the thermal collapse of the thermally responsive polymeric structure at elevated temperatures, the extent to which the polymer chains can collapse and stabilize the enzyme is limited by the presence of the cross-linker, which acts with a repulsive force (like a contracted spring) to prevent further compression. In current invention, the polymer is grown from the surface of the protein and is not covalently cross-linked, therefore when the polymers collapse at elevated temperatures, they can collapse and constrict all the way to the surface of the enzyme, providing more rigid structural support. This translates to improved retention of activity (stability) of the current invention technology compared with Walker et al. (U.S. Pat. No. 8,460,907).

Further, even if Walker et al. (U.S. Pat. No. 8,460,907) did not use a cross-linker in their nanoparticles the particles would still be cross-linked together by the enzymes. Each enzyme has a plurality of vinyl/acrylate groups added to it and would cross-link the polymer matrix, therefore the materials would not be individual nanoparticles containing only a single enzyme. Additionally, without the cross-linker in Walker et al. (U.S. Pat. No. 8,406,907) the enzyme would lose more activity due to the cross-linkers absence. The cross-linker further takes up some of the free-radicals during polymerization. These free radicals can further deactivate the enzyme.

The application of enzymes is limited due to their poor stability in the presence of elevated temperatures. Known techniques to date have focused on providing shells that essentially prevent/limit diffusion or prevent uptake of water. Silica encapsulation has worked well for shelf-life stability; however this technique alone is insufficient for providing operational stability to enzymes. Static shells are unable to dynamically change volume or porosity to limit diffusion and provide a support network for the enzyme. Collapsible shells work better than static shells for enzyme stability however, they still limit diffusion due to the shell around the enzyme.

SUMMARY OF THE INVENTION

The present invention provides an enzyme-friendly methodology for attaching enzymes to stimulus responsive polymers using standard CRP protocols, such protocols are known by those persons skilled in the art. Incorporating functional enzymes into nanoparticles which are constructed from responsive polymers will further stabilize enzymes in harsh environments (for example, elevated temperature, oxidation, harsh solvents, unfavorable pH and physical forces).

The resulting functionalized enzyme conjugate-nanoparticle systems of the present invention have numerous applications. Enzymes generally demonstrate immense utility for a variety of industrial catalysis processes because they can provide improved specificity and enantioselectivity over conventional organometallic catalysts; however intense environmental conditions and inability to reuse the catalysts in harsh conditions limit the efficiency of using enzymes. The nanocatalysts and nanoparticles of the present invention stabilize enzymes to survive such intense environmental conditions including, such as for example but not limited to, temperature extremes. The nanocatalysts and nanoparticles of the present invention have high degree of utility for toxic chemical decontamination, chemical remediation, drug delivery, wound healing, drug and chemical manufacturing, components in sensors and diagnostic devices, components in responsive coatings and fabrics, stabilization of therapeutics and protein therapy and a host of other applications.

The present invention provides a biomolecule comprising one functionalized biomolecule wherein, the biomolecule is functionalized with one or more sites and having at least one polymer chain having a first end and a second end. The first end of the chain is attached to the site on the functionalized biomolecule. The second end of the chain is free moving. The chain comprises at least two polymers, wherein at least one polymer is stimulus responsive. The chain collapses in response to the stimuli and envelopes the functionalized biomolecule to form a reversible nanoparticle structure. The chain is not cross-linked.

Another embodiment of the present invention provides a biomolecule conjugate comprising one functionalized biomolecule, wherein the biomolecule is functionalized with one or more sites, and at least one polymer capable of undergoing a polymer growth reaction, wherein the polymer is attached to at least one of the sites of the functionalized biomolecule and wherein the polymer envelopes (surrounds) the functionalized biomolecule to form a reversible nanoparticle structure. Preferably, the biomolecule conjugate, as described herein, includes wherein the functionalized biomolecule is freely mobilized within the reversible nanoparticle structure. Another embodiment of this invention provides wherein the biomolecule conjugate, as described herein, includes wherein the nanoparticle structure has a diameter between 5 nanometers and 1000 nanometers.

In the present invention, the biomolecule conjugate, as described herein, includes wherein the functionalized biomolecule is one or more enzymes, proteins, antibodies, or biological catalysts. Preferably, the biomolecule conjugate includes wherein the enzyme, protein, or biological molecule remains in a properly-folded position and retains active conformation (tertiary structure) within the nanoparticle structure.

In another embodiment of this invention, the biomolecule conjugate includes wherein the thermally responsive polymer is collapsible as an environmental temperature rises and the enzyme remains highly folded and in an un-denatured state.

The present invention provides a biomolecule conjugate that has improved stability over a native biomolecule at temperatures greater than 30 degrees Centigrade in both aqueous solutions and dry powders, and a biomolecule conjugate wherein the functionalized biomolecule is stable at temperatures ranging from zero degrees Centigrade to 30 degrees Centigrade. Preferably, the biomolecule conjugate includes a protein that is stable at temperatures greater than 30 degrees Centigrade or above the lower critical solution temperature of the thermoresponsive polymer.

One skilled in the art would appreciate that proteins are comprised of many different sites available for modification including but not limited to amino acid residues, lysines, carboxylic acid groups, hydroxyl groups and thiols. Amino acid residues have a multitude of possible side chain functionalities from which to perform covalent attachment chemistries. Lysine residues are prominent amino acids which contain primary amine functionalities, from which any number of functional attachment chemistry can be performed, including, but not limited to grafting of succinimidyl esters to an amide bond, ring-opening epoxidation, isocyanate and isothiocyanate condensation, and carbodiimide coupling. Further, other amino acids residues contain side chains containing carboxylic acid groups, hydroxyl groups, and thiols that can also be covalently modified with functional groups suitable for attaching a polymer graft or a polymerization initiator to the protein in a multitude of possible positions on the surface of the protein. One skilled in the art will appreciate that proteins containing these amino acids in their native structure may be modified in a multitude of manners including replacement of one amino acid with another, or appending one or more amino acids to the C-terminus or N-terminus of the protein's amino acid sequence, effectively making virtually any protein amenable to polymer-functionalization.

One skilled in the art will also appreciate that molecular biology engineering techniques allow for introduction of non-native amino acids such that, for example, a protein not containing a lysine residue may be functionalized with one in a facile manner, indeed replacement of surface glutamic acid residues with lysines is a common substitution to functionalize proteins with primary amines. Additionally, proteins contain terminal carboxylate residues and amine residues which may be covalently modified with appropriate and well-known chemical functionalities. Further, one skilled in the art will understand that such proteins may also have addition amino acid sequences of one or more amino acids containing one or more type of chemical side groups such that the intact protein sequence may not be modified, but an appended amino acid sequence may be modified with a graft polymer or have a polymer grown from said side group.

All of the abovementioned techniques enable any protein to be capable of being polymer graft modified at one or more sites or of being modified with an appropriate polymerization initiator at one or more sites such that one or more polymer chains may be grown from the surface of said protein.

Another embodiment of the present invention provides a sensor having a biomolecule conjugate comprising one or more functionalized biomolecules, wherein the biomolecule is functionalized with one or more sites, and at least one polymer capable of undergoing a polymer growth reaction, wherein the polymer is attached to at least one of the sites of the functionalized biomolecule and wherein the polymer envelopes (surrounds) the functionalized biomolecule to form a reversible nanoparticle structure. Preferably, the biomolecule conjugate, as described herein, of the sensor of the present invention, includes wherein the functionalized biomolecule is freely mobilized within the reversible nanoparticle structure. Another embodiment of this invention provides wherein the sensor has a biomolecule conjugate, as described herein, that includes wherein the nanoparticle structure has a diameter between 5 nanometers and 1000 nanometers.

BRIEF DESCRIPTION OF THE DRAWINGS

FIG. 5 (B) shows the Carbonic Anhydrase pNiPAAm Particles at 60° C.

FIG. 18 is an SDS-PAGE gel of unmodified and modified OPH. Lane 1 is empty. Lane 2 has molecular weight marker (Life technologies LC5925). Lane 3 has native Bovine Serum Albumin (BSA). Lane 4 has BSA and initiator (NHS-TEG-Br). Lane 5 has ATRP modified BSA with pNiPAAm (8.3 mg/mL). Lane 6 has ATRP modified BSA that was first modified with pNiPAAm (8.3 mg/mL) then it was subsequently further ATRP modified with 1.6% PEGMA475 (Sigma). Lane 7 has ATRP modified BSA that was first modified with pNiPAAm (8.3 mg/mL) then it was subsequently further ATRP modified with 3.3% PEGMA475 (Sigma). Lane 8 has ATRP modified BSA that was first modified with pNiPAAm (8.3 mg/mL) then it was subsequently ATRP modified with 6.6% PEGMA475 (Sigma). Lane 9 has ATRP-modified BSA that was first modified with pNiPAAm (8.3 mg/mL) and was subsequently further ATRP modified with 10.0% PEGMA475 (Sigma) to create a block copolymer conjugate. Lane 10 has ATRP modified BSA that was first modified with pNiPAAm (8.3 mg/mL) then it was subsequently further ATRP modified with 13.3% PEGMA475 (Sigma). Lane 11 has ATRP modified BSA that was first modified with pNiPAAm (8.3 mg/mL) then it was subsequently further ATRP modified with 16.67% PEGMA475 (Sigma). Lane 12 has molecular weight marker (Life technologies LC5925).

FIG. 19 is an SDS-PAGE gel of unmodified and modified OPH from FIG. 18. The gel further stained with Barium Iodine, which will selectively stain PEG. Lane 1 is empty. Lane 2 has molecular weight marker (Life technologies LC5925). Lane 3 has native BSA. Lane 4 has BSA and initiator (NHS-TEG-Br). Lane 5 has ATRP modified BSA with pNiPAAm (8.3 mg/mL). Lane 6 has ATRP modified BSA that was first modified with pNiPAAm (8.3 mg/mL) then it was subsequently further ATRP modified with 1.6% PEGMA475 (Sigma). Lane 7 has ATRP modified BSA that was first modified with pNiPAAm (8.3 mg/mL) then it was subsequently further ATRP modified with 3.3% PEGMA475 (Sigma). Lane 8 has ATRP modified BSA that was first modified with pNiPAAm (8.3 mg/mL) then it was subsequently further ATRP modified with 6.6% PEGMA475 (Sigma). Lane 9 has ATRP modified BSA that was first modified with pNiPAAm (8.3 mg/mL) then it was subsequently further ATRP modified with 10.0% PEGMA475 (Sigma). Lane 10 has ATRP modified BSA that was first modified with pNiPAAm (8.3 mg/mL) then it was subsequently further ATRP modified with 13.3% PEGMA475 (Sigma). Lane 11 has ATRP modified BSA that was first modified with pNiPAAm (8.3 mg/mL) then it was subsequently further ATRP modified with 16.67% PEGMA475 (Sigma). Lane 12 has molecular weight marker (Life technologies LC5925).

FIG. 20 shows the reaction scheme of glucose oxidase catalyzing the conversion of glucose into glucono-o-lactone and hydrogen peroxide. The second reaction is peroxidase catalyzing the reaction of hydrogen peroxide with 4-aminoantipyrine and 3-(N-Ethyl-3-methylanilino)2-hydroxypropanesulfonic acid to form a quinoneimine dye and water.

FIG. 33 is a table showing the samples prepared in Example 8.

FIG. 34 is a table containing the catalytic activity of GOX variants retained in the polyacrylamide hydrogel samples after the initial UV cure.

FIG. 42 is a table with a summary of catalytic activity retention from the GOX starting material used through modification, hydrogel polymerization and retention in the hydrogel after rinsing.

FIG. 55 is a table of the relative activity of the '907 nanoparticles throughout the nanoparticle process.

FIG. 56 is a table of the relative activity of the NanoStable GOX/NiPAM throughout the nanoparticle process.

DETAILED DESCRIPTION OF THE INVENTION

Figure 1:
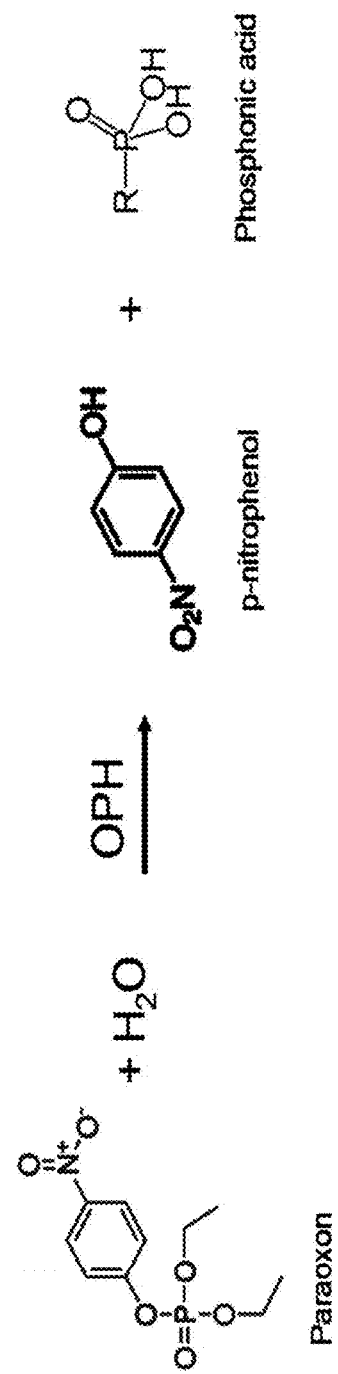
FIG. 1 shows the enzymatic assay used to determine catalytic activity of organophosphorus hydrolase (OPH). The assay is performed at room temperature by determining the increase of p-nitrophenol concentration in the presence of excess paraoxon. OPH catalyzes the hydrolysis of paraoxon; for each mole of paraoxon degraded, a mole of p-nitrophenol and a mole of phosphonic acid are produced. The rate of the reaction is directly proportional to the production of p-nitrophenol; the increase of p-nitrophenol is monitored through an increase in absorbance versus time at 405 nm.

This invention provides a dynamically responsive and reversible/transient polymeric nanoparticle platform for stabilization of enzymes and other proteins at high temperatures. The terms "high temperature" and "high temperatures", as used herein, are defined as temperatures that are above the lower critical solution temperature (LCST) of the thermally responsive polymer, and more preferably temperatures ranging from greater than 30 degrees Centigrade up to 150 degrees Centigrade, which encompass the temperature range in which most enzymes unfold/denature and lose catalytic activity very quickly. The term "low temperature" and "low temperatures", as used herein, are defined as temperatures below the LCST of the polymer, wherein the polymer is hydrophilic and chains are largely extended in aqueous media. More specifically, our examples illustrate polymer materials exposed to temperatures ranging from 30 degrees Centigrade and below, and more preferably temperatures ranging from 30 degrees Centigrade to zero (0) degrees Centigrade.

The term "enzyme" and "enzymes", as used herein, refers generally to proteins that catalyze biochemical reactions. Enzymes are powerful catalysts because they are highly specific. The responsive nanoparticles of the present invention stabilize enzymes and biological catalysts. Preferably the enzymes are selected from the group consisting of lyases, hydrolases, oxidoreductases, transferases, isomerases, and ligases, and combinations thereof. In general, six classes or types of enzymes (as classified by the type of reaction that is catalyzed) are recognized. Enzymes catalyzing reduction/oxidation or redox reactions are referred to generally as EC 1 (Enzyme Class 1) Oxidoreductases. Enzymes catalyzing the transfer of specific radicals or groups are referred to generally as EC2 (Enzyme Class 2) Transferases. Enzymes catalyzing hydrolysis are referred to generally as EC 3 Hydrolases. Enzymes catalyzing removal from or addition to a substrate of specific chemical groups are referred to generally as EC 4 Lyases. Enzymes catalyzing isomerization are referred to generally as EC 5 Isomerases. Enzymes catalyzing combination or binding together of substrate units are referred to generally as EC 6 Ligases. Hydrolase enzymes include, but are not limited to, a lipase, a phosphatase, an amylase, a cellulase, a protease, a peptidase, a urease, an esterase or a deaminase. Specific examples of suitable hydrolases include but are not limited to, organophosphorus hydrolase (OPH), organophosphorus acid anhydrolase (OPAA), urease, butyrylcholinesterase or acetylcholinesterase. One or a plurality of enzymes, or combinations thereof, may be incorporated within the responsive nanoparticles of the present invention. In a most preferred embodiment of the thermally responsive nanoparticles of the present invention as described herein, one or more purified enzymes are selected from the group consisting of one or more of organophosphorus acid anhydrolase (OPAA), organophosphorus hydrolase (OPH), glucose oxidase (GOx), and acetylcholinesterase (AChE).

The term "biological catalyst" and "biological catalysts", as used herein, refer to a substance that increases the rate of biological processes or reactions, and is for example, an enzyme. An enzyme is a protein that functions as a biological catalyst. Enzymes catalyze reactions by lowering the activation energy—the energy input needed to bring about the reaction.

The term "denatured enzyme", as used herein, refers to an enzyme that cannot operate because the shape of its active site is altered due to loss of tertiary structure integrity, thus the substrate cannot effectively interact with the reaction site to produce the reaction product(s)—due to the enzymes loss of tertiary structure resulting in loss of biological catalytic function.

The terms "protein" and "proteins", as used herein, refers to any of a group of complex organic macromolecules that contain carbon, hydrogen, oxygen, nitrogen, and usually sulfur, and include such as for example but not limited to, substances such as enzymes, hormones, and antibodies. "Proteins" include addition enzymes such as asparaginase and non-catalytic proteins such as erythropoietin. "Proteins" may be of many types, such as for example but not limited to, the following:

Proteinaceous hormones are responsible for the regulation of many processes in organisms. Hormones are usually quite small and can be classifies as peptides. Most known protein hormones are: insulin, growth factor, lipotropin and prolactin. Many protein hormones are predecessor of peptide hormones, such as endorfine and enkephalin.

Transport proteins are proteins that transport (or store) other chemical compounds and ions, such as: cytochrome C, an electron transport protein, haemoglobin and myoglobin oxygen transport proteins and albumin, a fatty acid transport protein in the blood stream.

Antibodies are proteins that are involved in the immune response. Sometimes antibodies can act as enzymes. Antibodies can also be classified into a larger group of proteins called protective proteins, such as: lymphocyte antigen-recognizing receptors, antivirals agents such as interferon and tumor necrosis factor. Fibrin and thrombin (blood clotting proteins) should be classified as protective proteins as well.

Structural proteins are proteins that maintain structures of other biological components, like cells and tissues. Collagen, elastin, α-keratin, sklerotin and fibroin are proteins that are involved in the formation of the whole organism body. Bacterial proteoglycans and virus coating proteins also belong to this group of proteins.

Motor proteins are proteins that can convert chemical energy into mechanical energy, such as, actin and myosin which are responsible for muscular motion.

Receptors are proteins that are responsible for signal detection and translation into other type of signal. Sometimes these proteins are active only in complex with low molecular weight compounds. Rhodopsin, a light detecting proteins is a well-known member of this protein family.

Signaling proteins are proteins that are involved in signaling translation processes. Typically they change conformation significantly in the presence of a signaling molecule. These proteins can sometimes act as enzymes.

Storage proteins are proteins that contain energy, which can be released during metabolism processes in an organism. Egg ovalbumin and milk casein are examples of such storage proteins.

Enzyme Factor VIIa is one of several coagulation protein that may be used to initiate the clotting cascade for uncontrollable bleeding, such as in patients affected with hemophilia or uncontrolled hemorrhage. It has been adminstered to soldiers at field hospitals to prevent blood loss by promoting coagulation.

Each of the herein described examples of proteins may be covalently attached to or modified with a plurality of thermally responsive polymer chains.

Biomolecules include the enzymes, proteins, biological catalysts, and antibodies, as described herein.

As used herein, "poly(N-isopropylacrylamide)" is identified by the abbreviations: "NiPAAm", "NiPAM", "nipam", "NiPAAM", "pNiPAAm", "pNiPAM", "PNIPAM", and "pNiPAAM". Poly(N-isopropylacrylamide) is the most preferred thermally responsive polymer employed in this invention.

The present invention provides a biomolecule comprising one functionalized biomolecule. Wherein, the biomolecule is functionalized with one or more sites and having at least one polymer chain having a first end and a second end. The first end of the chain is attached to the site on the functionalized biomolecule. The second end of the chain is free moving. The chain comprises one or more monomers, wherein at least one monomer is stimuli responsive. The chain collapses in response to the stimuli and envelopes the functionalized biomolecule to form a reversible nanoparticle structure. The chain is not cross-linked. Said polymers comprising the polymer chain may be the same polymer.

The present invention provides a biomolecule conjugate comprising one or more functionalized biomolecules, the biomolecule is functionalized with one or more sites, and at least one polymer capable of undergoing a polymer growth reaction, wherein the polymer is attached to at least one of the sites of the functionalized biomolecule and wherein the polymer envelopes the functionalized biomolecule to form a reversible nanoparticle structure. In another embodiment of this invention, as described herein, the biomolecule conjugate includes wherein the functionalized biomolecule is freely mobilized within the reversible nanoparticle structure. In a preferred embodiment of this invention, the biomolecule conjugate, as described herein, includes wherein the nanoparticle structure has a diameter between 5 nanometers and 1000 nanometers. Another embodiment of the biomolecule conjugate of this invention, as described herein includes wherein the functionalized biomolecule is one or more enzymes, proteins, antibodies, or biological catalysts. Preferably, the enzyme, protein, or biological catalyst remains in a folded conformation and retains high degrees of catalytic activity within the nanoparticle structure.

Another embodiment of the biomolecule conjugate of this invention, as described herein, includes wherein the biomolecule is functionalized with a site that is at least one of the moieties selected from a group consisting of an amine, a carboxylate, a hydroxyl, a lysine residue, a vinyl group, and a thiol group.

In another embodiment of this invention, the biomolecule conjugate, as described herein, includes wherein the biomolecule is an enzyme wherein the enzyme retains activity ranging from 5 to 100% of the enzyme's native catalytic activity.

Preferably, in another embodiment of this invention, the biomolecule conjugate is a polymer that comprises one or more thermally responsive polymers which undergo a transition from having a hydrophilic character to having a hydrophobic character above a specific lower critical solution temperature. More preferably, the biomolecule conjugate, as described herein, includes wherein the thermally responsive polymer is collapsible as an environmental temperature rises and the enzyme remains highly folded and in an un-denatured state.

In another embodiment of this invention, the biomolecule conjugate, as described herein, includes wherein the nanoparticle structure comprises one or more of a fully or of a partially thermally responsive polymer.

Another embodiment of this invention provides the biomolecule conjugate of this invention, as described herein, wherein the thermally responsive polymer is a polymer selected from the group consisting of a poly(N-isopropylacrylamide), a poly(isopropyl-N-vinylpyrrolidone), or any polymer which undergoes a conformational change when heated, and combinations thereof.

Other embodiments of the biomolecule conjugate of this invention include wherein the biomolecule conjugate, as described herein, (i) has improved stability over a native biomolecule at temperatures greater than 30 degrees Centigrade in both aqueous solutions and dry powders, (ii) is a functionalized biomolecule that is stable at temperatures ranging from zero degrees Centigrade to 30 degrees Centigrade, and (iii) includes a protein is stable at temperatures greater than 30 degrees Centigrade, and (iv) combinations of (i)-(iii).

In another embodiment of the biomolecule conjugate of this invention, as described herein, includes wherein the enzymes are selected from the group consisting of lyases, hydrolases, oxidoreductases, transferases, isomerases, and ligases, and combinations thereof. Preferably, the enzymes are selected from the group consisting of a hydrolase, a lipase, a phosphatase, an amylase, a cellulase, a protease, a peptidase, a urease, carbonic anhydrase, and a deaminase, a transaminase, a deiminase, a ketoreductase, a haloperoxidase, and combinations thereof. More preferably, the enzymes are selected from the group consisting of organophosphorus hydrolase (OPH), organophosphorus acid anhydrolase (OPAA), butyrylcholinesterase, glucose oxidase (GOx), acetylcholinesterase (AChe), dehalogenase (DHG), diisopropylfluorophosphatase (DFPase), and Factor VIIa.

Another embodiment of the biomolecule conjugate of the present invention, as described herein, include wherein the enzymes are incapable of unfolding or are retarded from unfolding under stressful environmental conditions. The stressful condition is, for example but not limited to, a temperature greater than 30 degrees Centigrade.

Another embodiment of this invention provides a method for protecting a biomolecule from environmental conditions comprising functionalizing one or more biomolecules by adding one or more reactive sites to a surface of the biomolecule to form a functionalized biomolecule, attaching at least one polymer to at least one of the reactive sites of the functionalized biomolecule, surrounding the functionalized biomolecule with the polymer to form a reversible nanoparticle structure; and optionally growing the polymer directly from the surface of the functionalized biomolecule, for protecting the biomolecule from environmental conditions. Preferably, this method includes wherein the biomolecule is at least one enzyme, protein, antibody, or biological catalyst. More preferably, this method includes wherein the biomolecule is an enzyme and the reactive site is an acrylate or vinyl group on the surface of the enzyme.

Another embodiment of the method of this invention, as described herein, includes growing the polymer using a controlled radical polymerization process.

Another embodiment of the method of this invention, as described herein, includes growing the polymer using a free-radical addition polymerization process or a living radical polymerization process. Preferably, the method includes wherein the controlled radical polymerization process is an atom transfer radical polymerization (ATRP). In another preferred embodiment, this method includes wherein the free-radical polymerization process optionally includes at least one thermally responsive comonomer selected from the group consisting of a N-isopropylacrylamide, poly(isopropyl-N-vinylpyrrolidone), a polymer which undergoes a conformational change when heated, and combinations thereof. Further, the method includes wehreing the controlled polymerization process is a reversible addition-fragmentation chain-transfer polymerization (RAFT).

It will be appreciated by those persons skilled in the art that the protein-polymer macromolecular nanoparticle of the present invention provides for a stimuli-responsive polymer covalently bound to a protein that has improved stability over a native protein in harsh environments, in both aqueous solutions and dry powders. The nanoparticle of the present invention has a stimuli-responsive polymer covalently bound protein that is stable at temperatures below 30 degrees Centigrade and is stable ranging from zero (0) degrees Centigrade to 30 degrees Centigrade. Further, the nanoparticle of the present invention has a protein polymer conjugate composition that is significantly more stable at temperatures greater than 30 degrees Centigrade than is the native protein.

Another embodiment of this invention provides a method for protecting proteins from environmental conditions by performing CRP on one or more proteins to covalently bind a responsive polymer for protecting the protein from detrimental environmental conditions.

Another embodiment of the invention provides functionalized enzyme conjugates that have enzymes that retain catalytic activity while attached to a responsive polymer. The enzyme is structurally supported via covalent bonds to polymers and is further structurally supported at elevated temperatures by the collapsing pNiPAAm polymer chains. The ability to maintain or enhance the stability of enzymes at high temperatures has significant application in the fields of industrial catalysis, decontamination, and field-portable diagnostics. pNiPAAm undergoes a volume transition at temperatures above its lower critical solution temperature (LCST), which is approximately 32° C. At temperatures <32° C. conjugates composed of pNiPAAm are hydrophilic and highly swollen, their apparent refractive index is similar to water and solutions containing these particles appear clear. Once heated above 32° C. the polymer chains become more hydrophobic and shrink in size, collapsing upon themselves and increasing their refractive index, causing the solution to appear turbid and resulting in dense nanoparticle-like enzyme-polymer conjugates. Given the ability to rapidly heat the solution, the response time is nearly instantaneous.

Temperature responsive polymers or otherwise known as thermally responsive polymers undergo a phase transition behavior at temperatures above and below a specific value known as the lower critical solution temperature (LCST). At temperatures above the LCST, the hydrophobic bonds within and between the molecules strengthen and the polymer chains aggregate (the polymer becomes more hydrophobic) or adhere/adsorb more easily to surfaces and to polymers of like composition. Conversely, at temperatures lower than the LCST, the polymer chains bind to water molecules and become hydrated (the polymer is hydrophilic). This phase transition phenomenon is reversible. Thermally responsive polymers, as used herein, include such as for example, but not limited to, N-isopropylacrylamide, and most preferably poly(N-isopropylacrylamide) (NiPAAm/pNiPAAm/NiPAM/pNiPAM), and are the most studied thermally responsive (thermo-responsive) polymers and are utilized in this invention to fabricate the thermally responsive nanoparticles of the present invention. Additionally, it will be appreciated by those skilled in the art, that other thermally responsive polymers can be employed in the methods and nanoparticles of the present invention, such as but not limited to: N-vinylpyrrolidone, N-acryloypyrrolidine, N-acryloyl piperidine, N-vinylisobutyramide, MA-PIPA, methylenebisacrylamide, N-isopropylmethacrylamide, and N-diethylacrylamide, to name a few, as well as polymers synthesized to exhibit thermally responsive behavior, such as for example but not limited to, N-substituted poly[(meth)acrylamide]s, poly(N-vinylamide)s, poly(vinylpyrrolidone)s, poly(oxazoline)s, protein-related polymers, poly(ether)s, polymers based on amphiphilic balance and elastin-like synthetic polymers. Additionally, thermally responsive polymers based on alkyl modified poly-vinylpyrrolidone (PVP) can be employed in the present invention to produce thermo-responsive nanoparticle, such as for example but not limited to, poly-3-ethyl-1-vinyl-2-pyrrolidone (C2-PVP) and poly-3-butyl-1-vinyl-2-pyrrolidone (C4-PVP). Further examples of polymers that could be used include but are not limited to Poly(N-ethylacrylamide), poly(N-ethylmethylacrylamide), poly(N,N'-ethylacrylamide), poly(N,N'-diethylacrylamide), poly(N-n-propylacrylamide), poly(N-n-propylmethacrylamide), poly(N-isopropylmethacrylamide), poly(N-cyclopropylacrylamide), poly(N-(L)-(1-hydroxylmethyl)propylmethacrylamide), poly(N-acryloylpyrrolidine), poly(N-acryloylpiperidine), poly(N-vinyl caprolactam), poly(N-vinyl propylacetamide), poly(N-vinyl-5-methyl-2-oxazolidione), poly(N-vinyl isobutyramide), poly(L-proline), poly(N-acryloyl-L-Proline methyl ester), poly(N-acryloyl-4-trans-hydroxy-L-proline methyl ester), poly(methyl 2-alkylamidoacrylate), poly(methyl 2-propionamidoacrylate), poly(methyl 2-isobutyracrylate), poly(2-methyl-2-oxazoline), poly(2-n-propyl-2-oxazoline), poly(2-isopropyl-2-oxazoline), poly(ethyleneoxide), poly(propyleneoxide), poly(methylvinylether), poly(2-methoxyethylvinylether), poly(2-ethoxyethylvinylether), poly(2-(2-ethoxy)ethoxyethylvinylether), poly(4-hydrobutylvinylether), poly(methyl glycidyl ether), poly(2-methoxy-2-oxo-1,3,2-dioxaphospholane), poly(2-ethoxy-2-oxo-1,3,2-dioxaphospholane), poly(2-isopropoxy-2-oxo-1,3,2-dioxaphospholane), poly(methylacrylamide), poly(N,N'-dimethylacrylamide), poly(vinylpyrrolidone), poly(acryloylmorpholine), poly(N-tert-butylacrylamide), poly(2-ethyl-2-oxaline)-block-poly(ε-caprolactone), poly(vinylalcohol), poly(vinylacetate), poly(ethyleneoxide), poly(propyleneoxide), poly[2-(2-ethoxyethoxy)ethylacrylate], poly[2-(2-methoxyethoxy)ethylmethacrylate)], poly(2-[2-(2-methoxyethoxy)ethylmethacrylate), poly[oligo(ethyleneglycol)methacrylate], poly(2-hydroxylpropylacrylate), poly(2-hydroxyethylmethacrylate), poly(amidohydroxyurethane), 1,4butanediol diglycidyl ether, poly(organophosphazene), poly[6-(acryloyloxymethyl)uracil], poly(ethyleneoxide), poly(methacrylamide), poly(vinyl alcohol), poly(vinyl acetate) and poly(N-methacrylylglycinamide). These polymers exhibit very sensitive reversible temperature-dependent water solubility and the LCST can be tuned by modification of the alkyl group.

Additional hydrophobic monomers such as styrene, can be used as comonomers u in the present invention to enhance the hydrophobic interaction of the thermo-responsive polymer—essentially making the nanoparticles prone to collapse upon themselves and effectively shrink more when the LCST is exceeded. Additional hydrophobic comonomers can be substituted for styrene in the method for the enzyme-friendly nanoparticle synthesis of the present invention such as for example but not limited to, Butyl methacrylate, 1,3-Butadiene, Poly(styrene-co-4-vinylpyridine), and Benzocyclobutene, poly(butyl acrylate-styrene).

With regard to the initiators of the polymerization reaction, an initiator is used in the present invention to assist in the polymerization process during nanoparticle synthesis. N-hydroxy-Succinimidyl-TEG-Br (NHS-TEG-BR) is the most preferable initiator described in this method for enzyme-friendly nanoparticle synthesis, however, additional initiators can be substituted in the reaction. For example additional initiators are but no limited to, R-halo ester based chemical compounds such as succinimidyl-TEG-Br, R-halo amide based chemical compounds such as N,N-dimethyl-2-bromopropianamide and maleimide functionalized initiators.

The current invention encompasses polymeric responses to pH, temperature, Ionic strength, water hardness, light, solvent, oxidative environment, anaerobic environment, radiation, pressure, osmotic strength and magnetism depending on the type of responsive polymers covalently attached to it the enzyme. Further additional polymers could be added to make the molecule resistant to bacteria or have better retention in the blood.

The current invention creates responsive nanoparticles with individual enzyme/protein cores which said nanoparticles are able to achieve sizes as low as 5 nanometers in diameter, which is below what is achievable using free radical polymerization of organically based (carbon-containing) monomers and polymers according to the methods of Walker et al. These nanoparticles can be from 5 nm to 1000 nm in size, more preferably 5 nm to 200 nm, even more preferably 5 nm to 25 nm. The ratio of polymer to protein can be significantly smaller than prior art due to the ability of tuning the reaction via a CRP process or by using sufficiently small grafts. There is a higher degree of flexibility since the molecule is not hindered by cross-links. However, cross-links can be added if desired to make the structure more rigid, especially once the thermally responsive polymer is collapsed, thereby locking the polymer in place. Any CRP method such as ATRP, RAFT, Stable Free Radical mediated polymerization (SFRP), etc. can be used for covalently attaching the polymer. The CRP process is an improvement over prior art since other methods involve extensive clean-up of the final product due to unreacted monomer. A further embodiment has two or more polymers attached to the biomolecule wherein each polymer is responsive different stimuli. This gives the molecule dual purpose such as retention in the blood and protection against elevated temperatures.

A further embodiment can be responsive to ionic strength. Partially hydrolyzed Polyacrylamide (Hydrolyzed Polyacrylamide)HPAM is a polymer widely used for Enhanced Oil Recovery applications. High molecular weight HPAM produces a high viscosity even at low concentrations. The viscosity of HPAM is sensitive to salinity and hardness. As salinity and hardness increase, the viscosity of HPAM solution decreases rapidly. (Arifin, "Synthesis of Polymer with High Salinity and Mechanical Stability Based on Cellulosic Polymer" IPA, 2012 $35^{th}$ Annual Convention Proceedings)

A further embodiment can use a photosensitizer-protein conjugate. Illumination with appropriate wavelength light allows one to switch on or off a polymer. In the case of Rose Bengal (RB) dye and Bovine Serum Albumin (RB-BSA) complexes, one can turn on the production of reactive oxygen species (ROS) with illumination. These conjugates can be used to induce "cell-death" on demand. BSA is known to be stable and favors a hydrophobic interaction with RB. In addition, the conjugation of RB to BSA avoids interaction with the polymer membrane due to the hydrophilic character of BSA. These conjugates can be permeable to ROS, while holding onto the photosensitizer. These conjugates further allow detection associated with the fluorescent signal of the photosensitizer and treatment by generation of ROS. However, some light sensitive molecules are inherently toxic. This toxicity can be reduced by further addition of other polymers to reduce this toxicity and to stabilize the photosensitizer. (Baumann "Light-responsive polymer nanoreactors: a source of reactive oxygen species on demand" Nanoscale, 2013, 5, 217)

Further embodiments can use polymers that are responsive to stimuli such as solvent, oxidative environment, anaerobic environment, radiation, pressure, osmotic strength or magnetism. Additional polymers could be added to make the molecule resistant to bacteria or have better retention in the blood. Polymer blocks can be created for additional functionalities. PEG can be used where biocompatibility, meaning reduced immunogenicity, is required. Primary amines can be easily used for covalent attachment of the polymer to a protein.

Another embodiment of the present invention provides a sensor having a biomolecule conjugate comprising one functionalized biomolecule. Wherein, the biomolecule is functionalized with one or more sites and having at least one polymer chain having a first end and a second end. The first end of the chain is attached to the site on the functionalized biomolecule. The second end of the chain is free moving. The chain comprises at least two polymers, wherein at least one polymer is stimulus responsive. The chain collapses in response to the stimuli and envelopes the functionalized biomolecule to form a reversible nanoparticle structure. The chain is not cross-linked.

Another embodiment of the present invention provides a sensor having a biomolecule conjugate comprising one or more functionalized biomolecules, wherein the biomolecule is functionalized with one or more sites, and at least one polymer capable of undergoing a polymer growth reaction, wherein the polymer is attached to at least one of the sites of the functionalized biomolecule and wherein the polymer envelopes (surrounds) the functionalized biomolecule to form a reversible nanoparticle structure. Preferably, the biomolecule conjugate, as described herein, of the sensor of the present invention, includes wherein the functionalized biomolecule is freely mobilized within the reversible nanoparticle structure. Another embodiment of this invention provides wherein the sensor has a biomolecule conjugate, as described herein, that includes wherein the nanoparticle structure has a diameter between 5 nanometers and 1000 nanometers.

Another embodiment provides a sensor wherein the functionalized biomolecule is one or more enzymes, proteins, antibodies, or biological catalysts.

Another embodiment provides a thermally responsive polymer selected from the group consisting of a poly(N-isopropylacrylamide), a poly(isopropyl-N-vinylpyrrolidone), a polymer which undergoes a conformational change when heated, and combinations thereof.

Another embodiment provides a sensor that has improved stability over a native biomolecule at temperatures greater than 30 degrees Centigrade in both aqueous solutions and dry powders.

Another embodiment provides a sensor wherein the enzymes are selected from the group consisting of organophosphorus hydrolase (OPH), organophosphorus acid anhydrolase (OPAA), butyrylcholinesterase, glucose oxidase (GOx), acetylcholinesterase (AChe), dehalogenase (DHG), diisopropylfluorophosphatase (DFPase), and Factor VIIa.

Another embodiment provides a sensor including a glucose sensing element with enhanced thermal stability. Another embodiment provides a sensor wherein the glucose sensing element comprises a GOX containing hydrogel.

Another embodiment provides a method for manufacturing a sensor comprising providing a housing for a sensor. Then providing a biomolecule on or within said housing of said sensor and protecting said biomolecule from environmental conditions comprising functionalizing one or more of said biomolecules by adding one or more reactive sites to a surface of said biomolecule to form a functionalized biomolecule and attaching at least one polymer to at least one of said reactive sites of said functionalized biomolecule surrounding said functionalized biomolecule with said polymer to form a reversible nanoparticle structure; and optionally growing said polymer directly from said surface of said functionalized biomolecule, for protecting said biomolecule from environmental conditions, for manufacturing said sensor. Additionally the present invention may include wherein said biomolecule is at least one enzyme, protein, antibody, or biological catalyst. The present invention may additionally include the method wherein the thermally responsive polymer is selected from the group consisting of a N-isopropylacrylamide, poly(isopropyl-N-vinylpyrrolidone), a polymer which undergoes a conformational change when heated, and combinations thereof. Additionally, the method may include wherein said enzyme is glucose oxidase (GOX) for providing a glucose sensing element. Further the method may include wherein said glucose sensing element comprises a GOX containing hydrogel.

Current biomolecule components in many diagnostic sensors (colorimetric, amperometric, potentiometric, affinity-based assays or sensors) are the limiting component in the life of the sensor. These sensors use biomolecules such enzymes, antibodies, hormone binding receptors, oligopeptides, and a variety of others. The state of the art in covalent immobilization is graft modification of a polymerizable group or immobilization via aldehyde cross-linking. Each of these methods result in a highly adverse impact to the activity of the embedded biomolecule (i.e. reduced activity of the enzyme or reduced avidity of the antibody) due to over modification, intramolecular cross-linking, blocking of the biomolecule's active site, forced denaturation upon immobilization, or insufficient three-dimensional covalent binding to retain active three dimensional folding conformations.

Temperature fluctuations limit the shelf-life of current sensors. The lack of an element in existing sensors to protect against increases in temperature results in denaturation of the embedded or attached biomolecules. The present invention relates a material composition that enhances the stability of biomolecules in sensors and diagnostic devices by functionalizing them with an environmentally-responsive polymer that stabilizes the biomolecules in response to adverse environmental conditions, such as but not limited to high temperature, via a particle shell forming collapse that prevents the enzyme from denaturing. This nanoparticle-shell provides a semi-rigid polymer scaffold that structurally supports and maintains the interior enzymes' tertiary structure.

This invention provides a biomolecule conjugate comprising one functionalized biomolecule, said biomolecule is functionalized with one or more sites; at least one polymer chain having a first end and a second end; said first end of said chain is attached to said site on said functionalized biomolecule; said second end of said chain is free moving; said chain comprises at least two polymers, wherein at least one polymer is stimuli responsive, wherein said chain collapses in response to said stimuli and envelopes said functionalized biomolecule to form a reversible nanoparticle structure; and wherein said chain is not cross-linked. Further, the invention, as described herein provides the biomolecule conjugate wherein said functionalized biomolecule is one or more enzymes, proteins, antibodies, or biological catalysts. The biomolecule conjugate preferably is said enzyme, protein, or biological catalyst that remains in a folded position and retains active conformation within said nanoparticle structure. Further, the biomolecule conjugate includes wherein said biomolecule is functionalized with a site that is at least one of the moieties selected from a group consisting of an amine, a carboxylate, a vicinal diol, a lysine residue, a vinyl group, and a thiol group. Further, the biomolecule conjugate of this invention includes wherein said polymer is thermally responsive and preferably is selected from the group consisting of a poly(N-isopropylacrylamide), a poly(isopropyl-N-vinylpyrrolidone), a polymer which undergoes a conformational change when heated, and combinations thereof. The biomolecule conjugate has improved stability over a native biomolecule at temperatures greater than 30 degrees Centigrade in both aqueous solutions and dry powders. The biomolecule conjugate that is an enzyme selected from the group consisting of organophosphorus hydrolase (OPH), organophosphorus acid anhydrolase (OPAA), butyrylcholinesterase, glucose oxidase (GOx), acetylcholinesterase (AChE), dehalogenase (DHG), diisopropylfluorophosphatase (DFPase), chloroperoxidase, lipase and urease.

Another embodiment of this invention provides a sensor comprising one functionalized biomolecule, said biomolecule is functionalized with one or more sites; at least one polymer chain having a first end and a second end; said first end of said chain is attached to said site on said functionalized biomolecule; said second end of said chain is free moving; said chain comprises at least two polymers, wherein at least one polymer is stimuli responsive, wherein said chain collapses in response to said stimuli and envelopes said functionalized biomolecule to form a reversible nanoparticle structure; and wherein said chain is not cross-linked. Further this invention provides wherein the sensor, as described herein, includes wherein said functionalized biomolecule is one or more enzymes, proteins, antibodies, or biological catalysts. The sensor of includes said thermally responsive polymer that is preferably a polymer selected from the group consisting of a poly(N-isopropylacrylamide), a poly(isopropyl-N-vinylpyrrolidone), a polymer which undergoes a conformational change when heated, and combinations thereof. The sensor of this invention has improved stability over a native biomolecule at temperatures greater than 30 degrees Centigrade in both aqueous solutions and dry powders. The sensor of this invention includes wherein said enzymes are selected from the group consisting of organophosphorus hydrolase (OPH), organophosphorus acid anhydrolase (OPAA), butyrylcholinesterase, glucose oxidase (GOx), acetylcholinesterase (AChe), dehalogenase (DHG), diisopropylfluorophosphatase (DFPase), urease, chloroperoxidase and Factor VIIa. In a more preferred embodiment of this invention, the sensor, as described herein, includes a glucose sensing element with enhanced thermal stability. This sensor most preferably has a glucose sensing element that comprises a GOX containing hydrogel.

Another embodiment of this invention provides a method for manufacturing a sensor comprising providing a housing for a sensor; providing a biomolecule on or within said housing of said sensor; protecting said biomolecule from environmental conditions comprising functionalizing one or more of said biomolecules by adding one or more reactive sites to a surface of said biomolecule to form a functionalized biomolecule; attaching at least one polymer to at least one of said reactive sites of said functionalized biomolecule; surrounding said functionalized biomolecule with said polymer to form a reversible nanoparticle structure; and optionally growing said polymer directly from said surface of said functionalized biomolecule, for protecting said biomolecule from environmental conditions, for manufacturing said sensor. This method includes wherein said biomolecule is at least one enzyme, protein, antibody, or biological catalyst. The method includes wherein said thermally responsive is preferably selected from the group consisting of a N-isopropylacrylamide, poly(isopropyl-N-vinylpyrrolidone), a polymer which undergoes a conformational change when heated, and combinations thereof. Most preferably, this method includes providing said enzyme that is glucose oxidase (GOX) for providing a glucose sensing element. The method includes providing wherein said glucose sensing element comprises a GOX containing hydrogel.

The invention specifically relates to use of a variety of polymers that demonstrate lower critical solution temperature (LCST) responses, and can be polymerized from the surface of the biomolecule under protein-friendly conditions (low temperature, aqueous buffered solution) via a number of controlled radical polymerization (CRP) processes, including, but not limited to atom transfer radical polymerization (ATRP), reversible addition-fragmentation chain transfer polymerization (RAFT), iodine transfer polymerization and anionic polymerization.

The invention further provides for the capability of the polymer chains to have multiple functionalities that enhance the performance of the biomolecule within the sensing element. This can include providing two or more polymer blocks to the chains that enable not only the protective thermal collapse that is outlined, but also additional functionalities. These additional functionalities can enable the resulting protein-polymer macromolecule to be covalently immobilized or to participate in a polymerization reaction resulting in the formation of a hydrogel, coating, film, or particle. Where the thermostabilized biomolecule is immobilized and can perform a sensing/response function as an element of the diagnostic sensor material. The secondary blocks may also provide functionality to improve the macromolecule's solubility in either polar organic or nonpolar organic solvents, or may serve to hold water close to the enzyme's core, such that it can be dispersed into a solvent but retain the hydration shell often necessary to produce the desired catalytic activity.

The modification of glucose oxidase (GOX) enzyme with a thermally responsive polymer material enhances stability and activity retention of GOX in aqueous storage conditions at elevated temperatures compared with the free native enzyme. The polymer-modified GOX demonstrates enhanced thermal stability when stored in the dry state. The enzyme can further be functionalized with a second polymer block containing a primary amine that enables it to be anchored to a particle resin via an epoxide ring opening reaction. The GOX-polymer complex can be further modified at the primary amine block to graft a succinimidyl ester of an acrylate to contain enable it to be polymerized in a secondary polymerization within a polymeric hydrogel, coating, or film material. The hydrogel, coating or film with the embedded GOX-polymer material demonstrates superior retention of catalytic activity in an aqueous environment at a variety of elevated temperatures ranging from 25° C. to 60° C. compared with GOX that has been graft modified with only acrylate moieties and polymerized within a hydrogel, coating or film of identical polymer composition.

The same technology can be applied to additional enzymes such as lactate oxidase, creatinine amidinohydrolase, creatine aminohydrolase, urease, and any enzyme which may be used as an element in a sensor or diagnostic device or assay. Additionally, it can be applied to antibodies, hormone binding receptors, G-protein coupled receptors, gamma amino butyric acid (GABA) receptors, and other biological molecules that are components in ELISA (enzyme linked immunosorbent assay) immunoassays, lateral flow assays, binding assays, or other diagnostic assays.

"Room Temperature" is defined as temperatures between 18° C. and 28° C.

EXAMPLE 1

Attachment of pNiPAAm to OPH Via a Modified ATRP Reaction

Organophosphorus hydrolase (OPH, EC 3.1.8.1) (Lybradyn, Inc, Oak Brook, Ill.) hydrolyzes organophosphorus nerve agents and pesticides; it is used as a decontamination enzyme for remediation of organophosphorus (OP) pesticides and nerve agents as well as used as a medical countermeasure for OP poisoning. OPH from *Geobacillus* is 37.2 kD protein that contains 8 lysine residues and is a homodimer. The ability to stabilize OPH at elevated temperatures could be useful for many areas including but not limited to: chemical remediation, detection and decontamination and prophylaxis. ATRP is a process known by those persons skilled in the art. Poly(N-isopropylacrylamide) (pNIPAM) is a thermally-responsive polymer which undergoes a volume transition at temperatures above its lower critical solution temperature (LCST) which is approximately 32° C. At temperatures less than 32° C., conjugates composed of NiPAAm are hydrophilic and highly swollen. Once heated above 32° C. the particles become more hydrophobic and shrink in size, collapsing upon themselves (become nanoparticles). Given the ability to rapidly heat the solution, the response time is nearly instantaneous.

Succinimidyl-TEG-Br 1-(2,5-Dioxopyrrolidin-1-yloxy)-1-oxo-2,5,8,11-tetraoxatridecan-13-yl-α-bromo-2-isobutyrate (NHS-TEG-Br) ATRP initiator (ATRP Solutions, Pittsburgh, Pa.) was used to first modify OPH via the surface lysine amines. Ninety-three micrograms of NHS-TEG-Br was added for every 1 mg of OPH in an aqueous buffered system (50 mM Borate pH 8.0, 16% v/v DMSO). The reaction was stirred for 1 hour at +4° C. Excess NHS-TEG-Br was removed by ultrafiltraion in a 50 mL Millipore stirred cell with a 10,000 molecular weight cut off (MWCO) filter installed. The outflow of the filtered cell was monitored by UV 260 for complete removal of excess initiator. Concurrently, the buffer was exchanged to 15 mM Tris HCl, pH 7.6, and the protein was concentrated to greater than 2.5 mg/mL.

The OPH-TEG-Br (OPH-Br) conjugate was then modified with pNIPAAm via ATRP. Twenty eight milligrams of OPH-Br was combined with 46 mg of pNIPAAm in a 25 mL Schlenk flask and deoxygenated. A solution containing 3.49 mg CuCl, 4.68 mg 2,2'-Bipyridyl, and 1.07 mg CuCl2 was then made under deoxygenated conditions. This solution was then charged into the deoxygenated Schlenk flask and the reaction was allowed to progress with stirring for 1 hour at +4° C.

The full reaction was transferred to a millipore stirred cell with a 30,000 MWCO filter installed. The outflow of the filtered cell was monitored by UV 260 for complete removal of the reaction components. The OPH-pNIPAAm conjugate was then modified with Poly(ethylene glycol) methyl ether methacrylate (average molecular weight 475) (PEGMA475) via ATRP. 28 mg of OPH-Br was combined with a final concentration of 16.6% v/v PEGMA475 in a 25 mL Schlenk flask and deoxygenated. A solution containing 3.49 mg CuCl, 4.68 mg 2,2'-Bipyridyl, and 1.07 mg CuCl$_2$ was then made under deoxygenated conditions. This solution was then charged into the deoxygenated Schlenk flask and the reaction was allowed to progress for 1 hour at +4° C.

Figure 16:
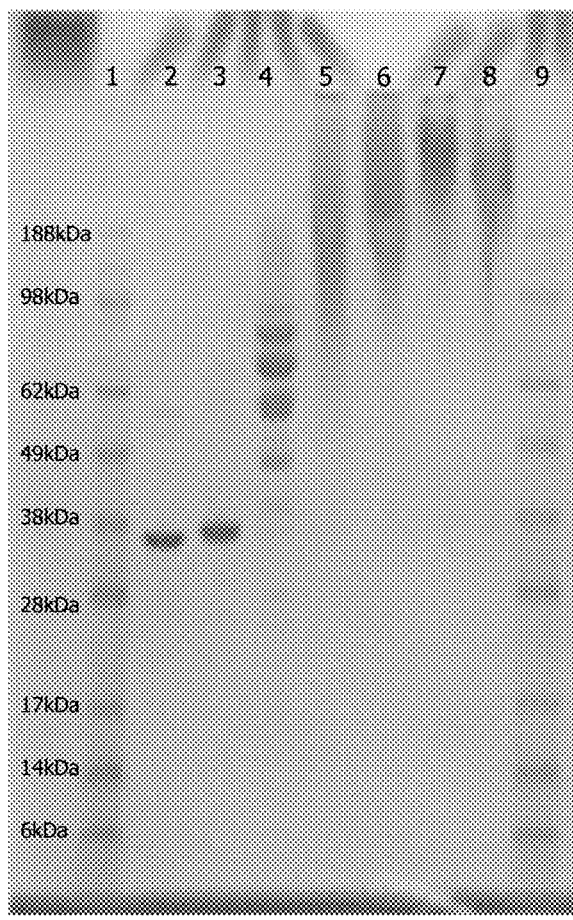
FIG. 16 is an SDS-PAGE gel of unmodified and modified OPH. Lane 1 a molecular weight marker (Life technologies LC5925). Lane 2 has native OPH. Lane 3 has OPH that has a succinimidyl tetraethylene glycol (NHS-TEG-Br) initiator added. Lane 4 has OPH which has been GRAFT modified with an n-hydroxysuccinimidyl ester of PEG (Lysan mPEG-SS-5k). Lane 5 has OPH which has been ATRP modified with 3.3% PEGMA475 (Sigma). Lane 6 has been ATRP modified with 6.6% PEGMA475 (Sigma). Lane 7 has OPH which has been ATRP modified with 16.6% PEGMA475 (Sigma). Lane 8 has OPH that has been ATRP modified first with 16.6 mg/mL of NiPAAm, then with PEGMA 475. Lane 9 contains protein molecular weight marker (Life technologies LC5925).
Figure 17:
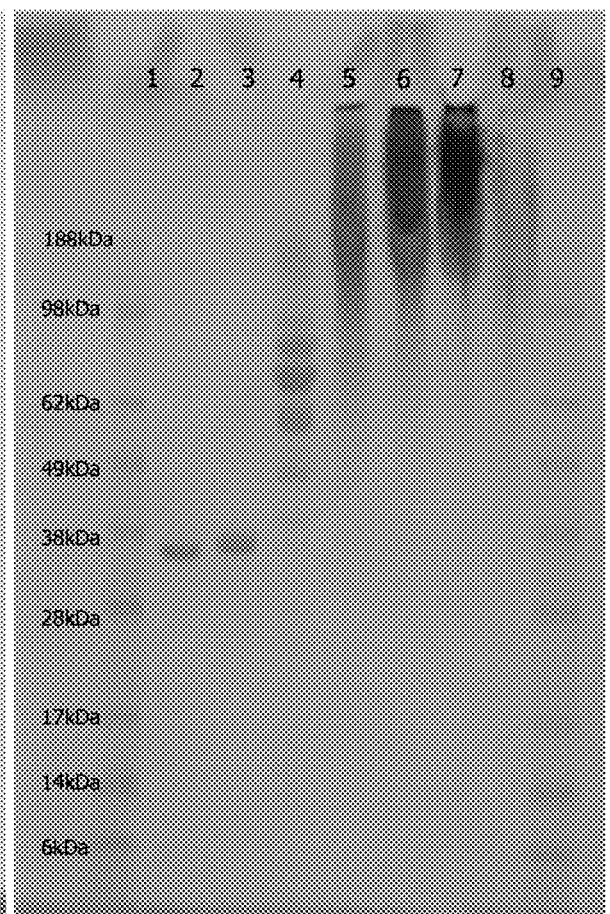
FIG. 17 is an SDS-PAGE gel of unmodified and polymer-modified OPH from FIG. 16. The gel was further stained with Barium Iodine, which will selectively stain PEG. Lane 1 a molecular weight marker (Life technologies LC5925). Lane 2 has native OPH (USAMRICD). Lane 3 has OPH that has NHS-TEG-Br added. Lane 4 has OPH which has been GRAFT modified with PEG (Lysan mPEG-SS-5k). Lane 5 has OPH which has been ATRP modified with 3.3% PEGMA475 (Sigma). Lane 6 has been ATRP modified with 6.6% PEGMA475 (Sigma). Lane 7 has OPH which has been ATRP modified with 16.6% PEGMA475 (Sigma). Lane 8 has OPH that has been ATRP modified with block copolymers, first with 16.6 mg/mL of NiPAAm, then with PEGMA 475. Lane 9 contains molecular weight marker (Life technologies LC5925).

The OPH conjugates were compared to native OPH by Sodium Dodecyl Sulfate Polyacrylamide Gel Electrophoresis (SDS-PAGE) after each modification step to determine the extent of modification (FIGS. 16 and 17). The larger the amount of PEGMA475 that was added the further the modification of the OPH (longer polymer chain growth). This is shown by the stains reluctance to move through the gel. The spot will stay towards the higher molecular weight markers. Further in FIG. 19 the Barium Iodine stain shows that it is indeed PEGMA475 that is bound to the OPH-pNiPAAm conjugate. As the OPH-pNiPAAm conjugate by itself does not stain red. Enzymes were also assayed post-modification to determine the amount of remaining catalytic activity.

Catalytic activity was measured throughout the modification and nanoparticle fabrication process to ensure that no step caused a significant loss in activity. FIG. 1 shows the standard assay for OPH. Organophosphorus hydrolase was assayed in a 96-well micro plate using a buffered medium (10 mM NaPO4, pH 7.0) supplemented with the pesticide paraoxon (5 mM). OPH catalyzes the hydrolysis of paraoxon. OPH activity was assayed at room temperature by determining the increase of p-nitrophenol concentration in the presence of excess paraoxon. For each mole of paraoxon degraded, a mole of p-nitrophenol and a mole of phosphoric acid are produced. The rate of the reaction is directly proportional to the production of p-nitrophenol measured at 405 nm.

EXAMPLE 2

Attachment of pNiPAAm to Carbonic Anhydrase Via a Modified ATRP Reaction

N-hydroxy-Succinimidyl-TEG-Br (NHS-TEG-Br) ATRP initiator (ATRP Solutions, Pittsburgh, Pa.) was used to modify Carbonic Anhydrase (CA). Fifteen hundredths of a microgram of NHS-TEG-Br was added for every 1 mg of CA in an aqueous buffered system (50 mM Borate pH 8.0, 16% v/v DMSO). The reaction was stirred for 1 hour at 4° C. Excess NHS-TEG-Br was removed by ultrafiltration in a 50 mL Millipore stirred cell with a 10,000 molecular weight cut off (MWCO) filter installed. The outflow of the filtered cell was monitored by UV 260 for complete removal of excess initiator. Concurrently, the buffer was exchanged to 15 mM Tris HCl, pH 7.6, and the protein was concentrated to greater than 2.5 mg/mL.

The CA-TEG-Br (CA-Br) conjugate was then modified with poly(N-Isopropylacrylamide) (pNIPAAm) via ATRP. One milligram of CuBr was added to a 10 mL Schlenk flask and deoxygenated. 17.5 mg of CA-Br was combined with 150 mg of NIPAAm, 0.6 mg of CuCl2 and 2.29 mg of ME6TREN and deoxygenated. This solution was then charged into the Schlenk flask and the reaction was allowed to progress for 1 hour at +4° C.

Figure 2:
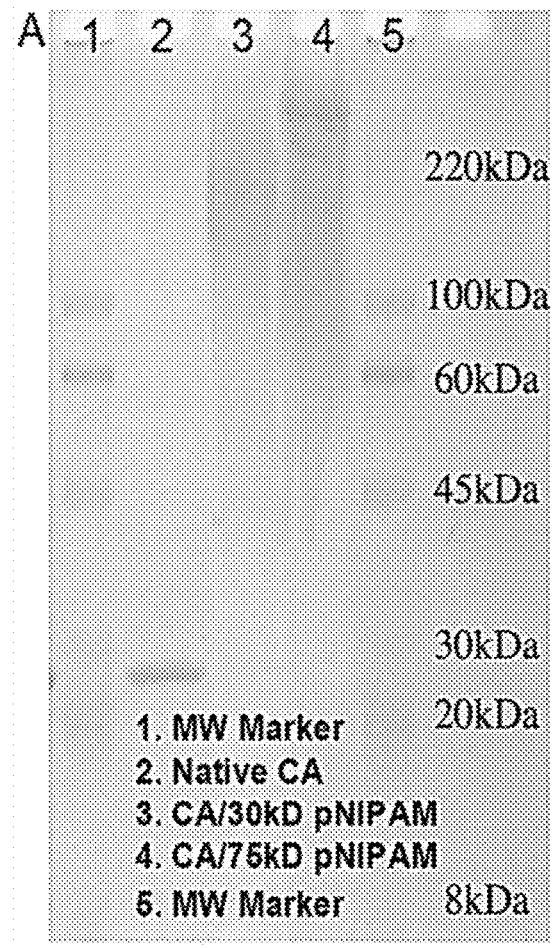
FIG. 2 is an SDS-PAGE gel of unmodified and modified Carbonic Anhydrase. Lane 1 and Lane 5 in the SDS-PAGE gel shown in FIG. 2 contain molecule weight markers (Sigma C1992, ColorBurst™ Electrophoresis Marker). Lane 2 shows the native unmodified Carbonic Anhydrase. Lane 3 shows Carbonic Anhydrase modified with a 30 kD pNiPAAm polymer. Lane 4 shows Carbonic Anhydrase modified with a 75 kD pNIPAAm polymer.

The CA conjugates were compared to native CA by Sodium Dodecyl Sulfate Polyacrylamide Gel Electrophoresis (SDS-PAGE) after each modification step to determine the extent of modification (FIG. 2). FIG. 2 demonstrates that the enzyme has indeed been modified. Lane 1 and Lane 5 in the SDS-PAGE gel shown in FIG. 2 contain molecule weight markers. Lane 2 shows the native unmodified Carbonic Anhydrase. Lane 3 shows Carbonic Anhydrase modified with a 30 kD pNIPAM polymer. Lane 4 shows Carbonic Anhydrase modified with a 75 kD pNIPAM polymer. FIG. 2 demonstrates that the native enzyme which is only 25 kD has been grown to 150 kD (30 kD polymer attachment) and 300 kD (75 kD polymer attachment) by adding a thermally responsive polymer to it via controlled radical polymerization.

Figure 3:
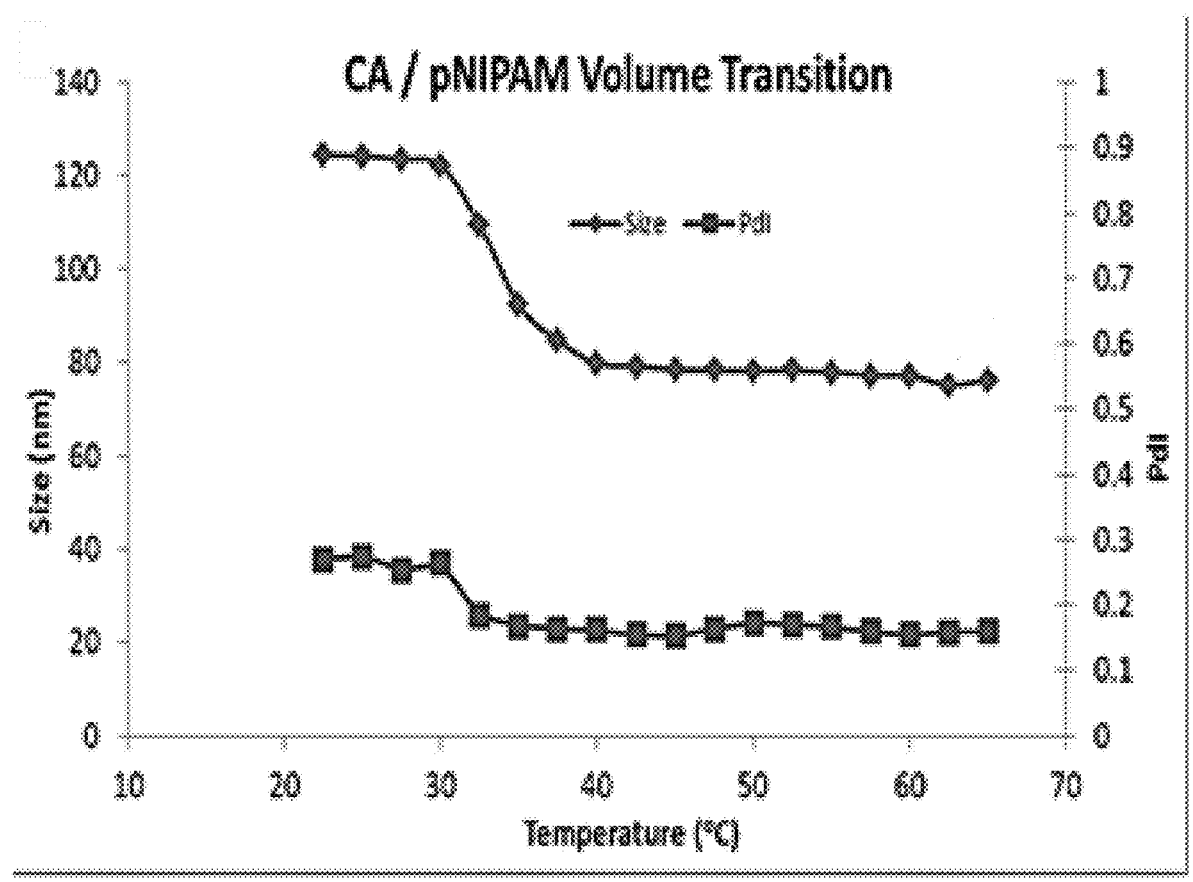
FIG. 3 is a plot of the DLS output of the Carbonic Anhydrase-pNiPAAm nanoparticles. It shows the DLS size readings (z-average) and the PDI (polydispersity index) that were taken at two and a half degree increments between 20° C. and 65° C.

Dynamic light scattering (DLS) was used to determine the size distribution of nanoparticles in solution. A Malvern Zetasizer Nano ZS was used to determine Carbonic Andrase-pNiPAAm nanoparticle size at various temperatures. The nanoparticles were diluted in filtered deionized water before nanoparticle diameter measurements were taken. FIG. 3 shows the DLS size readings that were taken at one degree increments between 20° C. and 65° C. The diameter of the nanoparticles shrunk by approximately 40% when the temperature increases above NiPAAm's LCST from approximately 125 nanometers (nm) at ambient temperatures to approximately 75 nm at elevated temperatures.

Figure 5:
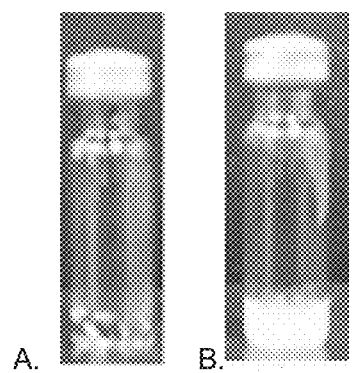
FIG. 5 (A) shows the Carbonic Anhydrase pNiPAAm Particles at 20° C.

This phenomenon can also be seen by viewing the solution. The enzyme is structurally supported via covalent conjugation and is further structurally supported at elevated temperatures by the collapsing pNiPAAm network. pNiPAAm undergoes a volume transition at temperatures above its lower critical solution temperature (LCST) approximately 32° C. At temperatures <32° C. nanoparticles composed of pNiPAAm is are hydrophilic and highly swollen, their refractive index is similar to water and solutions containing pNIPAM appear clear. Once heated above 32° C. the nanoparticles become more hydrophobic and decrease in size, NIPAM collapses upon itself and increases the refractive index mismatch, causing the solution to appear turbid. Given the ability to rapidly heat the solution, the response time is nearly instantaneous. FIG. 5 (A) shows the Carbonic Anhydrase Particles at 20° C. (below the LCST for pNiPAAm). FIG. 5 (B) shows the Carbonic Anhydrase Particles at 65° C. (above the LCST for pNiPAAm). The refractive index of the particles change when they shrink above the LCST for pNiPAAM and the solution becomes cloudy.

Figure 4:
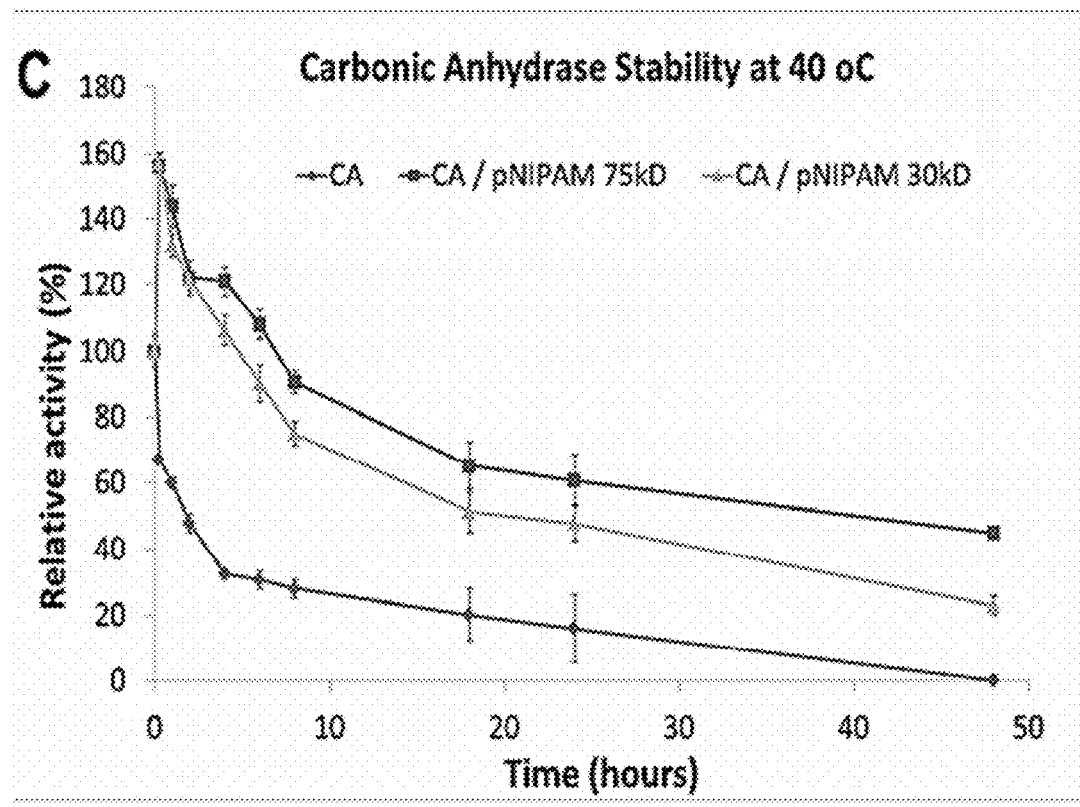
FIG. 4 is a plot of the enzyme catalytic activity of modified and unmodified Carbonic Anhydrase over time stored at 40° C.

Prior to incubation at elevated temperatures the catalytic activity was assayed; half-life of thermal inactivation is established when the samples lose 50% of their original activity. FIG. 4 shows the thermal half-life of inactivation in hours of CA nanoparticles and native unmodified CA. Through attachment of thermally-responsive nanoparticles of the present invention, CA samples increase their half-life from 2 hours to 45 hours (a 24.5-fold increase) at 40° C. Enzyme-pNiPAAm nanoparticles of the present invention retain a significantly higher degree of catalytic activity at elevated temperatures and have significantly longer half-lives. Contraction of particles at elevated temperatures increases thermal pot life (aqueous) stability. An antibody is a protein that can be stabilized through polymerization or covalent attachment of stimuli-responsive polymers. Antibodies are relatively fragile and tend to be unstable outside of controlled storage conditions (4° C.). Through conjugation with stimuli-responsive polymers as described in examples 1, 2 and 3, thermal stability can be drastically improved. The present invention does not fully encapsulate the antibody: therefore antigen binding to the antibody is not hindered. The resulting antibody nanoparticle will be fully functional in a variety of environments including but not limited to temperatures outside its normal storage condition. A further embodiment would polymerize thermally responsive polymer chains from the vicinal diols on sugars attached to the Fc region of an IgG antibody. The molecular crowding effect of the polymer growth enables retention of the tertiary structure by the antibody and improves binding of the antigen after thermal aging.

EXAMPLE 3

Attachment of pNiPAAm to Lipase Via a Modified ATRP Reaction

Lipase catalyzes the hydrolysis of lipids. In particular, lipases offers excellent stereospecificity of end products, thus the enzyme has significant potential for pharmaceutical synthesis and industrial biocatalysts. Lipase is by volume the most used enzyme in the world.

Figure 6:
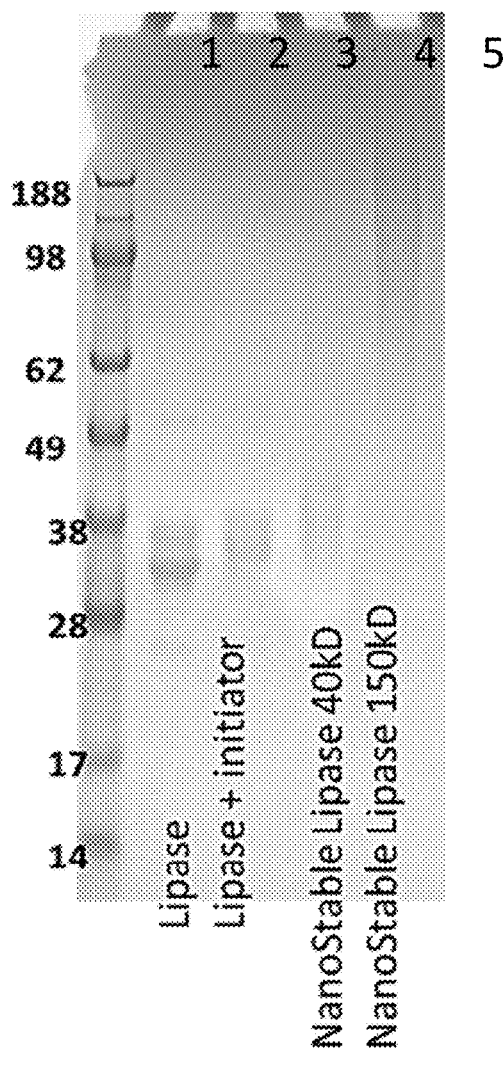
FIG. 6 is an SDS-PAGE gel of unmodified and modified Lipase. Lane 1 in the SDS-PAGE gel shown in FIG. 6 contains a molecule weight marker (See Blue Plus2 Pre-Stained Standard, Novex). Lane 2 shows the native unmodified Lipase (MW 33 kD). Lane 3 shows Lipase modified with a small molecule polymerization initiator. Lane 4 shows Lipase modified with a 40 kD pNiPAAm polymer. Lane 5 shows Lipase modified with a 150 kD pNIPAAm polymer.
Figure 7:
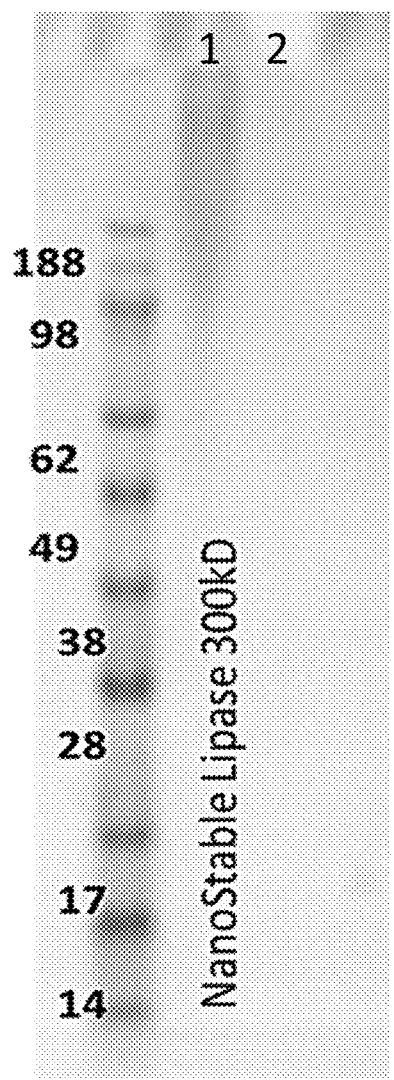
FIG. 7 is an SDS-PAGE gel of unmodified and modified Lipase. Lane 1 in the SDS-PAGE gel shown in FIG. 7 contains molecule weight markers (See Blue Plus2 Pre-Stained Standard, Novex). Lane 2 shows Lipase modified to 300 kD with a pNiPAAm polymer.

Lipase from *Aspergillus oryzae* (E.C. 3.1.1.3) (Novozymes, Denmark) with a molecular weight (MW) of 33 kD was modified with pNiPAAm through ATRP as described in examples 1 and 2. pNIPAM was polymerized from Lipase to increase its MW by 1.25×, 5× and 10× to 40 kD, 150 kD or 300 kD, respectfully. The resulting NanoStable Lipase conjugates were analyzed for MW and size increase via SDS-PAGE. Native Lipase, Lipase with initiator attached and Lipase post ATRP were evaluated by SDS-PAGE determine the extent of modification and size increase (FIGS. 6 and 7). Lane 1 in the SDS-PAGE gel shown in FIGS. 6 and 7 contains molecule weight markers. In FIG. 6, lane 2 shows the native unmodified Lipase, Lane 3 shows Lipase-TEG-Br showing the initiator has been conjugated to the protein prior to ATRP. Lane 4 shows Lipase polymerized with pNIPAM to a MW of 40 kD and 150 kD, Lane 5. In FIG. 7, Lane 2 shows Lipase has been polymerized with pNIPAM to 10× it's size, 300 kD. FIGS. 6 and 7 demonstrate that the native enzyme which is only 33 kD has been grown to 40 kD, 150 kD and 300 kD by adding a thermally responsive polymer (pNiPAAm) to it.

Figure 8:
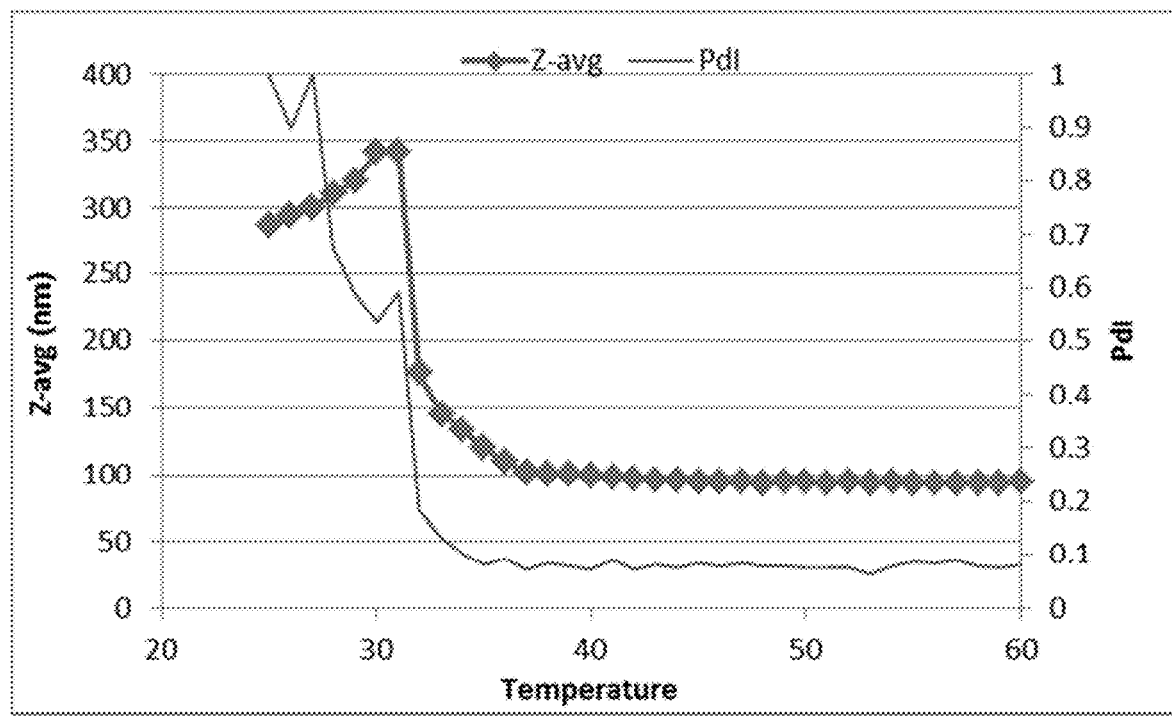
FIG. 8 is a plot of the DLS output of the Lipase-pNiPAAm nanoparticles (300 kD). It shows the DLS size readings (z-average) and the PDI (polydispersity index) that were taken at one degree increments between 25° C. and 60° C.

Dynamic light scattering (DLS) was used to determine the size response of NanoStable Lipase to increases in temperature. A Malvern Zetasizer Nano ZS was used to determine NanoStable Lipase size at various temperatures. NanoStable Lipase was diluted in filtered deionized water to 0.01 mg/mL before size measurements were taken. FIG. 8 shows the DLS size readings that were taken at one degree increments between 25° C. and 60° C. for the 300 kD MW nanoparticles. The Z-average of the NanoStable Lipases shrunk by approximately 67% when the temperature increased above pNiPAAm's LCST from approximately 300 nanometers (nm) at ambient temperatures to approximately 100 nm at elevated temperatures. This phenomenon can also be seen by viewing the solution. The refractive index of pNIPAM changes when it is stored above its LCST; a physical response is seen as the solution turns from clear to opaque as the temperature rises above pNIPAM's LCST.

Figure 9:
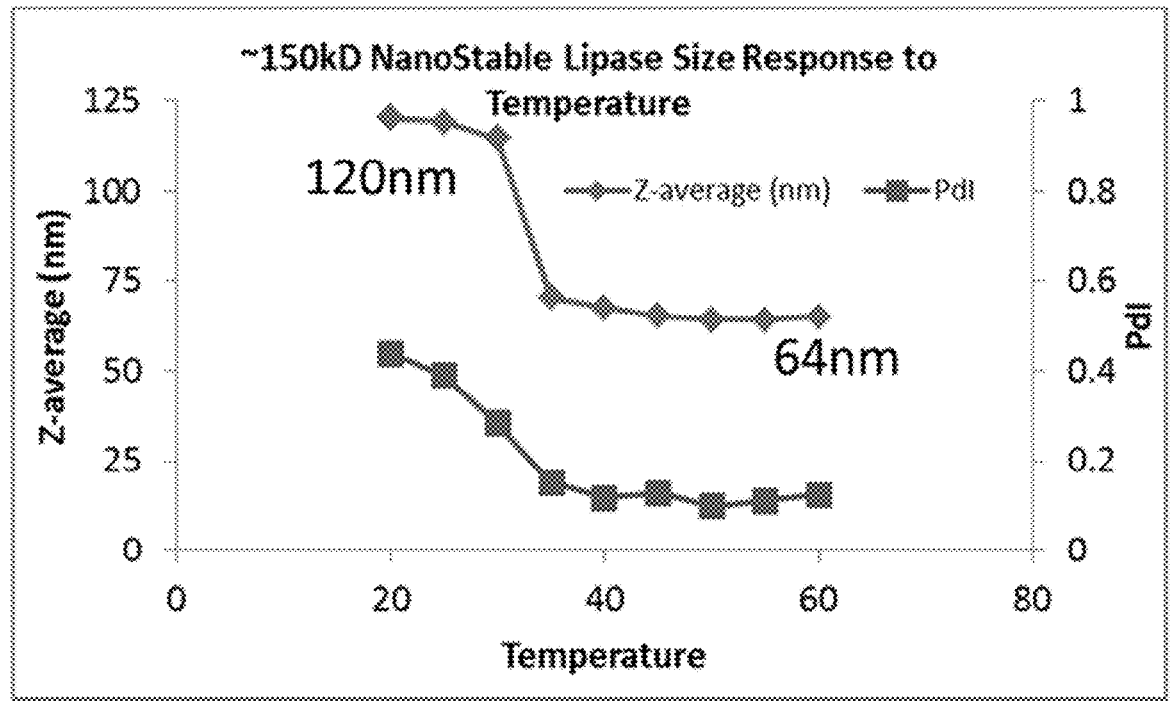
FIG. 9 is a plot of the DLS output of the Lipase-pNiPAAm nanoparticles (150 kD). It shows the DLS size readings (z-average) and the PDI (polydispersity index) that were taken at five degree increments between 20° C. and 60° C.
Figure 10:
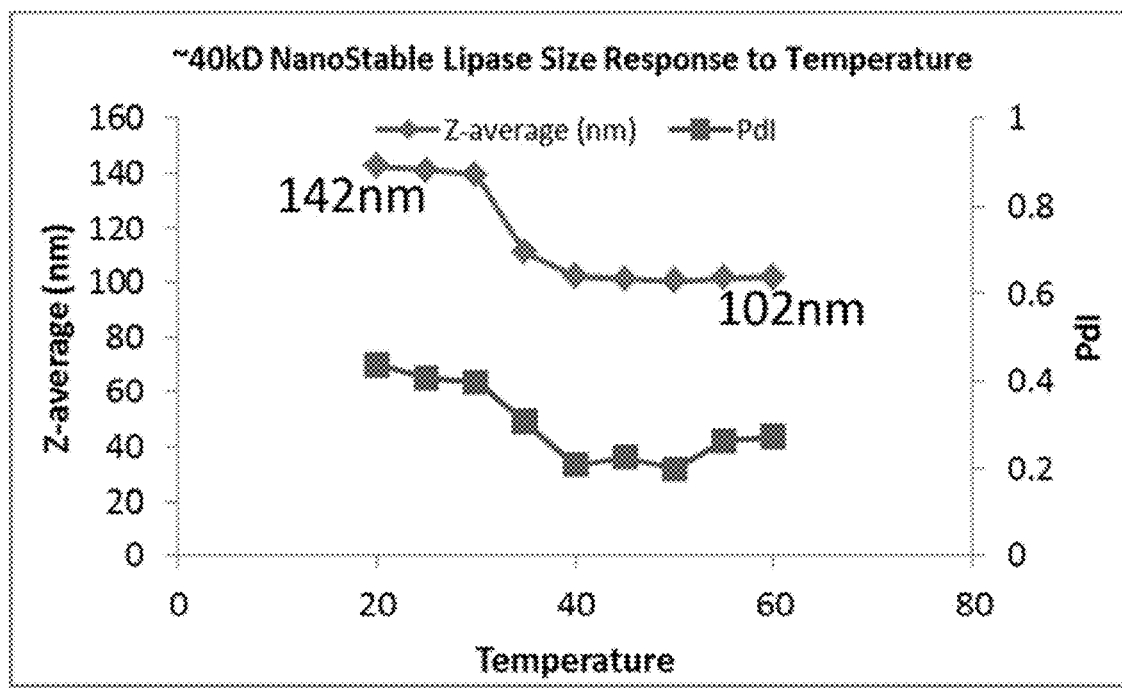
FIG. 10 is a plot of the DLS output of the Lipase-pNiPAAm nanoparticles (40 kD). It shows the DLS size readings (z-average) and the PDI (polydispersity index) that were taken at five degree increments between 20° C. and 60° C.

FIG. 9 shows the DLS size readings that were taken at five degree increments between 20° C. and 60° C. for the 150 kD NanoStable Lipase. The Z-average diameter of the 150 kD NanoStable Lipase decreases by approximately 47% when the temperature increased above pNiPAAm's LCST from approximately 120 nm at ambient temperatures to approximately 64 nm at elevated temperatures. This phenomenon can also be seen by viewing the solution. The refractive index of the particles change when they shrink above the LCST for pNiPAAm. The physical response to temperature is seen as the solutions goes from clear to opaque at elevated temperatures. FIG. 10 shows the DLS size readings that were taken at five degree increments between 20° C. and 60° C. for the 40 kD NanoStable Lipase. The size of the 40 kD NanoStable Lipase decreases by approximately 39% when the temperature increased above pNiPAAm's LCST from approximately 142 nm at ambient temperatures to approximately 102 nm at elevated temperatures. This phenomenon can also be seen by viewing the solution. The refractive index of pNIPAM changes when it is above its LCST and the solution becomes opaque.

Figure 11:
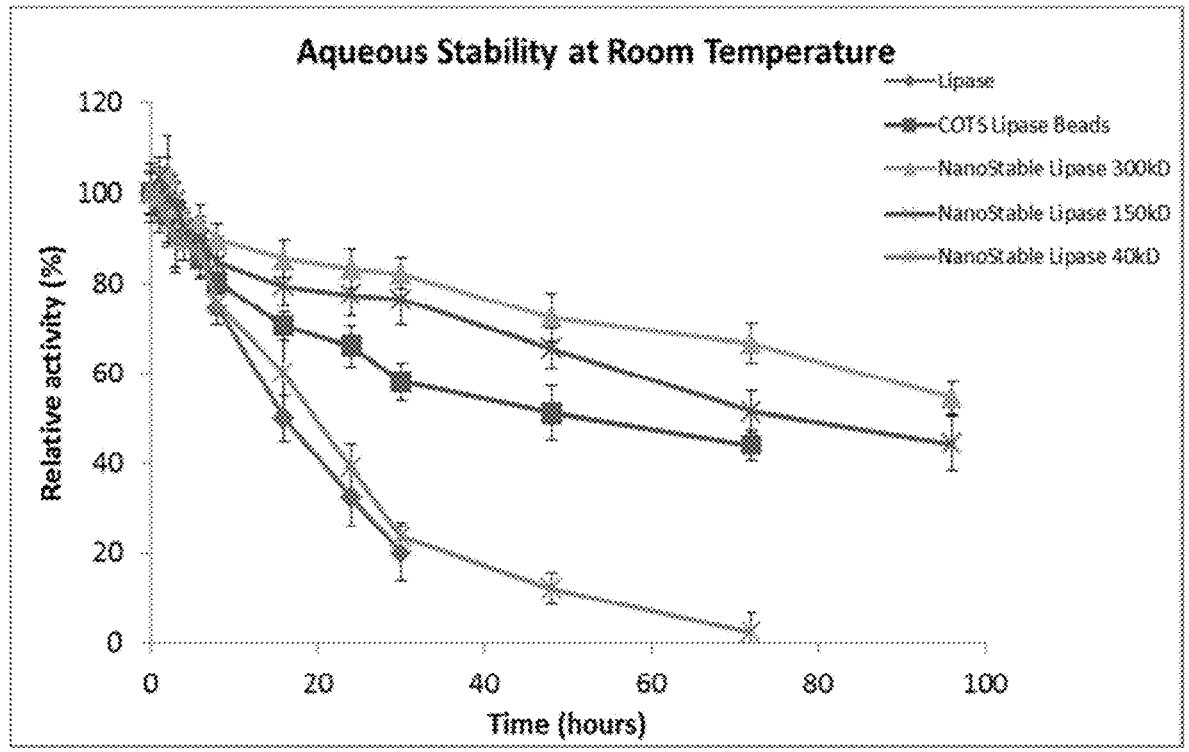
FIG. 11 is a plot of the relative catalytic activity retained for different Lipase samples over time at room temperature. The samples include: native Lipase, Commercial Off the Shelf Stabilized Lipase Beads (ChiralVision), and NanoStable Lipase with a MW of 300 kD, 150 kD and 40 kD.
Figure 12:
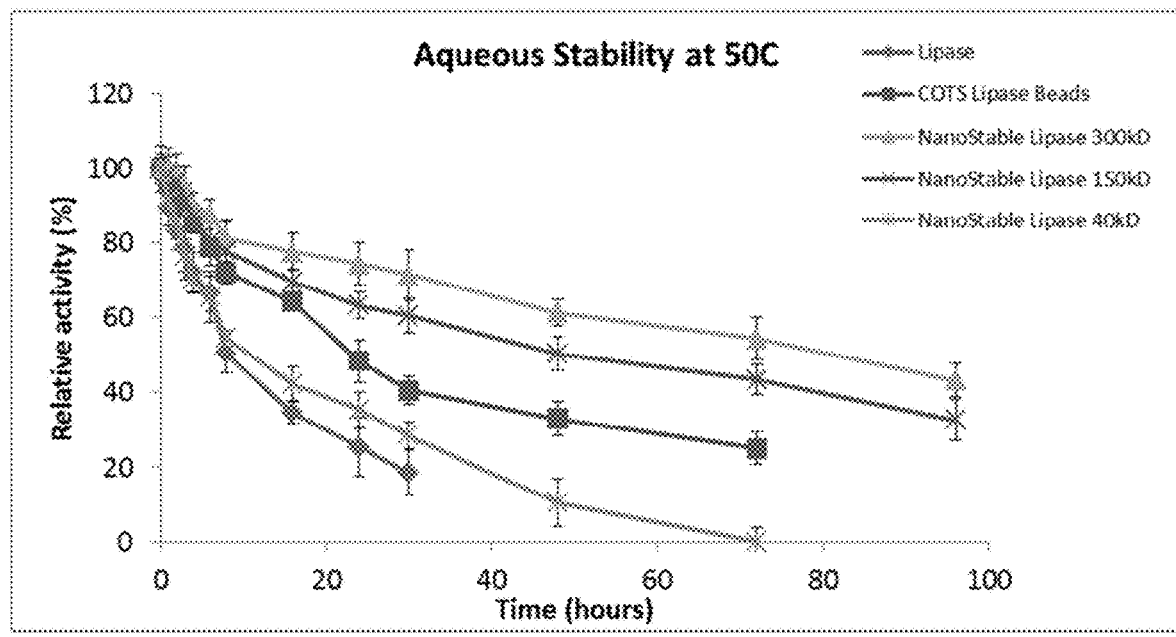
FIG. 12 is a plot of the relative activity retained of different Lipase samples over time at 50° C. The samples include, Native Lipase, Commercially Off the Shelf Stabilized Lipase Beads (ChiralVision), and NanoStable Lipase with a MW of 300 kD, 150 kD and 40 kD.
Figure 13:
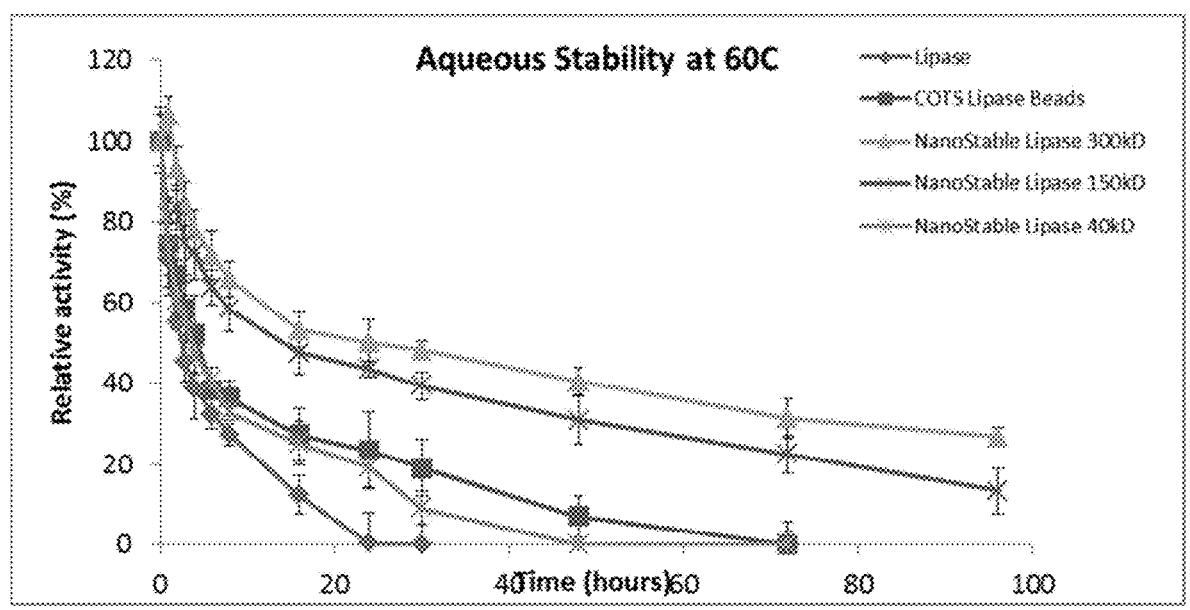
FIG. 13 is a plot of the relative activity retained of different Lipase samples over time at 60° C. The samples include, Native Lipase, Commercially Off the Shelf Stabilized Lipase Beads (ChiralVision), and NanoStable Lipase with a MW of 300 kD, 150 kD and 40 kD.
Figures 14, 15:
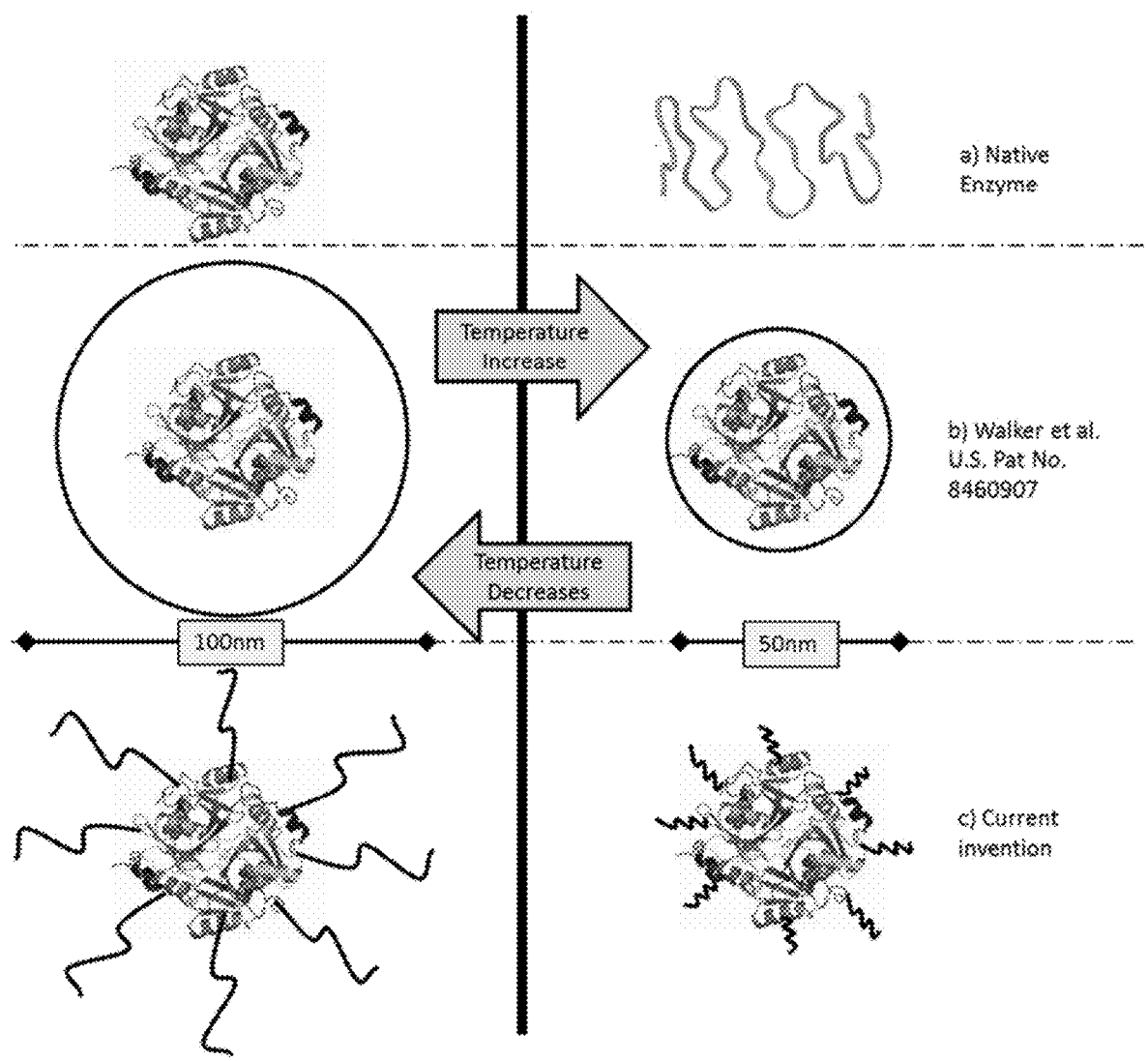
FIG. 14 is a table of the half-life of thermal inactivation of NanoStable Lipase, Native lipase and commercially of the shelf Lipase beads. Thermal inactivation half-life is defined as when the samples lose 50% of their original catalytic activity.
FIG. 15 shows a conceptual representation of the effect temperature has on free enzymes, encapsulated enzyme within thermal-responsive nanoparticles as used in Walker et al. (U.S. Pat. No. 8,460,907) and enzymes bound to individual polymer chains attached to the enzymes or grown from them via controlled radical polymerization. Free enzymes ordinarily denature when exposed to increases in temperature, while encapsulated or bound enzyme's tertiary structure is protected by the collapsing responsive polymer. Further, the shell of the encapsulated enzyme inhibits the rate at which the enzyme can turn over larger substrate. By binding the polymers directly to the enzyme to make a transient nanoparticle which becomes dense only at elevated temperatures, the substrate can more easily migrate to the active site of the enzyme unimpeded by a polymer shell.

Catalytic activity of Lipase was determine via a colorimetric assay. NanoStable Lipase (40, 150 and 300 kD), native Lipase and a commercial off the shelf stabilized Lipase were stored at ambient and elevated temperatures and monitored to determine their half-life of thermal inactivation. Prior to incubation at elevated temperatures the catalytic activity of the Lipase samples was assessed; the thermal half-life of inactivation is established when the samples lose 50% of its original activity. FIGS. 11, 12 and 13 show the relative activity of the Lipase Samples at ambient, 50° C. and 60° C., respectively. The thermal half-life of inactivation in hours for all samples are shown in FIG. 14. Through attachment of a thermally-responsive polymer of the present invention, Lipase samples increase their half-life from 16 hours (native) to 96+ hours (300 kD nanoparticles, a 6 fold increase) at room temperature; from 8 hours (native) to 84 hours (300 kD nanoparticles, a 10.5 fold increase) at 50° C.; and from 2.5 hours (native) to 30 hours (300 kD nanoparticles, a 12 fold increase) at 60° C. An increase in half-life versus commercially available stabilized Lipase is also seen (2-fold at 23° C., 4-fold at 50° C. and 8-fold at 60° C.). NanoStable Lipase of the present invention retains a significantly higher degree of catalytic activity at elevated temperatures and have drastically longer half-lives. The thermal responsiveness of pNIPAM polymer chains at elevated temperatures increases thermal pot life (aqueous) stability of the lipase enzyme.

EXAMPLE 4

BSA Modification with pNiPAAM

Succinimidyl-TEG-Br (NHS-TEG-Br) ATRP initiator (ATRP Solutions, Pittsburgh, Pa.) was used to modify Bovine Serum Albumen (BSA). Twenty-Two milligrams of NHS-TEG-Br was added for every 200 mg of BSA in an aqueous buffered system (50 mM Borate pH 8.0, 16% v/v DMSO). The reaction was stirred for 1 hour at +4° C. Excess NHS-TEG-Br was removed by ultrafiltraion in a 50 mL Millipore stirred cell with a 10,000 molecular weight cut off (MWCO) filter installed. The outflow of the filtered cell was monitored by UV 260 for complete removal of excess initiator. Concurrently, the buffer was exchanged to 15 mM Tris HCl, pH 7.6, and the protein was concentrated to greater than 2.5 mg/mL.

The BSA-TEG-Br (BSA-Br) conjugate was then modified with N-Isopropylacrylamide (NIPAAm) via ATRP. 10 mg of BSA-Br was combined with 83 mg of NIPAAm in a 10 mL Schlenk flask and deoxygenated. A solution containing 0.03 mg CuCl, 0.0014% ME6TREN, and 0.01 mg CuCl2 was then made under deoxygenated conditions. This solution was then charged into the deoxygenated Schlenk flask and the reaction was allowed to progress for 1 hour at +4° C.

The full reaction was transferred to a millipore stirred cell with a 30,000 MWCO filter installed. The outflow of the filtered cell was monitored by UV 260 for complete removal of the reaction components. The BSA-NIPAAm conjugate was then modified with Poly(ethylene glycol) methyl ether methacrylate (average molecular weight 475) (PEGMA475) via ATRP. 10 mg of BSA-NIPAAm was combined with a final concentration of 16.6% v/v PEGMA475 in a 10 mL Schlenk flask and deoxygenated. A solution containing 33.34 mg CuCl, 44.6 mg 2,2'-Bipyridyl, and 10.26 mg CuCl2 was then made under deoxygenated conditions. This solution was then charged into the deoxygenated Schlenk flask and the reaction was allowed to progress for 1 hour at +4° C.

The BSA conjugates were compared to native BSA by Sodium Dodecyl Sulfate Polyacrylamide Gel Electrophoresis (SDS-PAGE) after each modification step to determine the extent of modification (FIGS. 18 and 19). The larger the amount of PEGMA475 that was added the further the modification of the BSA (longer polymer chain growth). This is shown by the stains resistance to move through the gel. The protein band remains at the higher molecular weight end of the gel. Further in FIG. 19 the Barium Iodine stain shows that it is indeed PEGMA475 that is bound to the OPH-pNiPAAm conjugate. As the OPH-pNiPAAm conjugate by itself does not stain red.

Whereas particular embodiments of this invention have been described above for purpose of illustration, it will be evident to those persons skilled in the art that numerous variations of the details of the present invention may be made without departing from the scope and spirit of this invention as defined in the figures and the appended claims.

EXAMPLE 5

Glucose Oxidase (GOX), (E.C. 1.1.3.4) from *Aspergillus niger* Type VII, was obtained from Sigma Aldrich, St. Louis, Mo. GOX is a dimeric protein consisting of two 80 kD subunits. Each subunit contains 15 lysine residues. To assay the activity of the GOX, the reaction as show in FIG. 20 was performed. GOX was added to a well in a microplate. Then a solution containing buffer pH 7.0, glucose, 4-aminoantipyrine, 3-(N-Ethyl-3-methylanilino)2-hydroxypropanesulfonic, peroxidase and water was added to the same well. The reaction was observed at 555 nm using a micro plate reader to monitor the formation of the quinoneimine dye. One unit causes the formation of one micromole of hydrogen peroxide (half a micromole of quinoneimine dye) per minute

EXAMPLE 6

GOX was then modified with an initiator. First, GOX was modified with succinimidyl tetraethylene glycol bromine (NHS-TEG-Br) at a 10:1 initiator to lysine ratio. This ratio was chosen as optimal for retaining activity as well as modifying GOX to the extent that polymers can later be attached. The reaction was allowed to proceed for 2 hours at room temperature in the presence of DMSO and a basic buffer (50 mM Borate, pH 9.) The NHS-TEG-Br will bind to a lysine amine on the GOX, forming an amide bond.

Figures 21, 22:
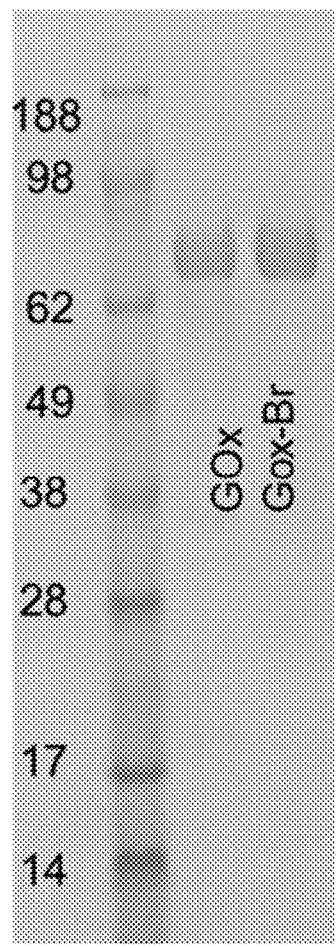
FIG. 21 is a picture of the gel that was made by performing sodium dodecyl sulfate polyacrylamide gel electrophoresis (SDS-PAGE) on initiator-modified GOX (GOX-Br) and native GOX.
FIG. 22 is a table showing the results of a fluoraldehyde assay of initiator modified GOX (GOX-Br) and native GOX.

After the modification reaction was complete, GOX-Br was analyzed for molecular weight (MW) estimation via sodium dodecyl sulfate polyacrylamide gel electrophoresis (SDS-PAGE) (FIG. 21). From the SDS-PAGE gel it was determined that the modification was a success as there is an observed slight increase in MW for GOX that was modified with NHS-TEG-Br.

Fluoraldehyde OPA Reagent is a primary amine-reactive fluorescent detection reagent and can be used to determine the reduction in the number of free amines from the native enzyme. GOX-Br was also analyzed for percent modification via the fluoraldehyde assay (FIG. 22). The Fluoraldehyde results show a decrease in fluorescence of 40% corresponding to 40% less free amines available for the fluoraldehyde OPA Reagent to react with 6 of GOX's 15 lysine residues were modified with the NHS-TEG-Br initiator.

Figure 23:
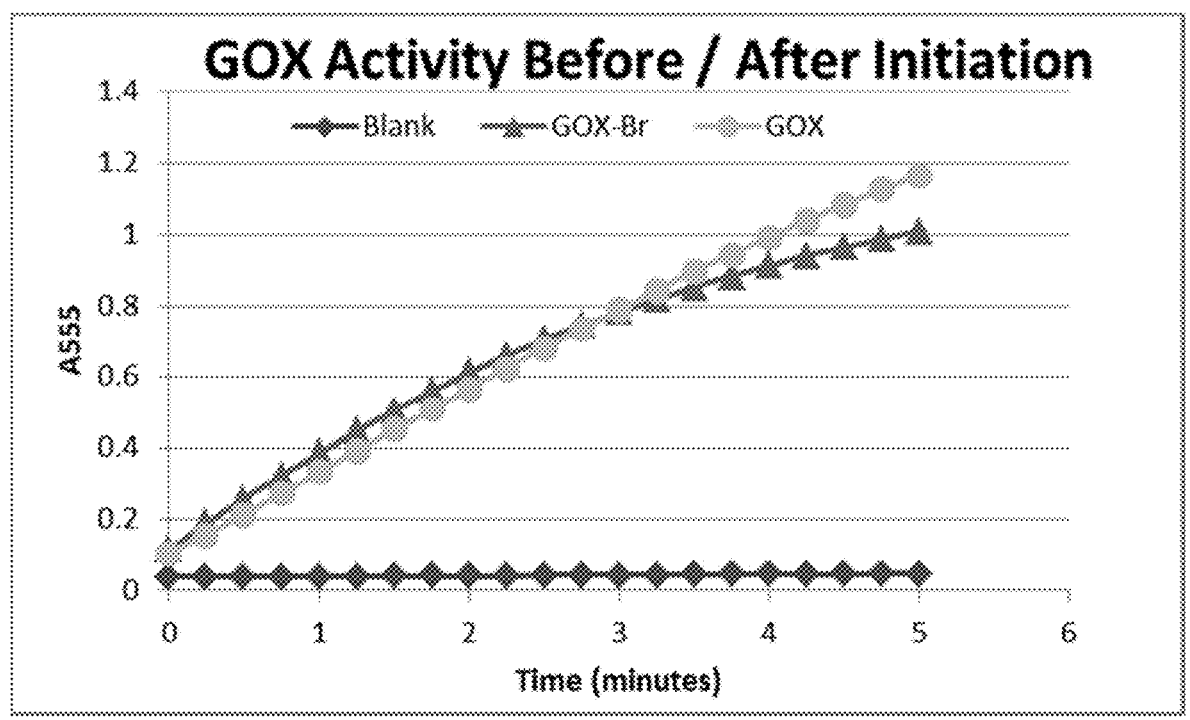
FIG. 23 shows the catalytic activity of initiator modified GOX (GOX-Br) and native GOX.

The catalytic activity of GOX-Br was analyzed to determine the retention of catalytic activity after modification (FIG. 23). GOX-Br was assayed using the standard assay conditions as shown in Example 5. Compared to the GOX starting material (native GOX), GOX-Br retains 98% of its original activity.

EXAMPLE 7

Figure 24:
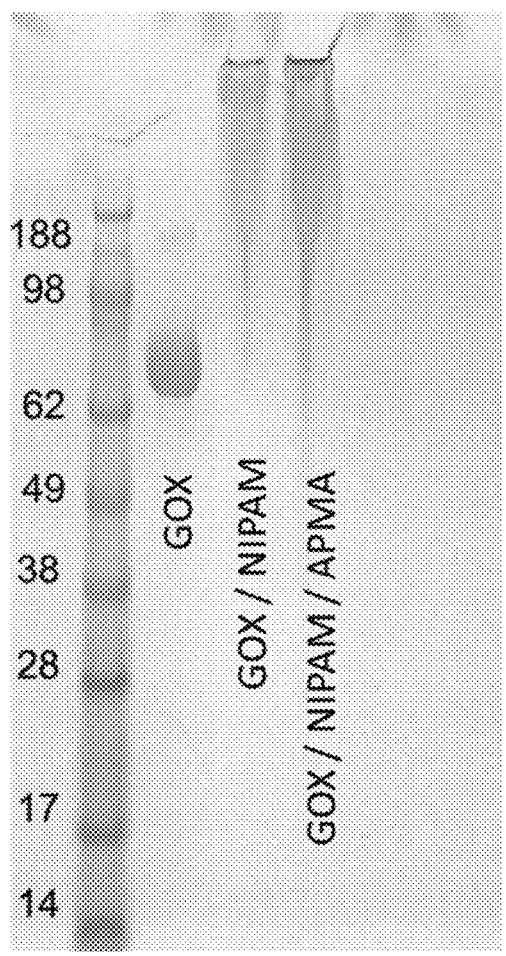
FIG. 24 is a gel that was made by performing sodium dodecyl sulfate polyacrylamide gel electrophoresis (SDS-PAGE) on initiator modified GOX, NanoStable GOX/pNIPAM, Nanostable GOX/pNIPAM/APMA.
Figure 25:
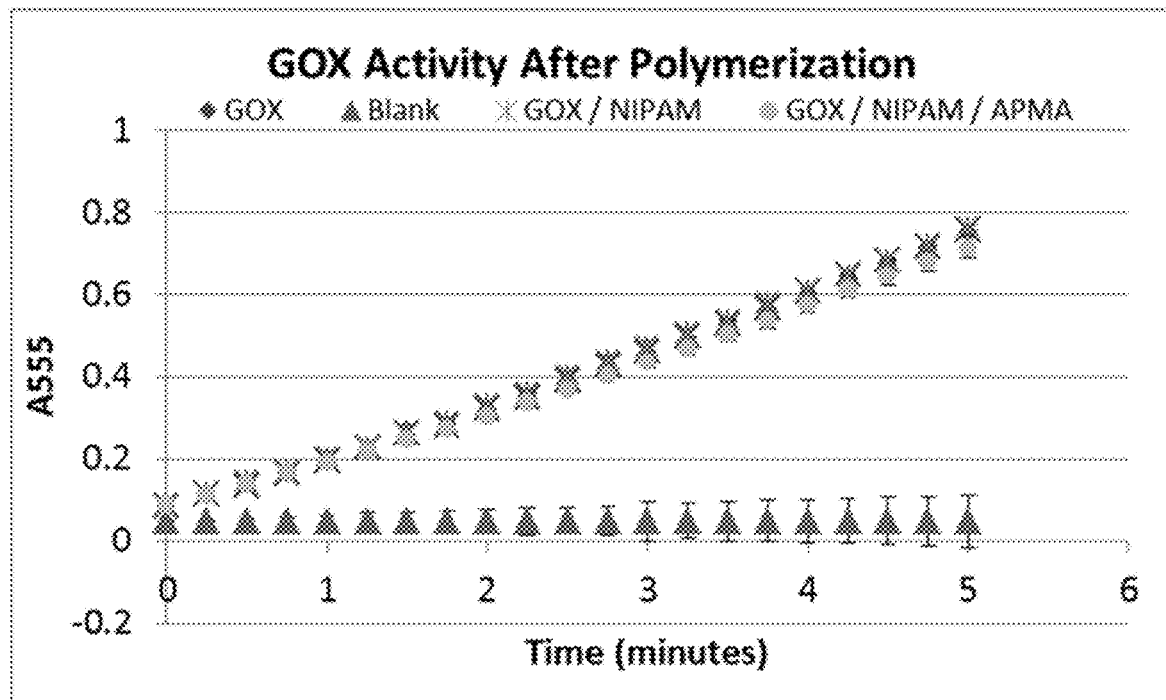
FIG. 25 is a graph depicting the catalytic activity of native GOX, NanoStable GOX/pNIPAM and NanoStable GOX/pNIPAM/APMA.

A thermally responsive polymer, poly(N-isopropylacrylamide), (pNIPAM), was grown via ATRP from the initiated GOX-Br's surface resulting in NanoStable GOX/pNIPAM, which imparts enhanced thermal stability to the enzyme. The polymeric nanoplatform thermally stabilizes an enzyme by forming a support scaffold to prevent denaturation at elevated temperatures. NanoStable GOX/pNIPAM was analyzed via SDS-PAGE to estimate the MW after polymerization (FIG. 24). The NanoStable GOX/pNIPAM increased in MW to approximately 300 kD which is an increase over the initiator modified GOX (GOX-Br) showing the polymer attachment was a success. The retention of catalytic activity was also determined using the standard assay protocol in Example 5 (FIG. 25). The activity retention of NanoStable GOX/pNIPAM when compared to native GOX starting material is greater than 94%.

EXAMPLE 8

Figure 26:
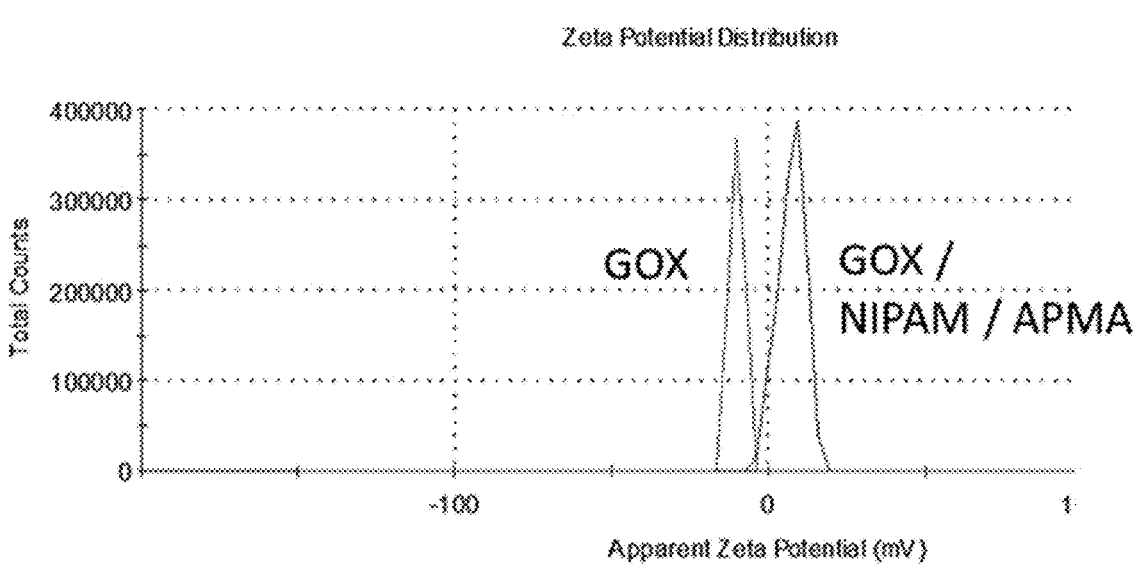
FIG. 26 shows the zeta potential of native GOX and NanoStable GOX/pNIPAM/APMA.

An additional function to GOX was beaded to the polymer chain via ATRP to impart additional amine functionality. It was added using the monomer N-(3-Aminopropyl) methacrylamide hydrochloride (APMA) resulting in NanoStable GOX/pNIPAM/APMA. The MW of NanoStable GOX/pNIPAM/APMA was analyzed via SDS-PAGE (FIG. 5). GOX is determined to be modified from the change in MW to approximately 300 kD. The activity retention was determined using the stand assay protocol in Example 1 (FIG. 6). The activity retention of NanoStable GOX/pNIPAM/APMA is greater than 90% when compared to the native GOX starting material. Minimal activity was lost during the modification. The addition of the APMA amine monomer was additionally analyzed by measuring the zeta potential of the sample (FIG. 26). The addition of amines (from the APMA monomer) to NanoStable GOX/pNIPAM should result in a more positive Zeta Potential when compared to the native GOX. Native GOX has a zeta potential of −10 mV while NanoStable GOX/pNIPAM/APMA has a zeta potential of +8.04 mV. The amine monomer provides a positive charge to the enzyme conjugate. The increase in zeta potential by 18.4 mV indicates the amine monomer has been conjugated to NanoStable GOX/pNIPAM and imparts amine functionality. The addition of APMA should result in a reduced amount of aggregation, as pNIPAM polymer chains are known in the literature to form polymeric aggregates.

EXAMPLE 9

To ensure the addition of the APMA monomer did not interfere with pNIPAM's physical properties, the size distribution of NanoStable GOX/pNIPAM/APMA from 25° C. to 60° C. was measure via DLS (FIG. 27). pNiPAM collapses at temperatures above its lower critical solution temperature (LCST), 32° C. NanoStable GOX has a particle-like response to temperature. The apparent size of NanoStable GOX/pNIPAM below pNIPAM's LCST (32° C.) is 140 nm, the size shrinks to 50 nm at temperatures above its LCST. pNIPAM has a characteristic aggregation that skews the true size of the conjugate. A 300 kD enzyme should have a size much less than 25 nm. In contrast, NanoStable GOX/pNIPAM/APMA undergoes a size transition from 51 nm at 25° C. to 22 nm at temperatures above 32° C. The charge from APMA reduces the amount of aggregation seen in the NanoStable GOX/pNIPAM/APMA conjugate. There is still some aggregation present from pNIPAM, but the APMA demonstrates that the aggregate formation is driven by the tendency of pNIPAM to self-aggregate.

EXAMPLE 10

To ensure that the addition of the APMA monomer does not interfere with the enhanced thermal stability provided by pNIPAM temperature stability studies were performed. Operational stability studies were conducted at ambient conditions, 37° C., 50° C. and 60° C. for native GOX, NanoStable GOX/pNIPAM and NanoStable GOX/pNIPAM/APMA. The aqueous stability of native GOX, NanoStable GOX/pNIPAM and NanoStable GOX/pNIPAM/APMA was monitored in PBS buffer pH 7.4. Each sample had equivalent initial catalytic activity and protein concentration. Samples were stored in triplicate at each temperature.

Aliquots from each sample were removed and assayed according to the procedure in Example 5 for retention of catalytic activity over 1 week (FIGS. 28-31). After one week of storage at room temperature native GOX retained 50.8% of its original activity, NanoStable GOX/pNIPAM retained 85.4% and NanoStable GOX/pNIPAM/APMA retained 80.6%. After one week of storage at 37° C. native GOX retained 35.4% of its original activity, NanoStable GOX/pNIPAM retained 55.4% and NanoStable GOX/pNIPAM/APMA retained 44.7%. After one week of storage at 50° C. native GOX retained 20% of its original activity, NanoStable GOX/pNIPAM retained 53.4% and GOX/pNIPAM/APMA retained 46.4%. After one week of storage at 60° C. native GOX retained 2.9% of its original activity, NanoStable GOX/pNIPAM retained 38.5% and NanoStable GOX/pNIPAM/APMA retained 30.7%. There is a modest decrease in operational stability for NanoStable GOX/pNIPAM/APMA samples compared to NanoStable GOX/pNIPAM. The addition of the APMA monomer to NanoStable GOX/pNIPAM produces a thermally stable conjugate with the additional function of amine reactivity, likely the additional charge on the polymer causes the chains to be slightly more hydrophilic and thus keeps them somewhat more swollen above the LCST compared with GOX/pNIPAM conjugates.

EXAMPLE 11

A glucose sensing element with enhanced thermal stability was created from NanoStable GOX/pNIPAM/APMA. A GOX containing hydrogel can be utilized to monitor glucose levels for a variety of applications. NanoStable GOX/pNIPAM/APMA was modified with acrylic acid N-hydroxysuccinimide ester (aaNHS). The amines on the APMA are modified with aaNHS during the reaction, thereby functionalizing the conjugate with a polymerizable acrylate. aaNHS can then be cross linked during a UV free radical polymerization reaction within a polymer hydrogel, which ensures the enzyme is cross-linked or immobilized within the hydrogel. NanoStable GOX/pNIPAM/APMA hydrogels exhibit enhanced thermal stability and enhanced retention of activity after hydrogel curing than Native GOX containing Hydrogels.

NanoStable GOX/pNIPAM/APMA was modified with aaNHS via a modification reaction at a 1:1 modifier to lysine ratio. Native GOX was also modified with aaNHS via a modification reaction at a 1:1 modifier to lysine ratio for use as a control. The reaction was performed at ambient temperatures in the presence of 10% DMSO and 50 mM Borate pH 9.0. The reaction was allowed to proceed for 1 hour.

Figures 31, 32:
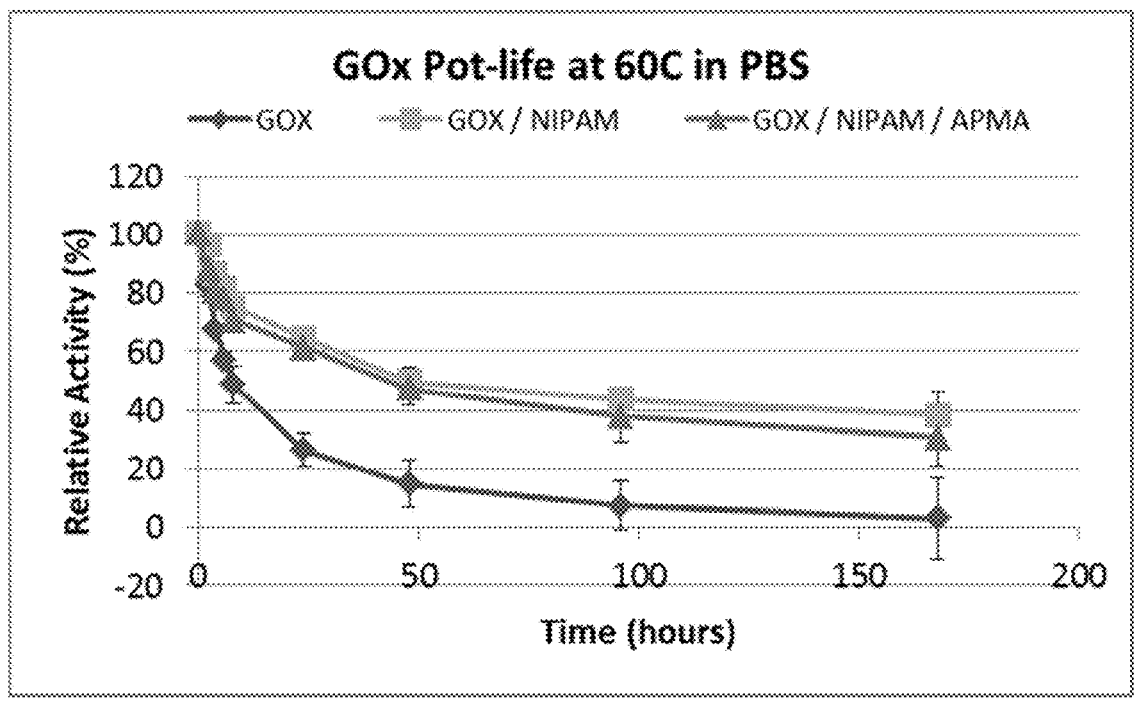
FIG. 31 is a graph depicting the catalytic activity of native GOX, NanoStable GOX/pNIPAM and NanoStable GOX/pNIPAM/APMA over time stored in PBS buffer at 60° C.
FIG. 32 is a table showing the results of a fluoraldehyde assay of NanoStable GOX/pNIPAM/APMA, NanoStable GOX/pNIPAM/APMA-aa, native GOX and GOX-aa. The table also depicts the catalytic activity of NanoStable GOX/NIPAM/APMA, NanoStable GOX/NIPAM/APMA-aa, native GOX and GOX-aa.

The number of aaNHS conjugates added to NanoStable GOX/pNIPAM/APMA was determine via a fluoraldehyde assay to monitor the decrease in free amines from NanoStable GOX/pNIPAM/APMA after aaNHS conjugation. There is a 30% reduction in fluorescence after the aaNHS conjugation, indicating 30% of the APMA amines were modified with aaNHS (FIG. 32). The catalytic activity of NanoStable GOX/pNIPAM/APMA was also monitored prior to and after modification using the standard assay protocol in Example 1 (FIG. 32). The activity retention from Native GOX to NanoStable GOX/pNIPAM/APMA-aa is greater than 87%. The NanoStable platform and subsequent modification steps are not detrimental to the catalytic activity of GOX. GOX that is modified with aaNHS is modified at approximately 30% and retains 95% activity when compared to native GOX (FIG. 32).

EXAMPLE 12

NanoStable GOX/pNIPAM/APMA-aa containing hydrogels exhibit exceptional activity retention after curing and enhanced thermal stability when compared to the state-of-the-art. NanoStable GOX/pNIPAM/APMA-aa hydrogels were comprised from Hydroxyethyl)methacrylate (HEMA) and Acrylamide. Native GOX, GOX-aa and NanoStable GOX/pNIPAM/APMA-aa were polymerized within polyacrylamide and polyHEMA hydrogels.

Figure 27:
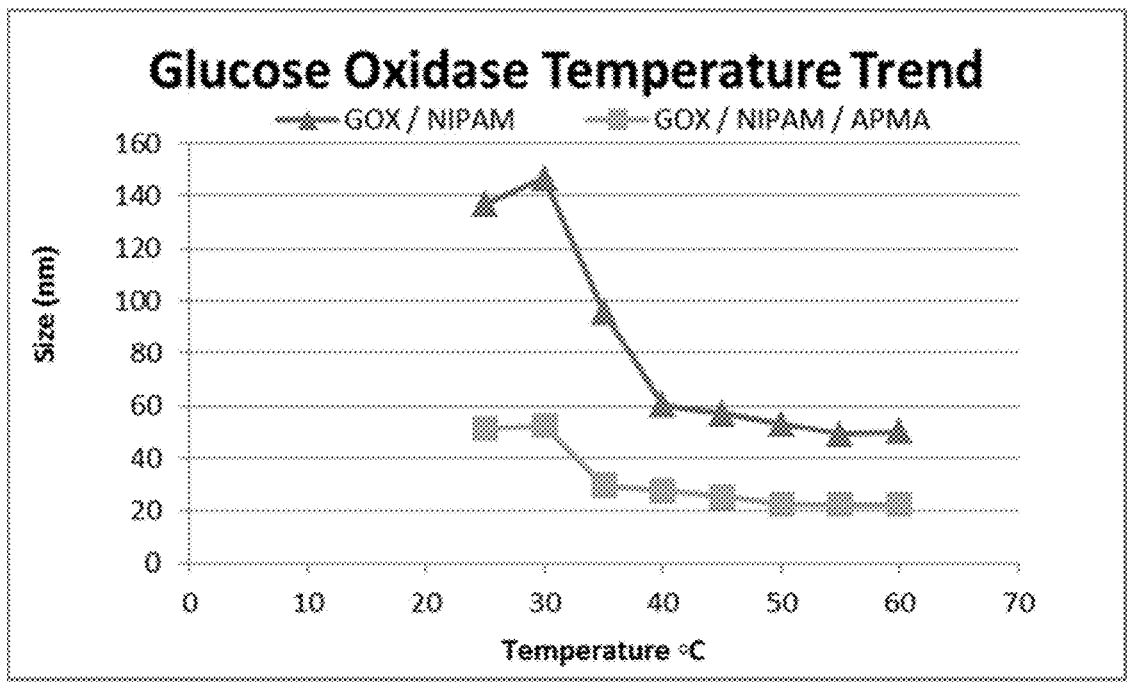
FIG. 27 shows size of the NanoStable GOX/pNIPAM and NanoStable GOX/pNIPAM/APMA nanoparticles as a function of temperature.
Figure 28:
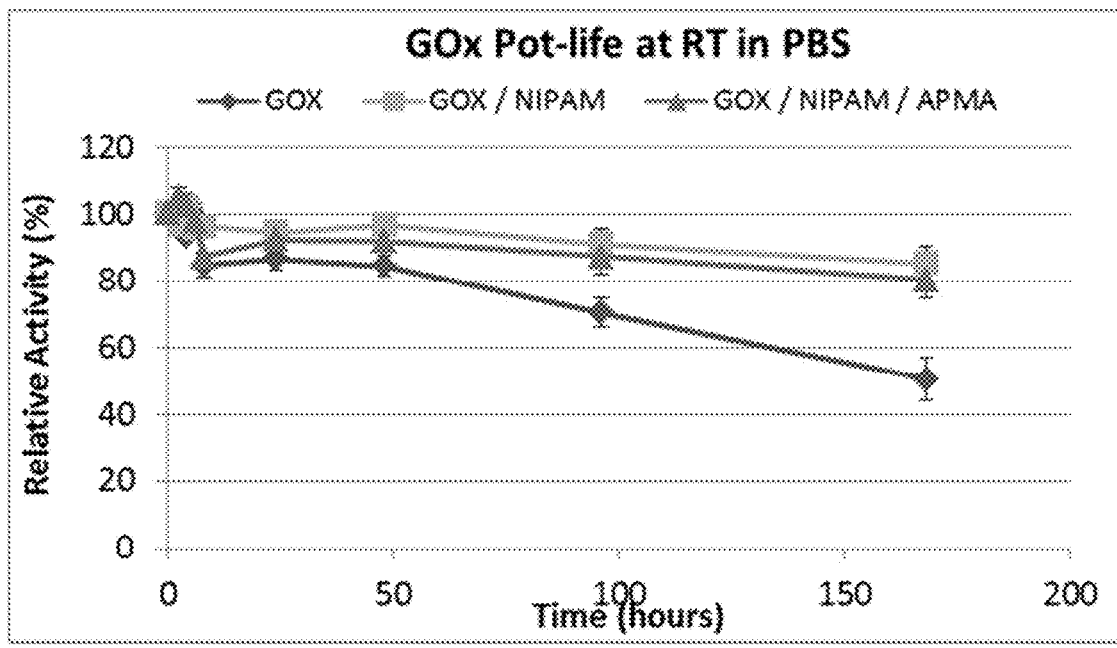
FIG. 28 is a graph depicting the catalytic activity of Native GOX, NanoStable GOX/pNIPAM and NanoStable GOX/pNIPAM/ APMA over time stored in PBS buffer at ambient temperature.
Figure 29:
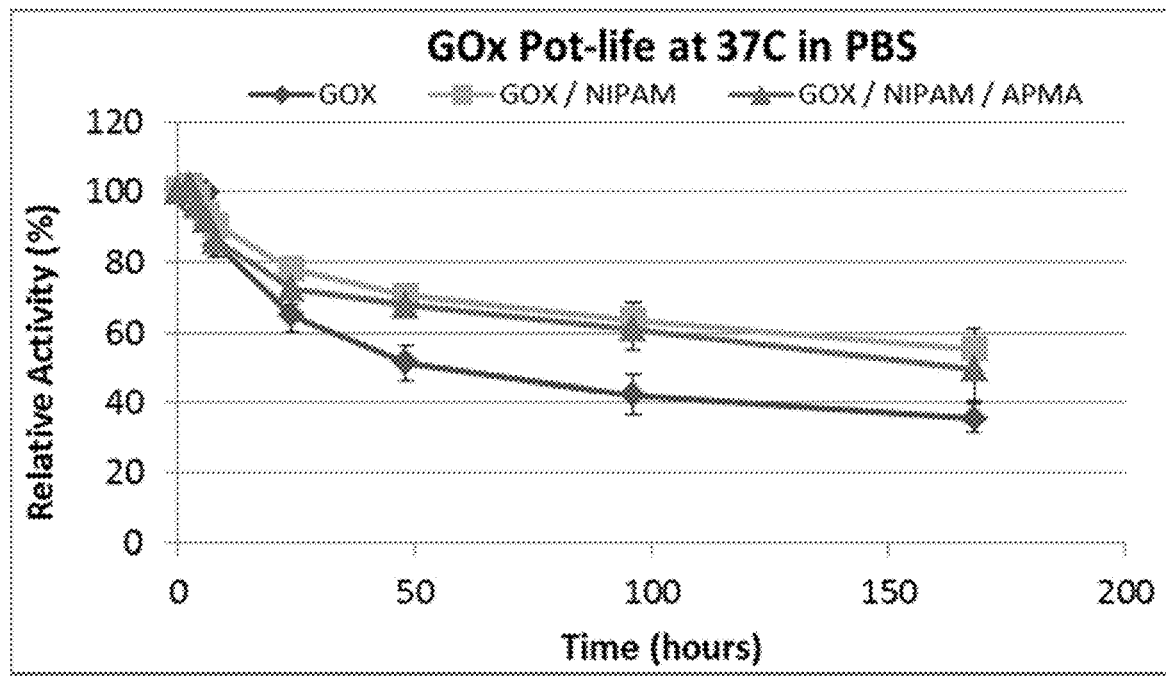
FIG. 29 is a graph depicting the catalytic activity of native GOX, NanoStable GOX/pNIPAM and NanoStable GOX/pNIPAM/APMA over time stored in PBS buffer at 37° C.
Figure 30:
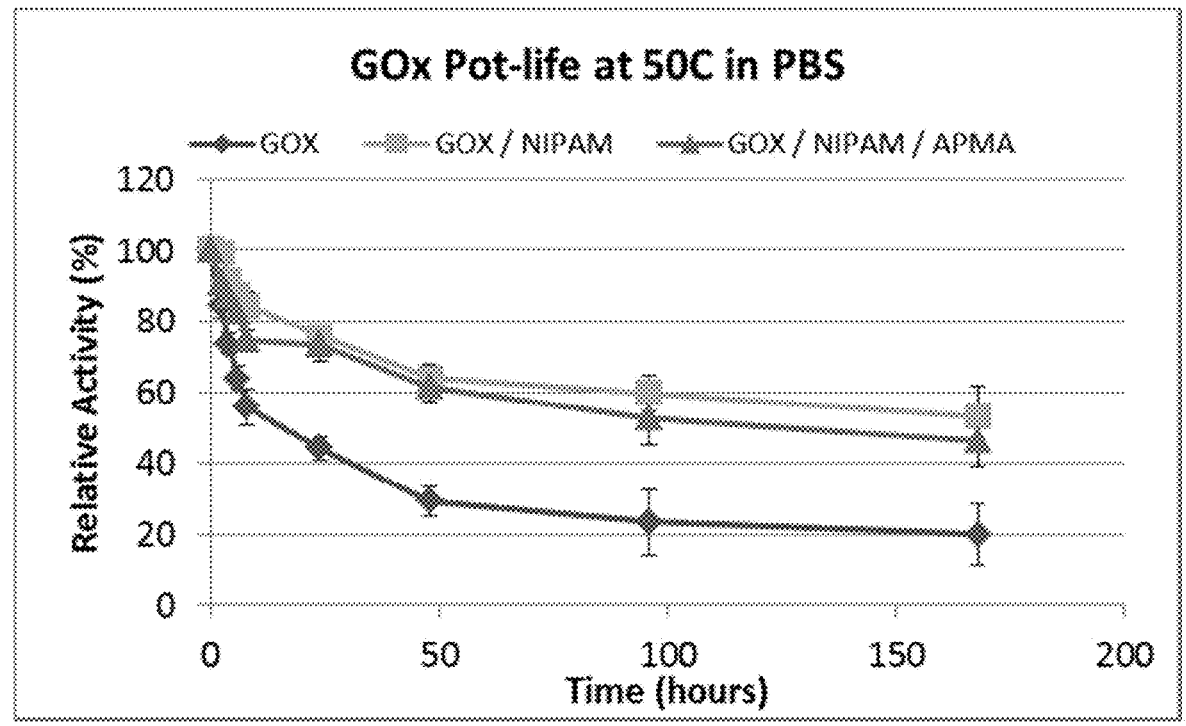
FIG. 30 is a graph depicting the catalytic activity of native GOX, NanoStable GOX/pNIPAM and NanoStable GOX/pNIPAM/APMA over time stored in PBS buffer at 50° C.

Polyacrylamide hydrogels were made using the following procedure. A mixture was made comprising the following 79% ($^v/_v$) Acrylamide Solution (40% ($^w/_v$) Acrylamide/8% ($^w/_v$) Bisacrylamide), 20% ($^v/_v$) GOX Solution, 1% ($^v/_v$) Initiator (2,2-dimethoxy-2-phenylacetophenone). The solution was then vortexed. A 10 μL aliquot was then put onto quick release paper and cured for 2 minutes by exposure to UV light at 365 nm. One solution was made with the GOX solution containing native GOX, another with GOX-aa and one with NanoStable GOX/pNIPAM/APMA-aa. Each GOX solution was made at three different concentrations. The three different stock concentrations for native GOX and GOX-aa were made at 12, 6 and 3 mg/mL. The final concentration in the hydrogel was 2.4, 1.2 and 0.6 mg/mL respectively. The three different Stock Concentrations for NanoStable GOX/pNIPAM/APMA-aa (NS GOX) were made at 10, 5, 2.5 mg/mL. The final concentration in the hydrogel was 2, 1, 0.5 mg/mL respectively. A table of the samples are shown in FIG. 27.

Poly(hydroxyethyl methacrylate) (polyHEMA) hydrogels were made using the following procedure. A mixture was made comprising 75% ($^v/_v$) Solution 1 (HEMA/di(ethylene glycol)dimethacrylate/2,2-dimethoxy-2-phenylacetophenone) and 25% ($^v/_v$) Solution 2 (Poly(ethylene glycol) methyl ether methacrylate/di(ethylene glycol)dimethacrylate/2,2-dimethoxy-2-phenylacetophenone). The solution was then vortexed. Then a GOX Solution was added at 20% ($^v/_v$) to the solution. The solution was vortexed again. A 10 μL aliquot was then put onto quick release paper and cured for 2 minutes by exposure to UV light at 365 nm. One was made with the GOX solution containing native GOX, another with GOX-aa and one with NanoStable GOX/pNIPAM/APMA-aa. Each GOX solution was made at three different concentrations. The three different stock concentrations for native GOX and GOX-aa were made at 12, 6 and 3 mg/mL. The final concentration in the hydrogel was 2.4, 1.2 and 0.6 mg/mL respectively. The three different Stock Concentrations for NanoStable GOX/pNIPAM/APMA-aa (NS GOX) were made at 10, 5, 2.5 mg/mL. The final concentration in the hydrogel was 2, 1, 0.5 mg/mL respectively. A table of the samples are shown in FIG. 33. The sample names in FIG. 33 are the same as in the following examples.

EXAMPLE 13

For the initial retention of catalytic activity, they were assayed immediately after UV curing to determine the retention of enzyme activity in the hydrogel samples. They were assayed according to the standard protocol in Example 5.

After 2 minute UV cure hydrogels were assayed in 96-well plates in triplicate. Specific catalytic activity was calculated from the linear portion of each activity curve. Specific activity was then compared to the activity of each starting material (SM) and reported as units per mg protein.

Figures 35, 36:
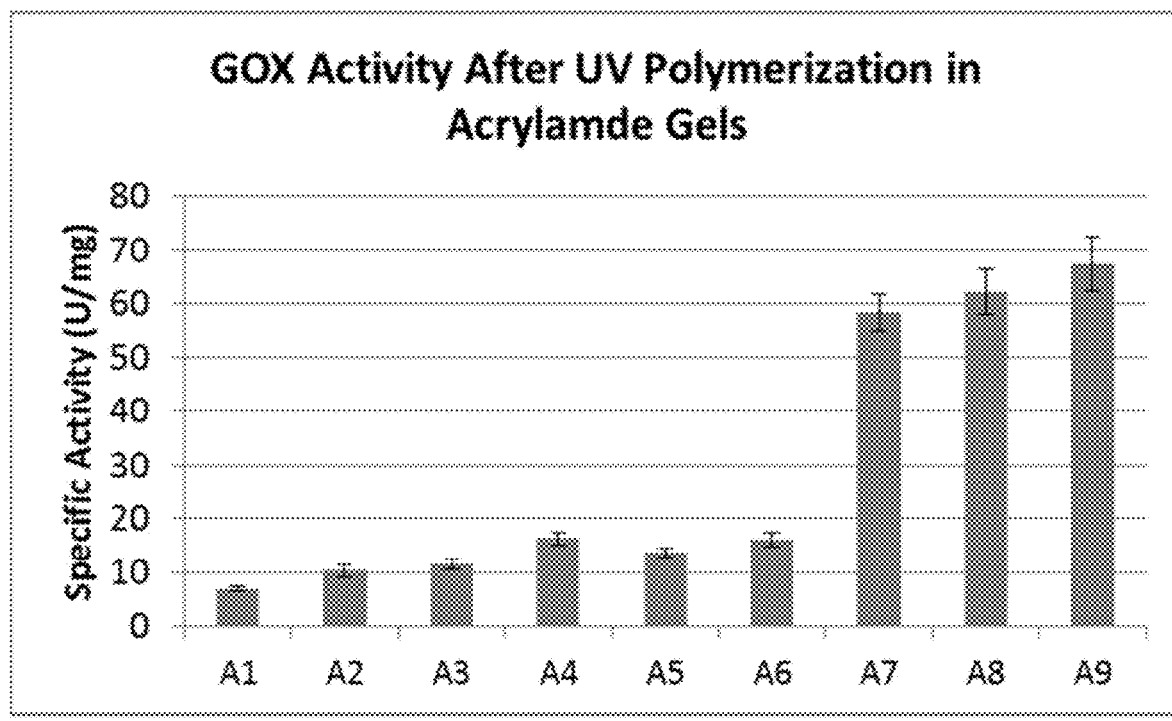
FIG. 35 is a graph containing the catalytic activity of GOX variants retained in the polyacrylamide hydrogel samples after the initial UV cure.
FIG. 36 is a table containing the catalytic activity of GOX variants retained in the HEMA hydrogel samples after the initial UV cure.

The retention of catalytic activity of GOX variants in polyacrylamide hydrogels is reported in FIGS. 34 and 35. Native GOX retains only 2 to 3% activity after UV curing in polyacrylamide Gels. When GOX is modified with aaNHS (GOX-aa) the activity retention is increase to 4 to 5%. When NanoStable GOX/pNIPAM/APMA is modified with aaNHS (NanoStable GOX/pNIPAM/APMA-aa) and UV cured the activity retention is 19 to 22%.

Figures 37, 38:
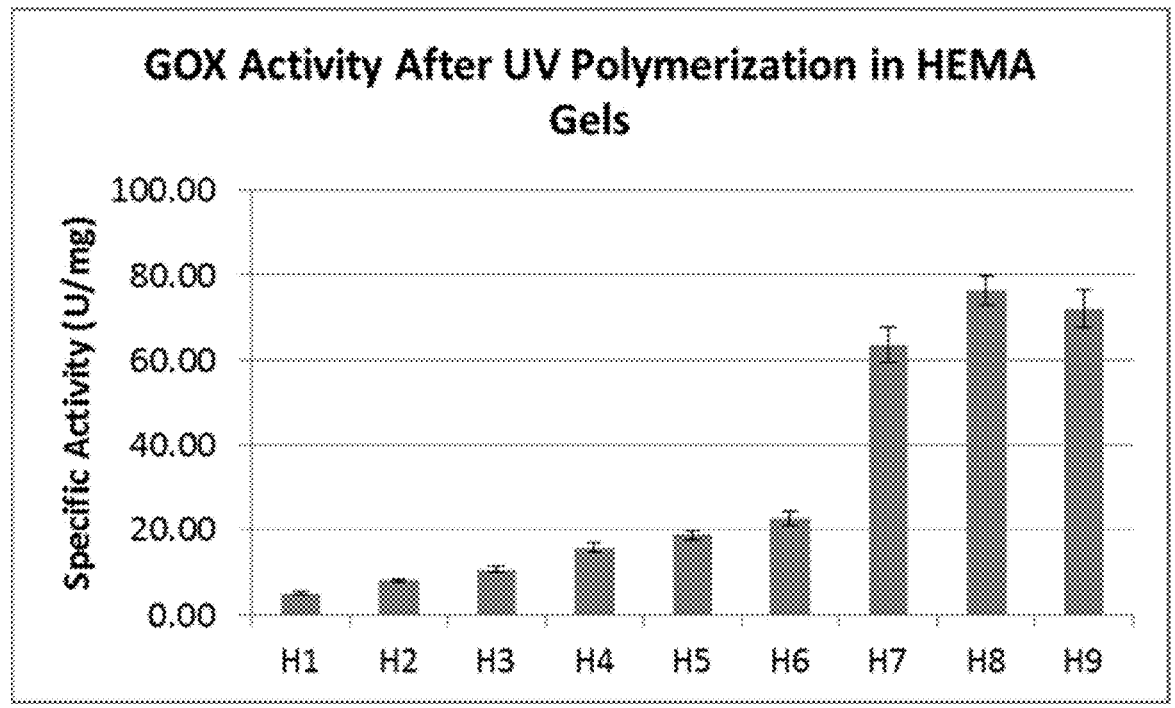
FIG. 37 is a graph containing the catalytic activity of GOX variants retained in the HEMA hydrogel samples after the initial UV cure.
FIG. 38 is a table containing the catalytic activity of GOX variants retained in the Acrylamide hydrogel samples after rinsing.

The retention of catalytic activity of GOX variants in polyHEMA hydrogels is reported in FIGS. 36 and 37. In the polyHEMA hydrogels, the results show a similar pattern to that of the polyacrylamide hydrogels. Native GOX retains less than 3% activity. GOX modified with aaNHS (GOX-aa) retains 4 to 7% activity. When NanoStable GOX/pNIPAM/

APMA is modified with aaNHS (NanoStable GOX/pNI-PAM/APMA-aa) and UV cured it retains 20 to 25% activity.

There is a significant increase in retention of activity when NS GOX-aa is cross-linked in polyacrylamide and polyHEMA hydrogels over native and aaNHS modified GOX. The additional amines from APMA that are modified help cross-link the enzyme into the hydrogel and retain more initial activity.

EXAMPLE 14

A rinsing study on the catalytic activity of the hydrogel samples was performed. They were assayed according to the standard protocol in Example 5. They were rinsed in PBS buffer to determine if enzyme will rinse out of the hydrogel or if the enzyme will be retained in the hydrogel (i.e. cross-linked into the hydrogel).

GOX containing hydrogels were incubated in PBS buffer and agitated for 5 minutes. The PBS buffer was then removed and assayed for GOX activity. The hydrogels were also assayed for retention of catalytic activity after rinsing. If all the enzyme is covalently cross-linked within the hydrogel none should be in the PBS buffer after rinsing. If the enzyme is cross-linked, the activity should remain within the hydrogel.

The retention of catalytic activity of GOX variants in polyacrylamide hydrogels is shown in FIGS. 19 and 20. Native GOX releases the most enzyme of all the samples and only retains 0.08% catalytic activity after rinsing. Attaching aaNHS to GOX (GOX-aa) retains more catalytic activity than native GOX. It retained 3.5% catalytic activity after rinsing. NanoStable GOX/pNIPAM/APMA-aa retains the most catalytic activity with more than 20% remaining.

Figures 39, 40:
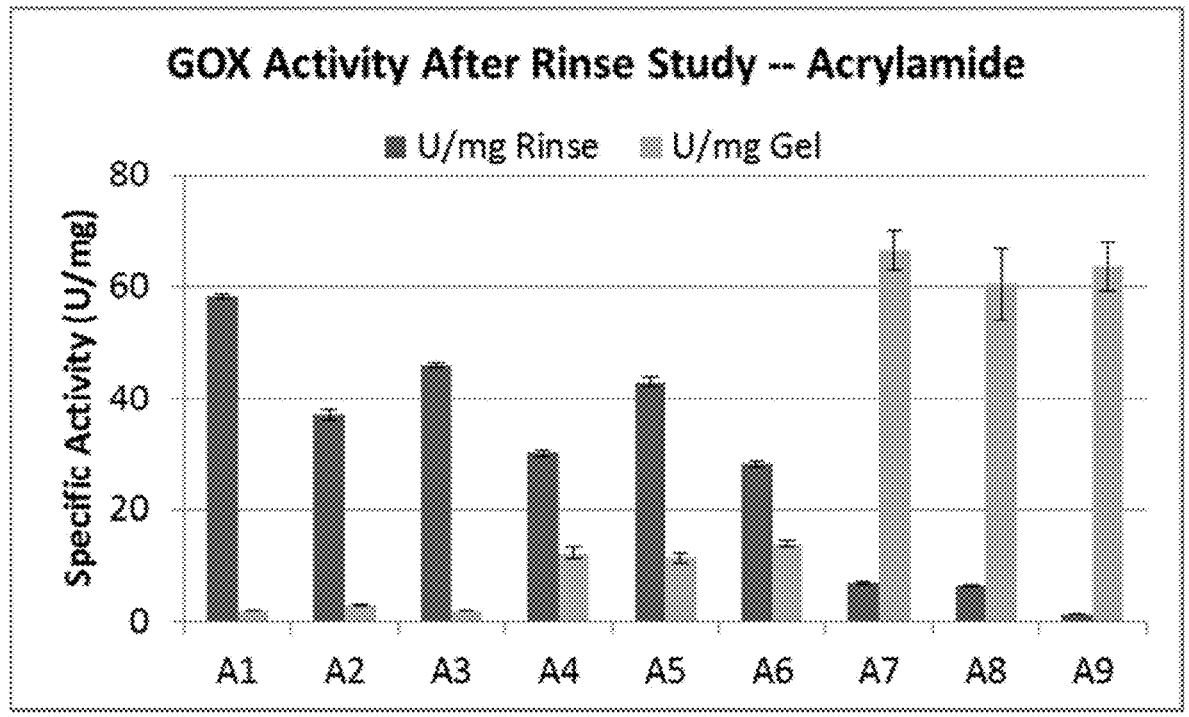
FIG. 39 is a graph containing the catalytic activity of GOX variants retained in the Acrylamide hydrogel samples after rinsing.
FIG. 40 is a table containing the catalytic activity of GOX variants retained in the HEMA hydrogel samples after rinsing.
Figure 41:
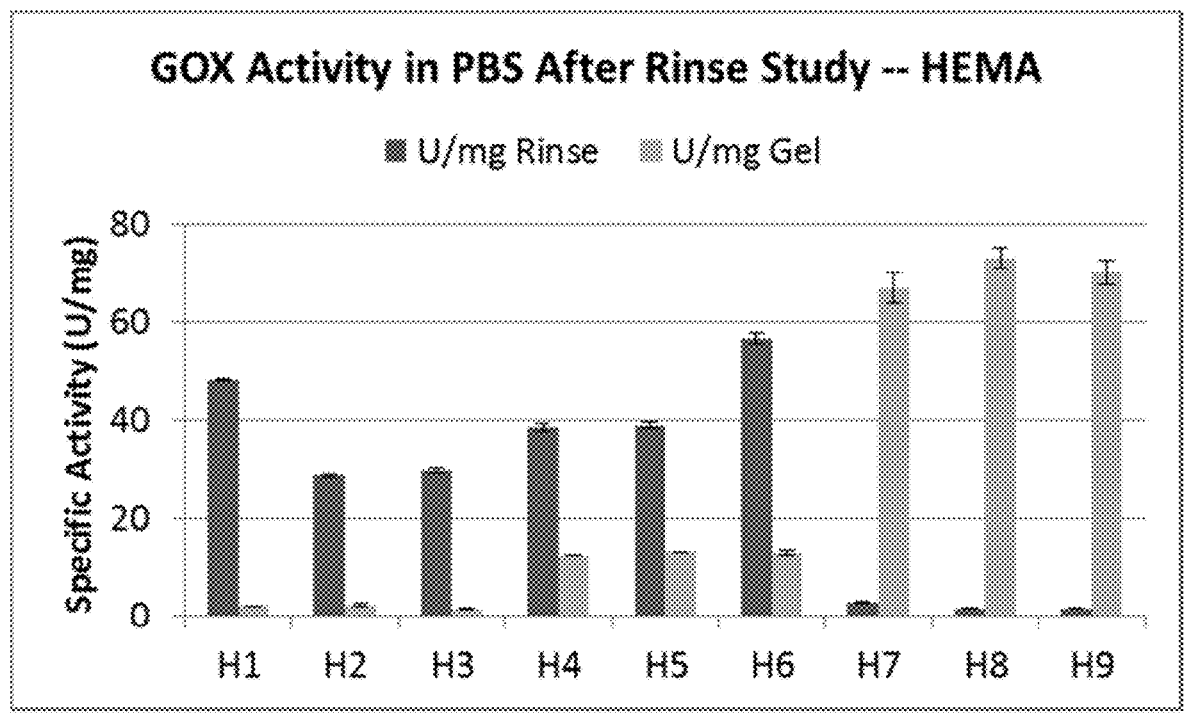
FIG. 41 is a graph containing the catalytic activity of GOX variants retained in the HEMA hydrogel samples after rinsing.

The retention of catalytic activity of GOX variants in HEMA Hydrogels is shown in FIGS. 40 and 41. A similar pattern was seen in HEMA hydrogels compared to the Acrylamide hydrogels. Native GOX retains 0.05% activity. GOX-aa retains 3.5% activity or 12.5 U/mg. NanoStable GOX/pNIPAM/APMA-aa retains 22.5% catalytic activity or 70 U/mg. Native GOX is not stable in hydrogels, the addition of aaNHS aids in a slight increase of catalytic activity primarily associated with improved immobilization. The most activity is retained when NanoStable GOX/pNI-PAM/APMA-aa is cross-linked into the hydrogels.

FIG. 42 provides a summary of catalytic activity retention from the GOX starting material used through modification, hydrogel polymerization and retention in the hydrogel after rinsing.

EXAMPLE 15

In the operational stability study at ambient temperatures and 37° C. GOX containing hydrogels were stored both dry and in PBS buffer at room temperature and at an elevated temperature (37° C.). They were assayed according to the standard protocol in Example 5. This will determine if the thermal enhancement seen when pNIPAM is polymerized from GOX to create NanoStable GOX/pNIPAM remains when NanoStable GOX/pNIPAM/APMA-aa (NS GOX-aa) is cross-linked into a hydrogel.

GOX containing hydrogels were incubated at room temperature and 37° C. They were also stored in their dry state and some were stored wet in PBS buffer. The catalytic activities of the hydrogels were monitored at time 0 and after 24, 48 and 120 hours.

Figure 43:
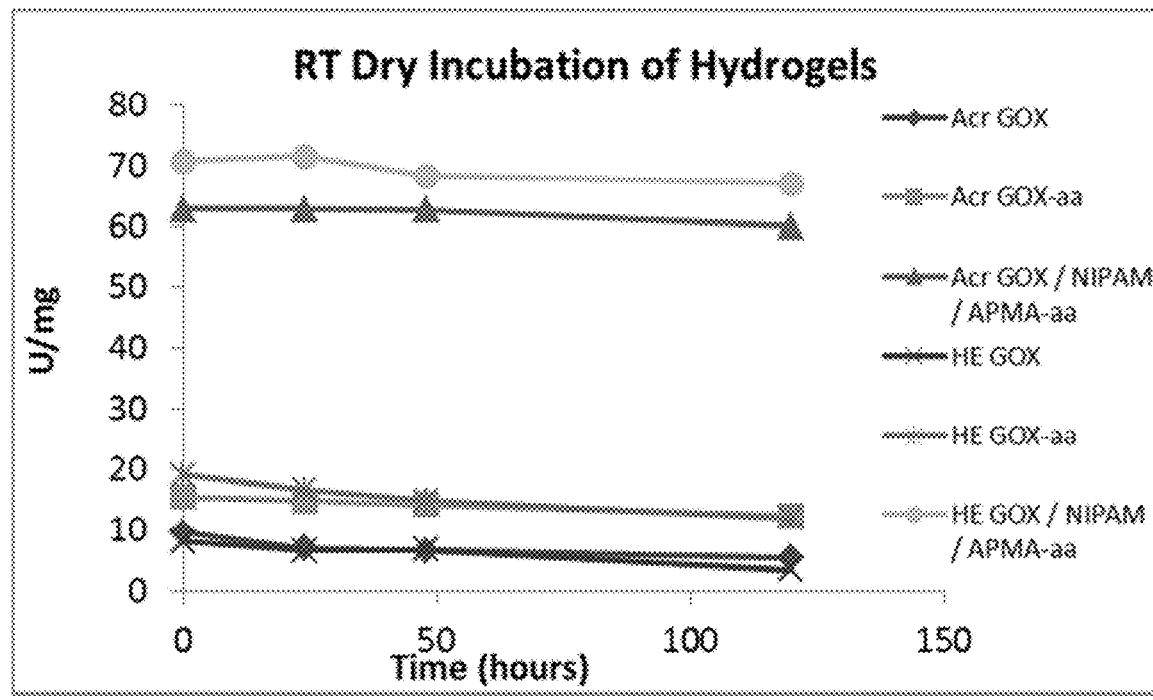
FIG. 43 is a graph containing the catalytic activity of GOX variants retained in hydrogels samples after dry storage at room temperature.
Figure 44:
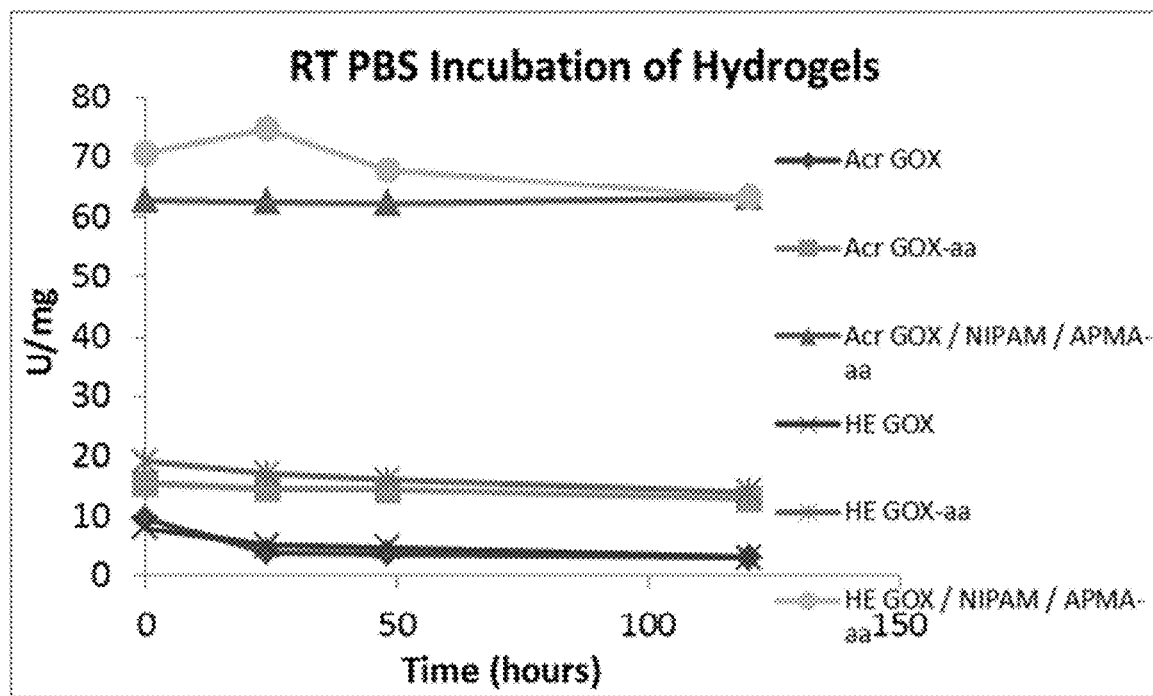
FIG. 44 is a graph containing the catalytic activity of GOX variants retained in hydrogels samples after storage in PBS at room temperature.
Figure 45:
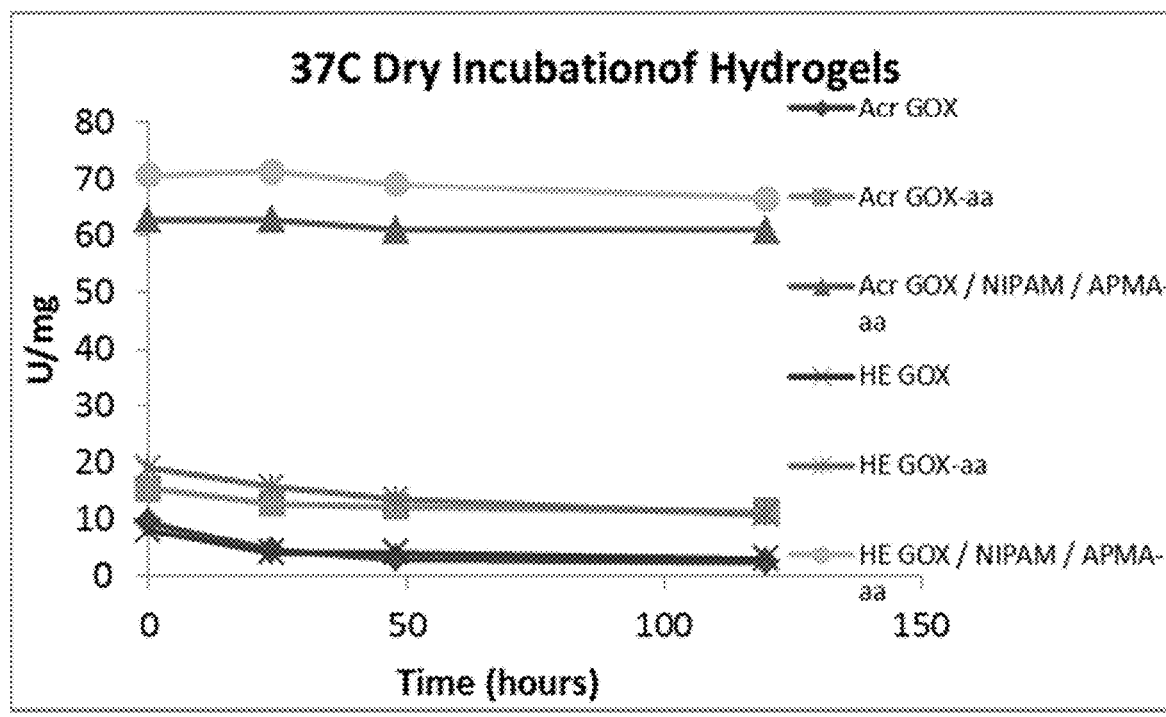
FIG. 45 is a graph containing the catalytic activity of GOX variants retained in hydrogels samples after dry storage at 37° C.
Figure 46:
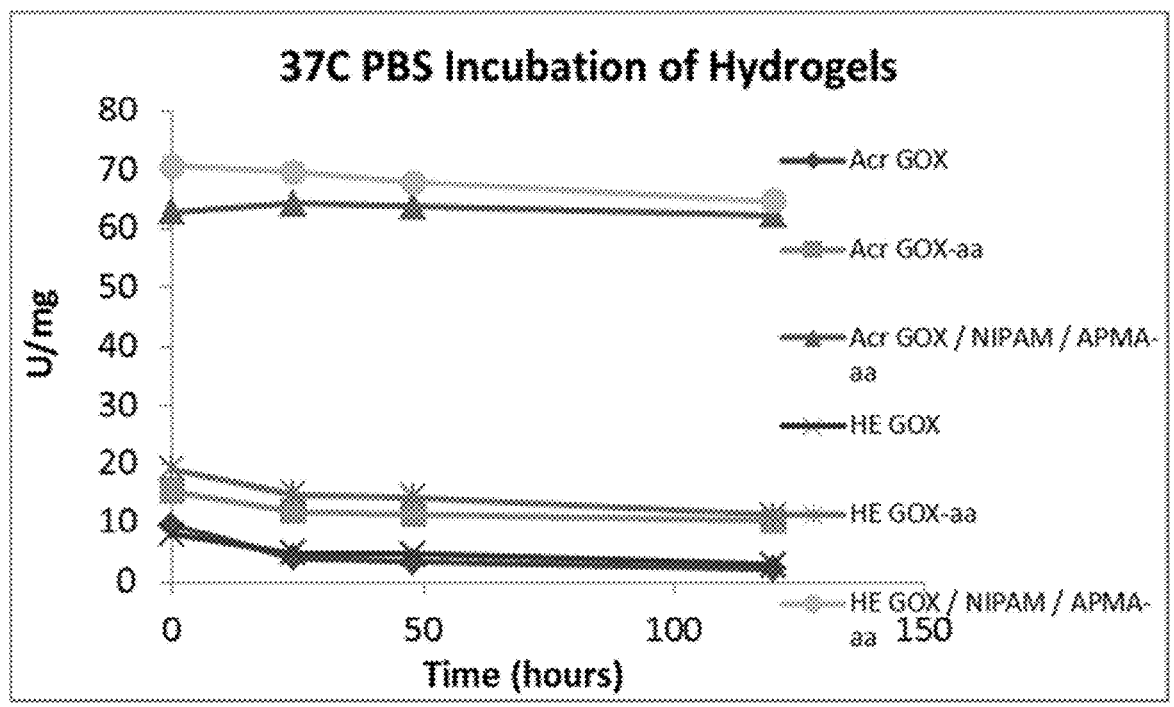
FIG. 46 is a graph containing the catalytic activity of GOX variants retained in hydrogels samples after storage in PBS at 37° C.

The retention of catalytic activity at room temperature of GOX-containing hydrogels stored dry is shown in FIG. 43 and wet storage in PBS buffer is shown in FIG. 44. Native GOX loses approximately half of its catalytic activity when stored at room temperature for 5 days. GOX-aa loses approximately 20% of its catalytic activity when stored at room temperature for 5 days. There is not a significant loss of activity after storage at RT either in dry form or in PBS buffer for NanoStable GOX/pNIPAM/APMA-aa.

The retention of activity at 37° C. of GOX containing hydrogels stored dry is shown in FIG. 25 and wet storage in PBS is shown in FIG. 27. Native GOX-containing hydrogels, when stored at 37° C. either wet or dry, lose more than 75% of their catalytic activity after 5 days. GOX-aa containing hydrogels lose approximately 40% catalytic activity when stored at 37° C. after 5 days. NanoStable GOX/NIPAM/APMA-aa containing hydrogels do not lose any significant activity over 5 days when stored at 37° C. retaining over 90% of their original activity. The addition of the thermopolymer to GOX aids in the enhancement of thermal stability for NanoStable GOX/NIPAM/APMA-aa containing hydrogels.

An additional function to the enzyme can be beaded to the polymer chain to impart various additional functionalities such as amine functionality. Thermal stability resulting from NanoStable technology remains when additional monomers are added. Sensors comprised of NanoStable enzymes are more stable than the current state-of-the-art. Enhanced activity retention is seen after initial curing in hydrogels. NanoStable GOX/NIPAM/APMA-aa was cross-linked into the hydrogel, did not rinse out of the hydrogel and has enhanced thermal stability.

EXAMPLE 16

Glucose Oxidase (GOX) was encapsulated into N-isopropylacrylamide (NiPAM) nanoparticles precisely as described in Walker et. al. U.S. Pat. No. 8,460,907 ('907 nanoparticles). Additionally, Nanostable GOX/NiPAM was prepared according to Examples 6 & 7 of the current invention. Both were prepared from the same stock of GOX in order to directly compare the methods and end products. After each modification step an aliquot was taken of both the '907 nanoparticles and NanoStable GOX/NiPAM of the current invention and kept for analysis to compared to each other and to native GOX.

Figure 47:
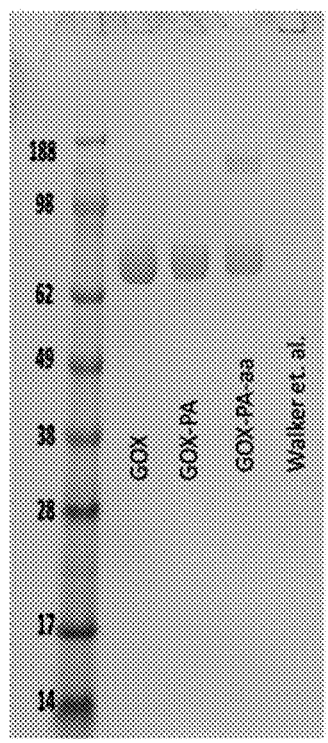
FIG. 47 is a picture of the gel that was made by performing SDS-PAGE on the Walker (U.S. Pat. No. 8,460,907) et. al. nanoparticles throughout the nanoparticle process.
Figure 48:
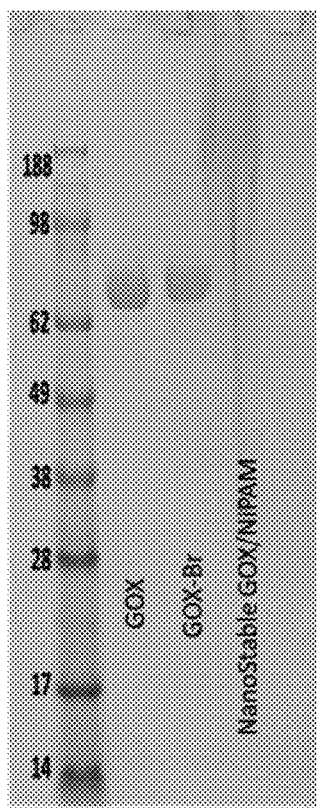
FIG. 48 is a picture of the gel that was made by performing SDS-PAGE on initiator modified GOX, and the NanoStable GOX/pNIPAM.
Figure 49:
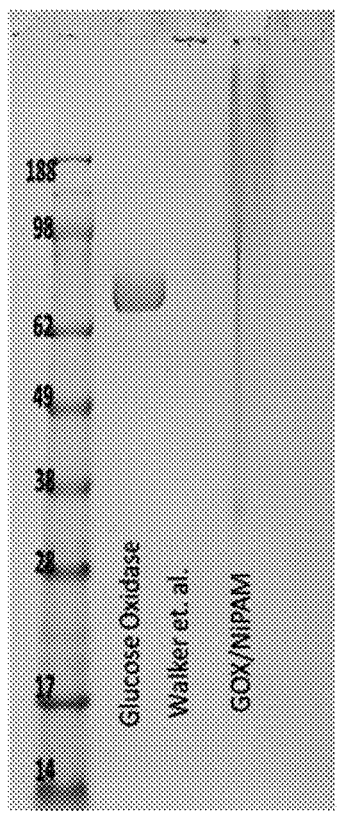
FIG. 49 is a picture of the gel that was made by performing SDS-PAGE on the Walker et. al. (U.S. Pat. No. 8,460,907) nanoparticles and the NanoStable GOX/pNiPAM.

The molecular weight (MW) was estimated at each step via SDS-PAGE of both the '907 nanoparticles (FIG. 47) and Nanostable GOX/pNIPAM of the current invention (FIG. 48). From the SDS-PAGE gel in FIG. 47 native GOX was 80 kD. For the '907 nanoparticles fabrication the molecular weight increased after modification with palmitic acid and increase even further after modification with the acrylic acid. When the '907 nanoparticles were completely modified they would no longer enter into the gel, showing that the molecular weight must be higher than 350 kD. In the SDS-PAGE gel in FIG. 48 GOX was 80 kD. For the current invention, the molecular weight increased after the enzyme was modified with NHS-TEG-Br and the molecular weight increased even further when the modification procedure is complete. However, even after they are fully formed the current invention still enters the SDS-PAGE gel and has a band that goes from 36 kD to 350 kD with the majority of the band appearing at 188 kD. The '907 nanoparticles and the NanoStable GOX/pNIPAM of the current invention were, additionally, ran on the same SDS-PAGE gel for direct comparison (FIG. 49). The results were the same as the individual gels; the '907 particles did not enter the gel and the NanoStable GOX/NiPAM particles had a band from 36 kD to 350 kD with the majority of the band appearing at 188 kD. This indicates that the current invention are truly individual macromolecules which are significantly smaller than the '907 polymeric nanoparticles.

Figure 50:
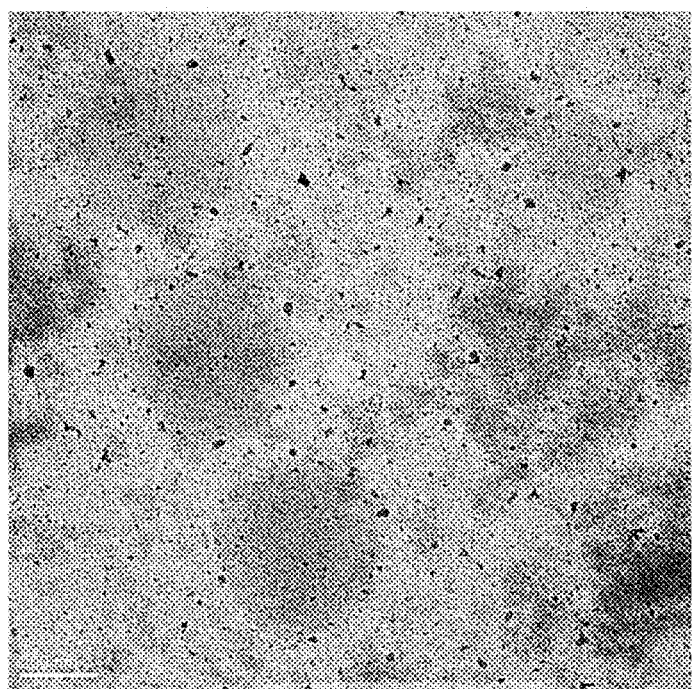
FIG. 50 is a Transmission Electron Microscope Image of the '907 nanoparticles.
Figure 51:
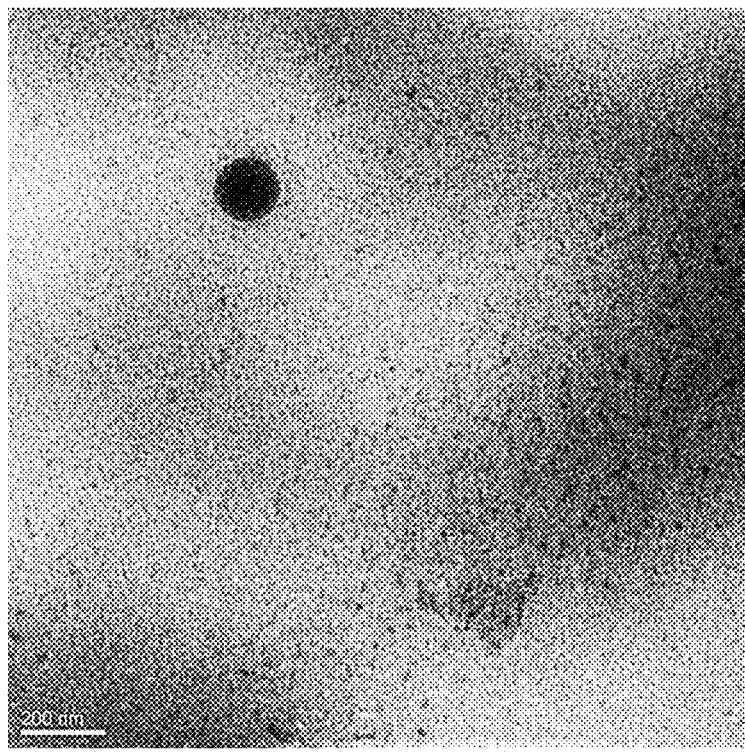
FIG. 51 is a Transmission Electron Microscope Image of the NanoStable GOX/pNiPAM.

The size of the nanoparticles created and relative monodispersity was analyzed by Transmission Electron Microscopy (TEM). A sample of the '907 nanoparticles and the NanoStable GOXpNIPAM of the current invention were separately prepared for analysis. Each was dropped onto a carbon coated copper grid and allowed to dry for 24 hours. After which the analysis was performed. The TEM images for the '907 nanoparticles are in FIG. 50 and the nanoparticles measured 213+/−14.4 nm. The TEM images for NanoStable GOX/pNIPAM of the current invention are in FIG. 51 and the nanoparticles measured 9.4+/−1.7 nm. These results corroborate the results of the SDS-PAGE gel that the particles of the current invention are significantly smaller than the Walker et al. U.S. Pat. No. 8,460,907 nanoparticles.

Figure 52:
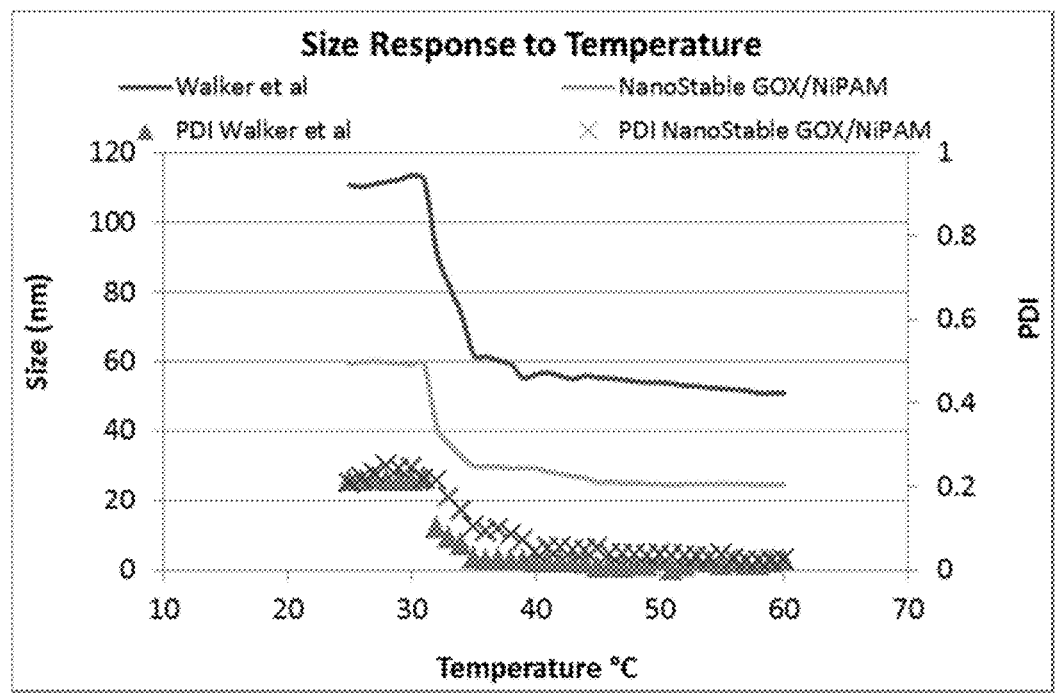
FIG. 52 is a graph of the results of using Dynamic Light Scattering to determine the size of the '907 nanoparticles and the NanoStable GOX/pNiPAM.

The size of the nanoparticles created and relative monodispersity were analyzed by Dynamic Light Scattery (DLS) (FIG. 52). DLS was utilized to compare the hydrodynamic radius of each conjugate and ensure the LCST of pNIPAM (32° C.) was not compromised during nanoparticle synthesis. The Walker et al. U.S. Pat. No. 8,460,907 nanoparticles were 110 nm at temperatures up to 32° C. At temperatures above 32° C., NIPAM collapses and the particles shrunk to 51 nm. NanoStable GOX/pNIPAM nanoparticles of the current invention are 60 nm at temperatures up to 32° C. and contract to 24 nm at temperatures above 32° C. The results corroborate that smaller particles have been created in the current invention. The discrepancies in the actual sizes of each method of sizing are attributed to the known differences in techniques used.

The combination of the TEM images and the gel electrophoresis studies confirm that the invention of Walker et al. '907 is a true polymeric nanoparticle comprised of a plurality of enzymes cross-linked into large, polymer-dense nanoparticles, whereas the materials of the present invention are truly individual enzyme-polymer nanoparticle conjugates that demonstrate an aggregation phenomenon known in the literature to be attributable to the tendency of pNIPAM to stick to itself. The ability of the materials in the present invention to move through the hydrogel in SDS-PAGE illustrates that the present invention is substantially smaller than the particles achieved in Walker et al. U.S. Pat. No. 8,460,907.

Figure 53:
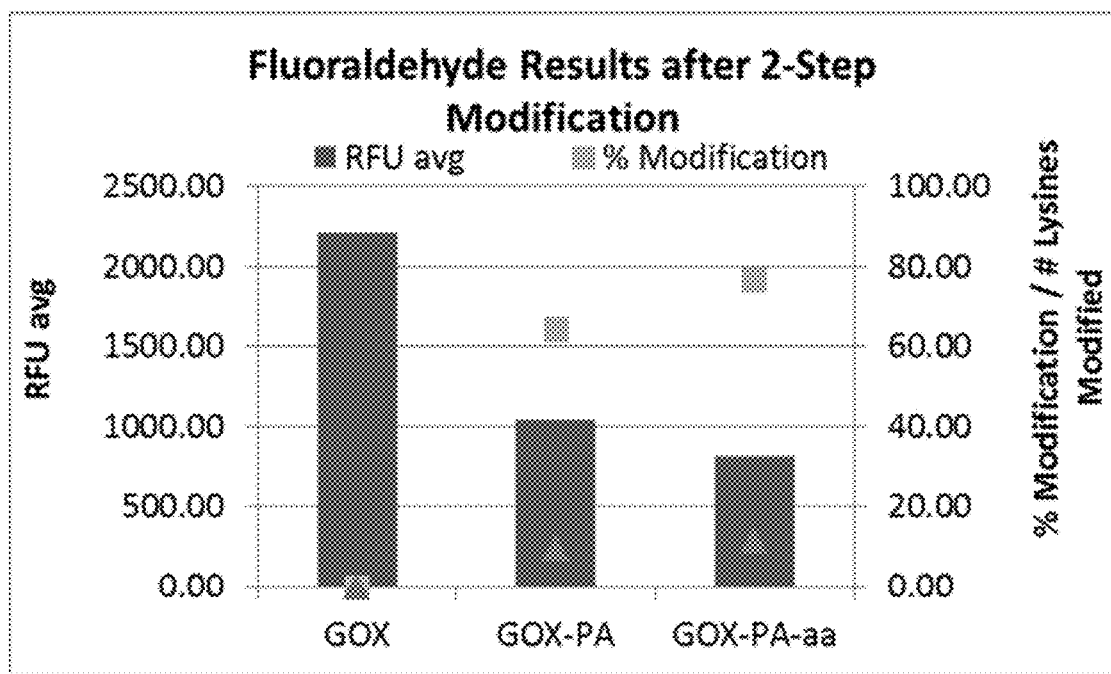
FIG. 53 is a graph of the results of the fluoraldehyde assay that was performed on the '907 nanoparticles throughout the nanoparticle fabrication process.
Figure 54:
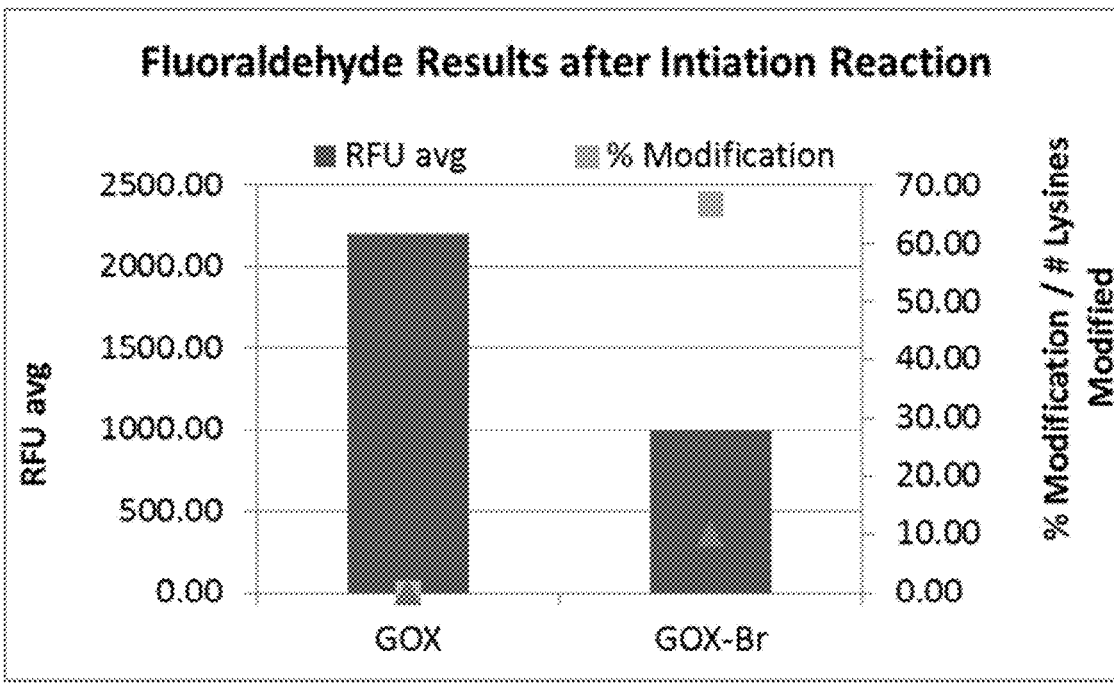
FIG. 54 is a graph of the results of the fluoraldehyde assay that was performed on the NanoStable GOX/pNiPAM particles.

The Rate of modification was monitored via the fluoraldehyde assay as in Example 6. The results of the fluoraldehyde assay for the nanoparticles of Walker et al. U.S. Pat. No. 8,460,907 are pictured in FIG. 53. After adding the Palmitic Acid the results show that the GOX was modified 64%. After adding the Acrylic Acid is showed that the GOX was modified 76%. This corresponds to the SDS-PAGE gel that modification was performed. The results of the fluoraldehyde assay for the NanoStable GOX/pNIPAM of the current invention show that the GOX was modified 65% (FIG. 54) which also corresponds to the SDS-PAGE gel.

The catalytic activity was monitored after each modification step, after each reagent addition, and every 15 minutes throughout the nanoparticle synthesis and after synthesis was complete. The results are depicted in FIGS. 55 and 56. After modification, nanoparticle synthesis and cleanup, the walker et al. U.S. Pat. No. 8,460,907 nanoparticles lose 38% activity, resulting in a retention of 62% of its initial activity (FIG. 55). In contrast, after initiation, polymerization and cleanup, GOX/pNIPAM only loses 3.8% activity, resulting in retention of 96.2% (66.5% improvement) of its initial activity (FIG. 56). The process of the current invention is not detrimental to the catalytic activity of GOX as it is maintained throughout the entire procedure.

EXAMPLE 17

The aqueous stability of native GOX, the '907 nanoparticles and NanoStable GOX/pNIPAM of the current invention were examined at room temperature, 40° C., 50° C., and 60° C. First, samples were diluted into PBS Buffer to 1 mg/mL (protein weight to volume buffer) and incubated at each temperature in triplicate. The PBS buffer used consists of: 10 mM Phosphate Buffer, 137 mM NaCl, 2.7 mM KCl at pH 7.4. Aliquots from each sample were removed and assayed according to the procedure in Example 5 for retention of catalytic activity.

Figure 57:
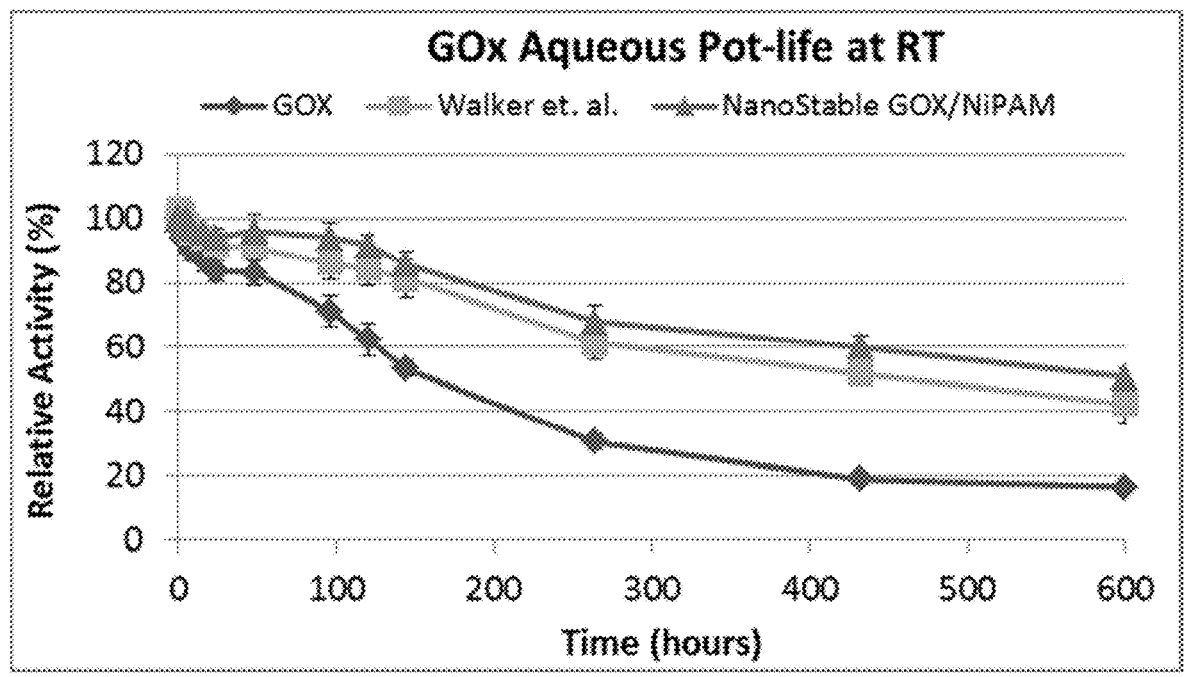
FIG. 57 is a graph of the relative activity of native GOX, the '907 nanoparticles and NanoStable GOX/pNiPAM at room temperature over the course of 600 hours or 25 days.

GOX samples incubated at room temperature were assayed over the course 600 hours or 25 days (FIG. 57). The retention of catalytic activity after 25 days at room temperature is as follows, for native GOX 16.4% was retained, for the Walker et al. U.S. Pat. No. 8,460,907 nanoparticles 42.5% was retained and for NanoStable GOX/pNIPAM 50.8% was retained.

Figure 58:
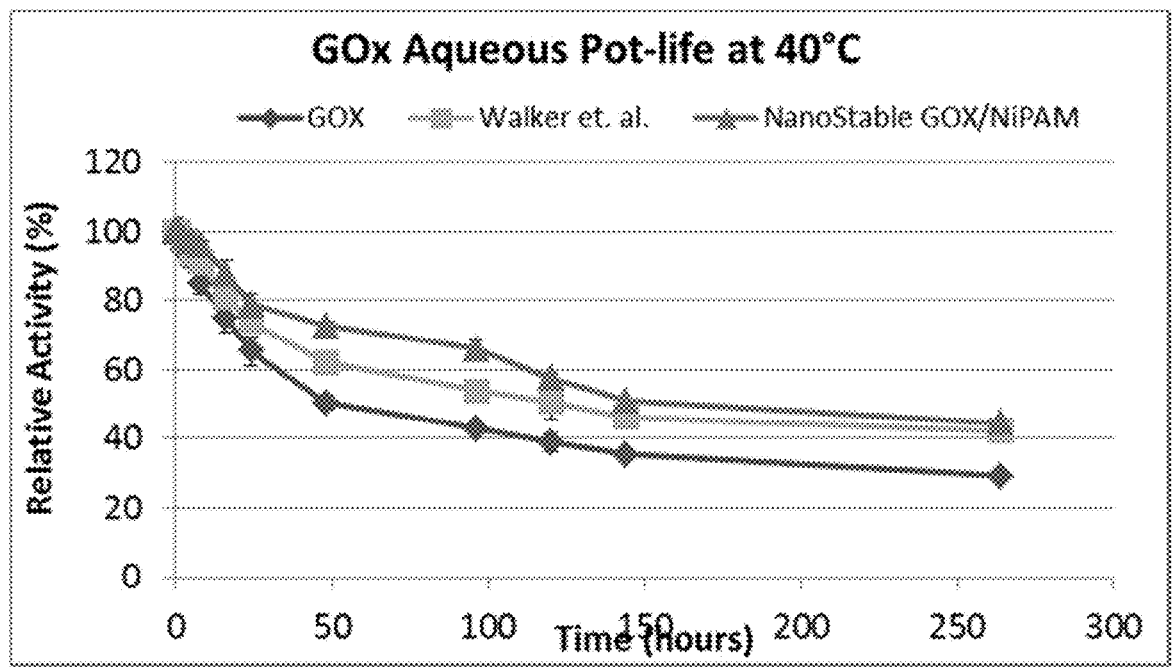
FIG. 58 is a graph of the relative activity of native GOX, the '907 nanoparticles and NanoStable GOX/pNiPAM at 40° C. over the course of 264 hours or 11 days.

GOX samples incubated at 40° C. were assayed over the course of 264 hours or 11 days (FIG. 58). The retention of catalytic activity after 11 days at 40° C. is as follows, for native GOX 29.3% was retained, for the '907 nanoparticles 42.4% was retained and for NanoStable GOX/pNIPAM 44.5% was retained.

Figure 59:
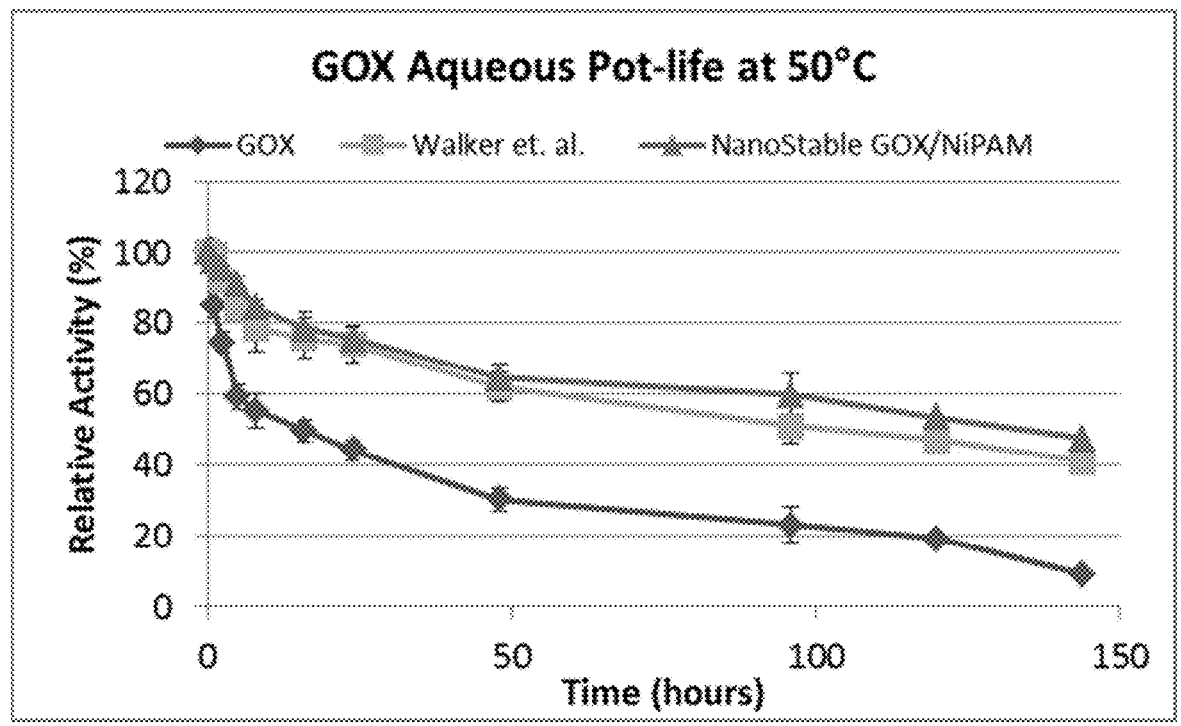
FIG. 59 is a graph of the relative activity of native GOX, the '907 nanoparticles and NanoStable GOX/pNiPAM at 50° C. over the course of 144 hours or 6 days.

GOX samples incubated at 50° C. were assayed over the course of 144 hours or 6 days (FIG. 59). The retention of catalytic activity after 6 days is at 50° C. is as follows, for native GOX 9% was retained, for the Walker et al. U.S. Pat. No. 8,460,907 nanoparticles 40.9% was retained and for NanoStable GOXp/NIPAM 47.4% was retained.

Figure 60:
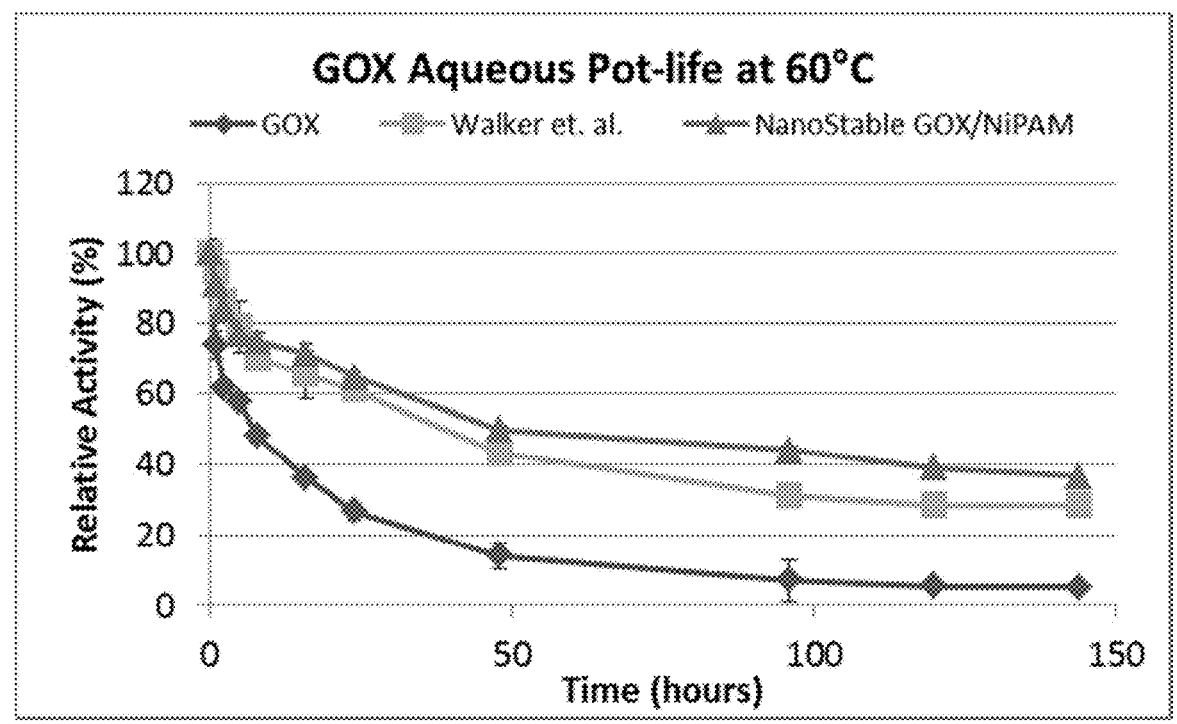
FIG. 60 is a graph of the relative activity of native GOX, the '907 nanoparticles and NanoStable GOXp/NiPAM at 60° C. over the course of 144 hours or 6 days.

GOX samples incubated at 60° C. were assayed over the course of 144 hours or 6 days (FIG. 60). The retention of catalytic activity after 6 days at 60° C. was as follows, for native GOX 5.2% was retained, for the Walker et al. U.S. Pat. No. 8,460,907 nanoparticles 28.4% was retained and for NanoStable GOX/pNIPAM 36.5% was retained.

The same trend is seen at all temperatures tested. The trend is the Walker et al. U.S. Pat. No. 8,460,907 nanoparticles have improved stability over native GOX. Most importantly though the current invention provides further stability over Walker et. al. resulting in a greater retention of catalytic activity across all temperatures. The current invention retains more activity of the initial enzyme and also maintains more activity after incubation at elevated temperatures.

The thermal half-life of inactivation occurs when an enzyme loses precisely 50% of its starting catalytic activity. Utilizing the aqueous stability graphs (FIGS. 57-60) the thermal half-life of inactivation was calculated for native GOX, the walker et al. U.S. Pat. No. 8,460,907 (hereinafter "'907 Patent") nanoparticles and NanoStable GOX/pNIPAM of the current invention.

Nanostable GOX/pNIPAM of the current invention increases the thermal half-life over native GOX by 4.5 fold at room temperature, 3-fold at 40° C., 6.7-fold at 50° C. and 6.4-fold at 60 C. Stability is increased in NanoStable GOX/pNIPAM of the current invention over the '907 Patent nanoparticles by 50% at room temperature, 20% at 40° C., 25% at 50° C., and 60% at 60° C. The current NanoStable GOXpNIPAM nanoparticles result in an increase in aqueous stability of catalytic activity over the prior art.

The current invention results in smaller enzyme/polymer conjugate than the prior art. The smaller enzyme/polymer conjugates result in higher activity nanoparticles. The smaller enzyme/polymer conjugates also retained more activity after storage at elevated temperatures. This is confirmed by dynamic light scattering, SDS-Page and TEM. Comparing the activity of the starting native GOX to the resulting activity of the end product, NanoStable GOX/pNIPAM has a dramatic increase in retention of catalytic activity over Walker et. al. (U.S. Pat. No. 8,460,907) nanoparticles, 96.2% vs. 62%, respectively. The NanoStable GOX/pNIPAM nanoparticles preserve the catalytic activity of GOX better than any other known methods for protection at elevated temperatures.

What is claimed is:

1. A biomolecule conjugate comprising:
one functionalized biomolecule, said biomolecule is functionalized with one or more sites;
at least one polymer chain having a first end and a second end;
said first end of said chain is attached to said site on said functionalized biomolecule;
said second end of said chain is free moving;
said chain comprises a block copolymer having at least a first polymer block and a second polymer block, wherein said first polymer block is stimuli responsive, wherein said chain collapses in response to said stimuli and envelopes said functionalized biomolecule to form a reversible nanoparticle structure; and
wherein said chain in not cross-linked.

2. The biomolecule conjugate of claim 1 wherein said functionalized biomolecule is one or more enzymes, proteins, antibodies, or biological catalysts.

3. The biomolecule conjugate of claim 2 wherein said enzyme, protein, or biological catalyst remains in a folded position and retains active conformation within said nanoparticle structure.

4. The biomolecule conjugate of claim 1 wherein said biomolecule is functionalized with a site that is at least one of the moieties selected from a group consisting of an amine, a carboxylate, a vincinal diol, a lysine residue, and a thiol group.

5. The biomolecule conjugate of claim 1 wherein said first polymer block is thermally responsive and selected from the group consisting of a poly(N-isopropylacrylamide), a poly (isopropyl-N-vinylpyrrolidone), a polymer which undergoes a conformational change when heated, and combinations thereof.

6. The biomolecule conjugate of claim 1 that has improved stability over a native biomolecule at temperatures greater than 30 degrees Centigrade in both aqueous solutions and dry powders.

7. The biomolecule conjugate of claim 2 wherein said enzymes are selected from the group consisting of organophosphorous hydrolase (OPH), organophosphorous acid anhydrolase (OPAA), butyrylcholinesterase, glucose oxidase (GOX), acetylcholinesterase (AChE), dehalogenase (DHG), diisopropylfluorophosphatase (DFPase), chloroperoxidase, lipase and urease.

8. The biomolecule conjugate of claim 1 wherein said second polymer block provides an additional functionality than said chain collapsing response to a stimuli.

9. The biomolecule conjugate of claim 8 wherein said second polymer block includes one or more primary amines.

10. The biomolecule conjugate of claim 9 wherein said second polymer block is N-(3-aminopropyl)methacrylamide hydrochloride (APMA).

11. The biomolecule conjugate of claim 1 wherein said second polymer block is poly(ethylene glycol) methyl ether methacrylate.

12. The biomolecule conjugate of claim 1 wherein said chain is attached to said functionalized biomolecule using a polymerization initiator that has been covalently attached to the biomolecule prior to attaching said chain.

13. The biomolecule conjugate of claim 12 wherein said polymerization initiator is succinimidyl-tetraethylene glycol (TEG)-bromide.

14. The biomolecule conjugate of claim 1 wherein said chain is not cross-linked to a second chain on said biomolecule, or to another biomolecule or a chain on another biomolecule.

15. The biomolecule conjugate of claim 1 wherein said biomolecule conjugate is from 5 nm to 200 nm in size.

16. The biomolecule conjugate of claim 1 wherein said block copolymer further comprises a third polymer block.

17. A sensor comprising the biomolecule conjugate of claim 1.

18. The sensor of claim 17 wherein said functionalized biomolecule is one or more enzymes, proteins, antibodies, or biological catalysts.

19. The sensor of claim 18 wherein said enzymes are selected from the group consisting of organophosphorous hydrolase (OPH), organophosphorous acid anhydrolase (OPAA), butyrylcholinesterase, glucose oxidase (GOX), acetylcholinesterase (AChE), dehalogenase (DHG), diisopropylfluorophosphatase (DFPase), urease, chloroperoxidase and Factor VIIa.

20. The sensor of claim 19 including a glucose sensing element with enhanced thermal stability.

21. The sensor of claim 20 wherein said glucose sensing element comprises a GOX containing hydrogel.

22. The sensor of claim 17 wherein said first polymer block is thermally responsive and selected from the group consisting of a poly(N-isopropylacrylamide), a poly(isopropyl-N-vinylpyrrolidone), a polymer which undergoes a conformational change when heated, and combinations thereof.

23. The sensor of claim 17 that has improved stability over a native biomolecule at temperatures greater than 30 degrees Centigrade in both aqueous solutions and dry powders.

* * * * *

UNITED STATES PATENT AND TRADEMARK OFFICE
CERTIFICATE OF CORRECTION

PATENT NO. : 10,808,238 B2
APPLICATION NO. : 14/581203
DATED : October 20, 2020
INVENTOR(S) : Walker et al.

Page 1 of 1

It is certified that error appears in the above-identified patent and that said Letters Patent is hereby corrected as shown below:

In the Claims

In Column 37, Claim 1, Line 30, delete "chain in not cross-linked" and insert -- chain is not cross-linked --.

Signed and Sealed this
Second Day of February, 2021

Drew Hirshfeld
*Performing the Functions and Duties of the
Under Secretary of Commerce for Intellectual Property and
Director of the United States Patent and Trademark Office*